(12) United States Patent
Lo

(10) Patent No.: US 11,370,819 B2
(45) Date of Patent: *Jun. 28, 2022

(54) TARGETED TGFβ INHIBITION

(71) Applicant: Merck Patent GmbH, Darmstadt (DE)

(72) Inventor: Kin-Ming Lo, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 190 days.

This patent is subject to a terminal disclaimer.

(21) Appl. No.: 16/522,304

(22) Filed: Jul. 25, 2019

(65) Prior Publication Data

US 2020/0055949 A1 Feb. 20, 2020

Related U.S. Application Data

(63) Continuation of application No. 15/617,876, filed on Jun. 8, 2017, now abandoned, which is a continuation of application No. 14/618,454, filed on Feb. 10, 2015, now Pat. No. 9,676,863.

(60) Provisional application No. 61/938,048, filed on Feb. 10, 2014.

(51) Int. Cl.
| | |
|---|---|
| *C07K 16/28* | (2006.01) |
| *C07K 14/495* | (2006.01) |
| *C07K 19/00* | (2006.01) |
| *C07K 14/705* | (2006.01) |
| *A61K 38/17* | (2006.01) |
| *A61K 39/395* | (2006.01) |
| *A61K 39/00* | (2006.01) |
| *C07K 16/00* | (2006.01) |
| *C07K 14/71* | (2006.01) |

(52) U.S. Cl.
CPC ........ *C07K 14/495* (2013.01); *C07K 16/2827* (2013.01); *C07K 16/2866* (2013.01); *C07K 19/00* (2013.01); *A61K 38/177* (2013.01); *A61K 39/3955* (2013.01); *A61K 2039/505* (2013.01); *C07K 14/70532* (2013.01); *C07K 14/71* (2013.01); *C07K 16/00* (2013.01); *C07K 16/2863* (2013.01); *C07K 16/2896* (2013.01); *C07K 2319/00* (2013.01); *C07K 2319/33* (2013.01)

(58) Field of Classification Search
CPC ..... C07K 14/71; C07K 16/2827; C07K 19/00
See application file for complete search history.

(56) References Cited

U.S. PATENT DOCUMENTS

| | | | |
|---|---|---|---|
| 5,785,682 A | 7/1998 | Grabenkort | |
| 7,943,743 B2 | 5/2011 | Korman et al. | |
| 8,217,149 B2 | 7/2012 | Irving et al. | |
| 8,815,247 B2 | 8/2014 | Govindappa et al. | |
| 9,676,863 B2 | 6/2017 | Lo | |
| 9,850,306 B2 | 12/2017 | Bedi et al. | |
| 2003/0044423 A1 | 3/2003 | Gillies et al. | |
| 2003/0166877 A1 | 9/2003 | Gillies et al. | |
| 2005/0079559 A1 | 4/2005 | Matsuzaki et al. | |
| 2006/0228332 A1 | 10/2006 | Gillies et al. | |
| 2007/0244042 A1 | 10/2007 | Sun et al. | |
| 2010/0203056 A1 | 8/2010 | Irving et al. | |
| 2011/0117110 A1 | 5/2011 | Akamatsu et al. | |
| 2012/0269807 A1 | 10/2012 | Pardridge et al. | |
| 2013/0287802 A1 | 10/2013 | Govindappa et al. | |
| 2014/0127200 A1 | 5/2014 | Barbas, III | |
| 2014/0341917 A1 | 11/2014 | Nastri et al. | |
| 2015/0190506 A1 | 7/2015 | Cheung et al. | |
| 2015/0225483 A1 | 8/2015 | Lo | |
| 2015/0376271 A1 | 12/2015 | Perlroth et al. | |
| 2016/0106835 A1 | 4/2016 | Hoos et al. | |
| 2016/0177276 A1 | 6/2016 | Lo et al. | |
| 2016/0340430 A1 | 11/2016 | Bedi et al. | |
| 2017/0143826 A1 | 5/2017 | Dupont et al. | |
| 2018/0002436 A1 | 1/2018 | Lo | |
| 2020/0055949 A1 | 2/2020 | Lo | |

FOREIGN PATENT DOCUMENTS

| | | |
|---|---|---|
| EP | 2542590 A2 | 1/2013 |
| WO | WO-2001/058957 | 8/2001 |
| WO | WO-2005/065691 A1 | 7/2005 |
| WO | WO-2008/157367 A1 | 12/2008 |
| WO | WO-2009/152610 A1 | 12/2009 |
| WO | WO-2010/003118 A1 | 1/2010 |
| WO | WO-201 0/077634 A1 | 7/2010 |
| WO | WO-2011/066389 A1 | 6/2011 |
| WO | WO-2011/109789 A2 | 9/2011 |
| WO | WO-2013/019906 A1 | 2/2013 |
| WO | WO-2013/079174 A1 | 6/2013 |
| WO | WO-2013/164694 A1 | 11/2013 |
| WO | WO-2013/181452 A1 | 12/2013 |

(Continued)

OTHER PUBLICATIONS

Bandyopadhyay et al. (2010) "Doxorubicin in combination with a small TGFbeta inhibitor: a potential novel therapy for metastatic breast cancer in mouse models," PLoS One, 5(4):e10365 (13 pages).

(Continued)

*Primary Examiner* — Zachary C Howard

(74) *Attorney, Agent, or Firm* — Goodwin Procter LLP

(57) ABSTRACT

This invention relates generally to bifunctional molecules including (a) a TGFβRII or fragment thereof capable of binding TGFβ and (b) an antibody, or antigen binding fragment thereof, that binds to an immune checkpoint protein, such as Programmed Death Ligand 1 (PD-L1), uses of such molecules (e.g., for treating cancer), and methods of making such molecules.

20 Claims, 24 Drawing Sheets

Specification includes a Sequence Listing.

(56) References Cited

FOREIGN PATENT DOCUMENTS

| WO | WO-2015/118175 A2 | 8/2015 |
|---|---|---|
| WO | WO-2015/132602 A1 | 9/2015 |

OTHER PUBLICATIONS

Bhat et al., (2017), "Interferon-γ derived from cytotoxic lymphocytes directly enhances their motility and cytotoxicity," *Cell Death and Disease*, Jun. 1;8(6):e2836.

Camphausen K et al. (2001) "Radiation Therapy to a Primary Tumor Accelerates Metastatic Growth in Mice," Cancer Res, 61(5):2207-11.

Chen et al. (2003) "Conversion of peripheral CD4+CD25− naive T cells to CD4+CD25+ regulatory T cells by TGF-beta induction of transcription factor Foxp3," J Exp Med, 198(12):1875-86.

Cheng et al. (2013) "Structure and interactions of the human programmed cell death 1 receptor," J Biol Chem, 288(17):11771-85.

Coe et al. (2010) "The roles of antigen-specificity, responsiveness to transforming growth factor-beta and antigen-presenting cell subsets in tumour-induced expansion of regulatory t cells," Immunology, 131:556-569.

Fujita et al. (2009) "Inhibition of Transforming Growth Factor-beta-mediated immunosuppression in Tumor-Draining Lymph nodes augments antitumor responses by various immunologic cell types," Cancer Res, 69:5142-5150.

Hart et al., (2002) "Crystal structure of the human TbetaR2 ectodomain—TGF-beta3 complex," Nat Struct Biol. 9(3):203-8.

Huber et al. (2006) "TGF-beta and CD4+CD25+ Regulatory T Cells," Frontiers in Bioscience, 11:1014-1023.

Knudson et al., "Abstract 594: Dual targeting of TGFb and PD-L1 promotes potent anti-tumor efficacy in multiple murine models of solid carcinomas," Cancer Res Jul. 1, 2017 (77) (13 Supplement) 594; DOI: 10.1158/1538-7445.AM2017-594.

Kobie et al. (2003) "Transforming Growth Factor beta Inhibits the Antigen-Presenting Functions and Antitumr Activity of Dendritic Cell vaccines," Cancer Research, 63:1860.

Kranz et al., CIMT 2016: Mechanisms of efficacy in cancer immunotherapy—Report on the 14th Annual Meeting of the Association for Cancer Immunotherapy, May 10-12, 2016, Mainz, Germany. Hum Vaccin Immunother. Nov. 2016;12(11):2805-2812. Epub Jul. 19, 2016.

Lin et al. (2008) The PD-1/PD-L1 complex resembles the antigen-binding Fv domains of antibodies and T cell receptors, Proc Natl Acad Sci U S A, 105(8):3011-6.

Luo X et al. (2005) "Systemic transforming growth factor-beta1 gene therapy induces Foxp3+ regulatory cells, restores self-tolerance, and facilitates regeneration of beta cell function in overtly diabetic nonobese diabetic mice," Transplantation, 79(9):1091-6.

Langer R (1990) 'New Methods of Drug Discovery,' Science, 249(4976):1527-33.

Morris et al. (2008) 'Autoimmune Hemolytic Anemia Associated with Ovarian Cancer,' J Clin Oncol, 26(30):4993-5.

Stewart R et al. (2015) 'Identification and Characterization of MEDI4736, an Antagonistic Anti-Pd-L1 Monoclonal Antibody,' Cancer Immunol Res, 3(9):1052-62.

Strauss J et al. (2016) "A phase I, open-label, multiple-ascending-dose trial to investigate the safety, tolerability, pharmacokinetics, biological, and clinical activity of M7824, a novel bifunctional fusion protein targeting the PD-L1 and TGF-β pathways, in patients with metastatic or locally advanced solid tumor," Eur J Cancer. 68(suppl 1):S103 [abstract 314].

Zeh HJ 3rd et al. (1999) 'High Avidity CTLs for Two Self-Antigens Demonstrate Superior in vitro and in vivo Antitumor Efficacy,' J Immunol, 162(2):989-94.

Aiello et al., "Suppression of retinal neovascularization in vivo by inhibition of vascular endothelial growth factor (VEGF) using soluble VEGF-receptor chimeric proteins", Pro Natl Acad Sci USA. Nov. 7, 1995; 92(23): 10457-61.

Amarnath et al., The PDL1-PD1 Axis Converts Human TH1 Cells into Regulatory T Cells, *Sci Transl Med*, 3(111):111ra120 (2011).

Angal et al., "A Single Amino Acid Substitution Abolishes the Heterogeneity of Chimeric Mouse/Human (IgG4) Antibody," *Mol Immunol.*, vol. 30, pp. 105-108 (1993).

Bartram et al., "Double-Outlet Right Ventricle and Overriding Tricuspid Valve Reflect Disturbances of Looping, Myocardialization, Endocardial Cushion Differentiation, and Apoptosis in TGF-β2-Knockout Mice," *Circulation*, vol. 103, pp. 2745-2752 (2001).

Bendig, M.M. "Humanization of rodent monoclonal antibodies by CDR grafting", Methods: A companion to Methods in Enzymology, 1995, vol. 8, p. 83-93.

Bierie et al., "Tumour microenvironment: TGFbeta: the molecular Jekyll and Hyde of cancer," *Nat Rev Cancer*, vol. 6, pp. 506-520 (2006).

Boado et al., "Selective targeting of a TNFR decoy receptor pharmaceutical to the primate brain as a receptor-specific IgG fusion protein", J. Biotechnol, Mar. 2010; 146(1-2):84-91.

Bremer et al., "Simultaneous inhibition of epidermal growth factor receptor (EGFR) signaling and enhanced activation of tumor necrosis factor-related apoptosis-inducing ligand (TRAIL) receptor-mediated apoptosis induction by an scFv:s TRAIL fusion protein with specificity for human EGFR", J Biol Chem. Mar. 18, 2005; 280(11): 10025-33.

Bujak et al., "The role of TGF-β signaling in myocardial infarction and cardiac remodeling," *Cardiovasc Res.*, vol. 74, pp. 184-195 (2007).

Calone et al., "Inhibition of TGFβ Signaling and its Implications in Anticancer Treatments," *Exp Oncol.*, vol. 34, pp. 9-16 (2012).

Casset, et al. "A peptide mimetic of an anti-CD4 monoclonal antibody by rational design", Biochem. Biophys. Res. Comm., 2003, vol. 307, p. 198-205.

Chemnitz et al., RNA Fingerprints Provide Direct Evidence for the Inhibitory Role of TGF β and PD-1 on CD4+ T Cells in Hodgkin Lymphoma, *Blood*, 110(9):3226-33 (2007).

Connolly et al., "Complexities of TGF-β Targeted Cancer Therapy," *Intl J Biol Sci.*, vol. 8, pp. 964-978, (2012).

Curran et al., PD-1 and CTLA-4 Combination Blockade Expands Infiltrating T Cells and Reduces Regulatory T and Myeloid Cells with B16 Melanoma Tumors, *Proc Natl Acad Sci USA*, 107(9):4275-80 (2010).

Fairbrother et al., "Novel peptides selected to bind vascular endothelial growth factor target the receptor-binding site", Biochemistry, Dec. 22, 1998; 37(51): 1775-65.

Fernandez-Botran et al., (2002), "Soluble Cytokine Receptors in Biological Therapy," *Expert Opin Biol Ther*, 2(6):585-605.

Fife et al., "Interactions Between PD-1 and PD-L1 Promote Tolerance by Blocking the TCR-Induced Stop Signal," *Nat Immunol*, 10(11):1185-92 (2009).

Flavell et al., "The polarization of immune cells in the tumour environment by TGFβ," *Nat Rev Immunol.*, vol. 10, pp. 554-567 (2010).

Francisco et al., PD-L1 Regulated the Development, Maintenance, and Function of Induced Regulatory T Cells, *J Exp Med*, 206(13):3015-29 (2009).

Gajewski et al., (2006),"Immune Suppression in the Tumor Microenvironment," *J Immunother*, 29(3):233-40.

Gillies et al., "Biological activity and in the vivo clearance of antitumor antibody/cytokine fusion proteins" Bioconjug Chem. May-Jun. 1993; 4(3): 230-5.

Gillies et al., (2002), "Improved circulating half-life and efficacy of an antibody-interleukin 2 immunocytokine based on reduced intracellular proteolysis," *Clin. Cancer Res.*, vol. 8, pp. 210-216.

Hui et al., (2009), "Tumor Necrosis Factor Receptor-IgG Fusion Protein for Targeted Drug Delivery Across the Human Blood-Brain Barrier," *Mol Pharm*, 6(5):1536-43.

Hume et al., (2012), "Therapeutic applications of macrophage colony-stimulating factor-1 (CSF-1) and antagonists of CSF-1 receptor (CSF-1R) signaling," *Blood*, vol. 119, pp. 1810-1820.

International Search Report and Written Opinion for International Application No. PCT/EP2015/052781, dated Aug. 5, 2015 (15 pages).

(56) References Cited

OTHER PUBLICATIONS

Jung et al., "Double anti-angiogenic and anti-inflammatory protein Valpha targeting VEGF-A and TNF-alpha in retinopathy and psoriasis", J Biol Chem. Apr. 22, 2011;286(16):14410-8.
Khaw et al., "A Phase III Study of Subconjunctival Human Anti-Transforming Growth Factor β2 Monoclonal Antibody (CAT-152) to Prevent Scarring after First-Time Trabeculectomy," vol. 114, pp. 1822-1830 (2007).
Koh et al., "Double antiangiogenic protein, DAAP, targeting VEGF-A and angiopoientins in tumor angiogenesis, metastasis, and vascular leakage" Cancer Cell. Aug. 9, 2010; 18(2): 171-84.
Kyi et al., "Checkpoint blocking antibodies in cancer immunotherapy," *FEBS Letters*, vol. 588, pp. 368-376 (2013).
Li et al., "Transforming Growth Factor-β (TGF-β)-Mediated Immunosuppression in the Tumor-Bearing State: Enhanced Production of TGF- β and a Progressive Increase in TGF- β Susceptibility of Anti-Tumor CD4+T Cell Function," *Jpn J Cancer Res*, 84(3):315-25 (1993).
Lin et al., "The Soluble Exoplasmic Domain of the Type II Transforming Growth Factor (TGF)-β Receptor," *J Biol Chem.*, vol. 270, pp. 2747-2754 (1995).
Liossis et al., "Monoclonal anitbodies and fusion proteins in medicine" J Allergy Clin Immunol. Oct. 2005; 116(4): 721-9.
Lopez-Casillas et al., "Betaglycan Can Act as a Dual Modulator of TGF-β Access to Signaling Receptors: Mapping of Ligand Binding and GAG Attachment Sites," *J Cell Biol.*, vol. 124, pp. 557-568 (1994).
Lum et al., "Targeting T Cells with Bispecific Antibodies for Cancer Therapy", BioDrugs. Dec. 1, 2011: 25(6): 365-379.
MacCallum, R.M., et al. "Antibody-antigen interactions: Contact analysis and binding site topography", J. Mol. Biol., 1998, vol. 262, p. 732-745.
Melero et al., "Clinical Development of Immunostimulatory Monoclonal Antibodies and Opportunities for Combination," *Clin Cancer Res.*, vol. 19, pp. 997-1008 (2013).
Mendoza et al., "Betaglycan has Two Independent Domains Required for High Affinity TGF-β Binding: Proteolytic Cleavage Separates the Domains and Inactivates the Neutralizing Activity of the Soluble Receptor," *Biochemistry*, vol. 48, pp. 11755-11765 (2009).
Menzies et al., "Recent advances in melanoma systemic therapy, BRAF inhibitors, CTLA4 antibodies and beyond," *Eur J Cancer*, vol. 49, pp. 3229-3241 (2013).
Montero-Julian et al., "Pharmacokinetic Study of Anti-Interleukin-6 (IL-6) Therapy with Monoclonal Antibodies: Enhancement of IL-6 Clearance by Cocktails of Anti-IL-6 Antibodies," *Blood*, vol. 85, pp. 917-924 (1995).
Morris et al., "Phase I/II study of GC1008: A human anti-transforming growth factor-beta (TGFβ) monoclonal antibody (MAb) in patients with advanced malignant melanoma (MM) or renal cell carcinoma (RCC)," *J Clin Oncol.*, vol. 26, 1 page (2008).
Ngiow et al., (2011), "Anti-TIM3 antibody promotes T cell IFN-γ-mediated antitumor immunity and suppresses established tumors," *Cancer Res.*, vol. 71, pp. 3540-3551.
Pardoll, (2012), Drew M., "Immunology beats cancer: a blueprint for successful translation," *Nat Immunol.*, vol. 13, pp. 1129-1132.
Pardoll, Drew M., (2012), "The blockade of immune checkpoints in cancer immunotherapy," *Nat Rev Cancer*, vol. 12, pp. 252-264.
Paul, W.E. "Fundamental Immunology", 3rd Edition, 1993, pp. 292-295.
Podar et al., (2007), "Inhibition of the TGF-β Signaling Pathway in Tumor Cells," *Recent Results Cancer Res*, 172:77-97.
Roberts et al., (1992), "Role of Transforming Growth Factor-β in Maintenance of Function of Cultured Neonatal Cardiac Myocytes," *J Clin Invest.*, vol. 90, pp. 2056-2062.
Schrama et al., (2006), "Antibody Targeted Drugs as Cancer Therapeutics," *Nat Rev Drug Discov*, 5(2):147-59.
Suzuki et al., (2004), "Soluble Type II Transforming Growth Factor-β Receptor Inhibits Established Murine Malignant Mesothelioma Tumor Growth by Augmenting Host Antitumor Immunity," *Clin Cancer Res.*, vol. 10, pp. 5907-5918.

Trail and Bianchi, (1999), "Monoclonal Antibody Drug Conjugates in the Treatment of Cancer," *Curr Opin Immunol*, 11(5):584-8.
Verona et al., (2008), "Expression, purification and characterization of BGERII: a novel pan-TGFβ inhibitor," *Protein Eng Des Sel.*, vol. 21, pp. 463-473.
Vilchis-Landeros et al., "Recombinant soluble betaglycan is a potent and isoform-selective transforming growth factor-β neutralizing agent," *Biochem J.*, vol. 355, pp. 215-222 (2001).
Wang et al., "Programmed Death 1 Ligand Signaling Regulates the Generation of Adaptive Foxp3+CD4+ Regulatory T Cells," *Proc Natl Acad Sci USA*, 105(27):9331-6 (2008).
Wei et al., "Tumor-Induced Immune Suppression of in vivo Effector T-Cell Priming is Mediated by the B7-H1/PD-1 Axis and Transforming Growth Factor β," *Cancer Res*, 68(13):5432-8 (2008).
Wherry, John E., "T cell exhaustion," *Nat Immunol.*, vol. 12, pp. 492-499 (2011).
Won et al., "Tumorigenicity of Mouse Thymoma is Suppressed by Soluble Type II Transforming Growth Factor β Receptor Therapy," Cancer Res., vol. 59, pp. 1273-1277, (1999).
Woo et al., "Immune inhibitory molecules LAG-3 and PD-1 synergistically regulate T-cell function to promote tumoral immune escape," *Cancer Res.*, vol. 72, pp. 917-927 (2012).
Yamagishi et al., "Expression of the Tgfβ2 Gene During Chick Embryogenesis," *Anat Rec.*, vol. 295, pp. 257-267 (2012).
Yang et al., "TGF-β and immune cells: an important regulatory axis in the tumor microenvironment and progression," *Trends in Immunology*, vol. 31, pp. 220-227 (2010).
Yang et al., "Transforming Growth Factor β: Tumor Suppressor or Promoter? Are Host Immune Cells the Answer?," *Cancer Res*, vol. 68, pp. 9107-9111 (2008).
Zahorowska et al., (2009), "Combined Therapies for Cancer: A Review of EGFR-Targeted Monotherapy and Combination Treatment with Other Drugs," *J Cancer Res Clin Oncol*, 135(9):1137-48.
Zhong et al., "Anti-Transforming Growth Factor β Receptor II Antibody Has Therapeutic Efficacy against Primary Tumor Growth and Metastasis through Multieffects on Cancer, Stroma, and Immune Cells," *Clin Cancer Res.*, vol. 16, pp. 1191-1205, with supplementary material (8 pages) (2010).
Zitvogel et al., "Immunological Aspects of Cancer Chemotherapy," *Nat Rev Immunol*, 8(1):59-73 (2008).
Ganss et al., (1998), "Tumor microenvironment can restrict the effectiveness of activated antitumor lymphocytes," Cancer Res., 58(20):4673-81.
Rudikoff et al., (1982), "Single amino acid substitution altering antigen-binding specificity," Proc Natl Acad Sci USA, 79(6):1979-83.
Siegel et al., (2003), "Cytostatic and apoptotic actions of TGF-beta in homeostasis and cancer," Nat Rev Cancer, 3(11):807-21.
Singer and Berg, (1998) "Genes and Genomes" vol. 1, Yankovsky, ed., pp. 63-64, (In original Russian with English translation).
Takaku et al., (2010), "Blockade of TGF-beta enhances tumor vaccine efficacy mediated by CD8(+) T cells," Int. J. Cancer, 126(7):1666-74.
Truong et al., (1993), "Association of transforming growth factor-beta 1 with prostate cancer: an immunohistochemical study," Hum. Pathol., 24(1):4-9.
U.S. Appl. No. 15/674,655 (Abandoned), filed Aug. 11, 2017, Kin-Ming Lo, Combination Therapy for Cancer.
U.S. Appl. No. 17/674,655, filed Jun. 24, 2021, Kin-Ming Lo, Combination Therapy for Cancer.
Arnau J, Lauritzen C, Petersen GE, Pedersen J. Current strategies for the use of affinity tags and tag removal for the purification of recombinant proteins. Protein Expr Purif. Jul. 2006;48(1):1-13.
Chen X, Zaro JL, Shen WC. Fusion protein linkers: property, design and functionality. Adv Drug Deliv Rev. Oct. 2013;65(10):1357-69.
Frankel AE, Ramage J, Kiser M, Alexander R, Kucera G, Miller MS. Characterization of diphtheria fusion proteins targeted to the human interleukin-3 receptor. Protein Eng. Aug. 2000;13(8):575-81.
Maeda Y, Ueda H, Kazami J, Kawano G, Suzuki E, Nagamune T. Engineering of functional chimeric protein G-Vargula luciferase. Anal Biochem. Jul. 1, 1997;249(2):147-52.

(56) References Cited

OTHER PUBLICATIONS

Muller S, Monneaux F, Schall N, Rashkov RK, Oparanov BA, Wiesel P, Geiger JM, Zimmer R. Spliceosomal peptide P140 for immunotherapy of systemic lupus erythematosus: results of an early phase II clinical trial. Arthritis Rheum. Dec. 2008;58(12):3873-83.

Pakula AA, Sauer RT. Genetic analysis of protein stability and function. Annu Rev Genet. 1989;23:289-310.

Pilones KA, Vanpouille-Box C, Demaria S. Combination of radiotherapy and immune checkpoint inhibitors. Semin Radiat Oncol. Jan. 2015;25(1):28-33.

Shen J, Vil MD, Jimenez X, Iacolina M, Zhang H, Zhu Z. Single variable domain-IgG fusion. A novel recombinant approach to Fc domain-containing bispecific antibodies. J Biol Chem. Apr. 21, 2006;281(16):10706-14.

Zhang et al. (2008) "Expression of a soluble TGF-beta receptor by tumor cells enhances dendritic cell/tumor fusion vaccine efficacy," J Immunol, 181(5):3690-7.

SEQUENCE LISTING

```
<160> NUMBER OF SEQ ID NOS: 49

<210> SEQ ID NO 1
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 2
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val

```
            35                  40                  45
Ser Ser Ile Tyr Pro Ser Gly Gly Ile Thr Phe Tyr Ala Asp Thr Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Lys Leu Gly Thr Val Thr Thr Val Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Ala Gly Gly Gly Ser Gly Gly Gly Ser Gly Gly Gly Gly
450                 455                 460
```

Ser Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
        515                 520                 525

Gln Glu Val Cys Val Ala Val Trp Arg Lys Asn Asp Glu Asn Ile Thr
    530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys
                565                 570                 575

Pro Gly Glu Thr Phe Phe Met Cys Ser Cys Ser Ser Asp Glu Cys Asn
                580                 585                 590

Asp Asn Ile Ile Phe Ser Glu Glu Tyr Asn Thr Ser Asn Pro Asp
        595                 600                 605

<210> SEQ ID NO 4
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgagggccc tgctggctag actgctgctg tgcgtgctgg tcgtgtccga cagcaagggc      60
cagtccgccc tgacccagcc tgcctccgtg tctggctccc ctggccagtc catcaccatc     120
agctgcaccg gcacctccag cgacgtgggc ggctacaact acgtgtcctg gtatcagcag     180
caccccggca aggcccccaa gctgatgatc tacgacgtgt ccaaccggcc ctccggcgtg     240
tccaacagat tctccggctc caagtccggc aacaccgcct ccctgaccat cagcggactg     300
caggcagagg acgaggccga ctactactgc tcctcctaca cctcctccag caccagagtg     360
ttcggcaccg gcacaaaagt gaccgtgctg ggccagccca aggccaaccc aaccgtgaca     420
ctgttccccc catcctccga ggaactgcag gccaacaagg ccaccctggt ctgcctgatc     480
tcagatttct atccaggcgc cgtgaccgtg gcctggaagg ctgatggctc cccagtgaag     540
gccggcgtgg aaaccaccaa gcctccaag cagtccaaca caaatacgc cgcctcctcc       600 tacctgtccc tgaccccga gcagtggaag tcccaccggt cctacagctg ccaggtcaca     660
cacgagggct ccaccgtgga aaagaccgtc gcccccaccg agtgctcatg a              711

<210> SEQ ID NO 5
<211> LENGTH: 1887
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggaaacag acaccctgct gctgtgggtg ctgctgctgt gggtgcccgg ctccacaggc      60
gaggtgcagc tgctggaatc cggcggagga ctggtgcagc ctggcggctc cctgagactg     120
tcttgcgccg cctccggctt caccttctcc agctacatca tgatgtgggt gcgacaggcc     180

```
cctggcaagg gcctggaatg ggtgtcctcc atctaccct ccggcggcat caccttctac    240
gccgacaccg tgaagggccg gttcaccatc tcccgggaca actccaagaa cacctgtac    300 ctgcagatga actccctgcg ggccgaggac accgccgtgt actactgcgc ccggatcaag    360
ctgggcaccg tgaccaccgt ggactactgg ggccagggca ccctggtgac agtgtcctcc    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctggggga    780 ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctccctgtc cccgggtgct ggcggcggag gaagcggagg aggtggcagc    1440
ggtggcggtg gctccggcgg aggtggctcc ggaatccctc cccacgtgca gaagtccgtg    1500
aacaacgaca tgatcgtgac cgacaacaac ggcgccgtga agttccctca gctgtgcaag    1560
ttctgcgacg tgaggttcag cacctgcgac aaccagaagt cctgcatgag caactgcagc    1620
atcacaagca tctgcgagaa gccccaggag gtgtgtgtgg ccgtgtggag gaagaacgac    1680
gaaaacatca ccctcgagac cgtgtgccat gaccccaagc tgccctacca cgacttcatc    1740
ctggaagacg ccgcctcccc caagtgcatc atgaaggaga gaagaagcc cggcgagacc    1800 ttcttcatgt gcagctgcag cagcgacgag tgcaatgaca acatcatctt tagcgaggag    1860
tacaacacca gcaaccccga ctgataa                                        1887
```

<210> SEQ ID NO 6
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 7
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ala Gly Gly Gly Ser Gly Gly Gly Ser Gly Gly Gly
    450                 455                 460

Ser Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
        515                 520                 525

Gln Glu Val Cys Val Ala Val Trp Arg Lys Asn Asp Glu Asn Ile Thr
    530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys Lys
                565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605
```

```
<210> SEQ ID NO 8
<211> LENGTH: 592
<212> TYPE: PRT
<213> ORGANISM: Homo sapiens

<400> SEQUENCE: 8

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380
```

```
His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
            405                 410                 415

Thr Cys Cys Leu Cys Asp Phe Gly Leu Ser Leu Arg Leu Asp Pro Thr
        420                 425                 430

Leu Ser Val Asp Asp Leu Ala Asn Ser Gly Gln Val Gly Thr Ala Arg
    435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
            485                 490                 495

Pro Pro Phe Gly Ser Lys Val Arg Glu His Pro Cys Val Glu Ser Met
        500                 505                 510

Lys Asp Asn Val Leu Arg Asp Arg Gly Arg Pro Glu Ile Pro Ser Phe
    515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
            565                 570                 575

Cys Ser Glu Glu Lys Ile Pro Glu Asp Gly Ser Leu Asn Thr Thr Lys
        580                 585                 590

<210> SEQ ID NO 9
<211> LENGTH: 567
<212> TYPE: PRT
<213> ORGANISM: Homo sapiens

<400> SEQUENCE: 9

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65              70                  75                  80

Gln Glu Val Cys Val Ala Val Trp Arg Lys Asn Asp Glu Asn Ile Thr
            85                  90                  95

Leu Glu Thr Val Cys His Asp Pro Lys Leu Pro Tyr His Asp Phe Ile
        100                 105                 110

Leu Glu Asp Ala Ala Ser Pro Lys Cys Ile Met Lys Glu Lys Lys Lys
    115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
```

```
                  165                 170                 175
Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
            210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
                275                 280                 285

Thr Glu Lys Asp Ile Phe Ser Asp Ile Asn Leu Lys His Glu Asn Ile
            290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
            370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
            530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 10
```

```
<211> LENGTH: 136
<212> TYPE: PRT
<213> ORGANISM: Homo sapiens

<400> SEQUENCE: 10

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Leu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Ser Gly Gly Gly Ser Gly
1               5                   10                  15

Gly Gly Gly Ser Gly
            20

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 15
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 15

Gln Phe Asn Ser
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ala Gln Ser
1

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Lys Ser Cys Asp Lys
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Lys Ser Ser Asp Lys
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ser Leu Ser
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Thr Ala Thr
1

```
<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg, Thr, Gln, Gly, Ala, Trp, Met, Ile or
      Ser
<220> FEATURE:
<221> NAME/KEY: MOD_RES
<222> LOCATION: (3)..(3)
<223> OTHER INFORMATION: Val, Arg, Lys, Leu, Met or Ile
<220> FEATURE:
<221> NAME/KEY: MOD_RES
<222> LOCATION: (5)..(5)
<223> OTHER INFORMATION: His, Thr, Asn, Gln, Ala, Val, Tyr, Trp, Phe or
      Met

<400> SEQUENCE: 21

Xaa Tyr Xaa Met Xaa
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phe or Ile
<220> FEATURE:
<221> NAME/KEY: MOD_RES
<222> LOCATION: (14)..(14)
<223> OTHER INFORMATION: Ser or Thr

<400> SEQUENCE: 22

Ser Ile Tyr Pro Ser Gly Gly Xaa Thr Phe Tyr Ala Asp Xaa Val Lys
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Glu or Asp

<400> SEQUENCE: 23

Ile Lys Leu Gly Thr Val Thr Thr Val Xaa Tyr
1               5                   10

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser
            20                  25                  30

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Val Arg Gln Ala Pro Gly Lys Gly Leu Glu Trp Val Ser
1               5                  10

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Arg
            20                  25                  30

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Gly Gln Gly Thr Leu Val Thr Val Ser Ser
1               5                  10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Ser
<220> FEATURE:
<221> NAME/KEY: MOD_RES
<222> LOCATION: (5)..(5)
<223> OTHER INFORMATION: Thr, Arg or Ser
<220> FEATURE:
<221> NAME/KEY: MOD_RES
<222> LOCATION: (9)..(9)
<223> OTHER INFORMATION: Ala or Gly

<400> SEQUENCE: 28

Thr Gly Thr Xaa Xaa Asp Val Gly Xaa Tyr Asn Tyr Val Ser
1               5                  10
```

```
<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (3)..(3)
<223> OTHER INFORMATION: Ile, Asn or Ser
<220> FEATURE:
<221> NAME/KEY: MOD_RES
<222> LOCATION: (4)..(4)
<223> OTHER INFORMATION: Asp, His or Asn

<400> SEQUENCE: 29

Xaa Val Xaa Xaa Arg Pro Ser
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe or Tyr
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(6)
<223> OTHER INFORMATION: Arg, Thr or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Ile or Thr

<400> SEQUENCE: 30

Ser Ser Xaa Thr Xaa Xaa Xaa Xaa Arg Val
1               5                   10

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 32
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Tyr Gln Gln His Pro Gly Lys Ala Pro Lys Leu Met Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Gly Thr Gly Thr Lys Val Thr Val Leu
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Tyr Ile Met Met
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ile Tyr Pro Ser Gly Gly Ile Thr Phe Tyr Ala Asp Thr Val Lys
1               5                   10                  15

Gly

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 37

Ile Lys Leu Gly Thr Val Thr Thr Val Asp Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Gly Thr Ser Ser Asp Val Gly Gly Tyr Asn Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Val Ser Asn Arg Pro Ser
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Tyr Thr Ser Ser Ser Thr Arg Val
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Tyr Met Met Met
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ile Tyr Pro Ser Gly Gly Ile Thr Phe Tyr Ala Asp Ser Val Lys
1               5                   10                  15

Gly

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Thr Gly Thr Ser Ser Asp Val Gly Ala Tyr Asn Tyr Val Ser
1               5                   10

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Val Trp Arg Gln Ala Pro Gly Lys Gly Leu Glu Trp Val
        35                  40                  45

Ser Ser Ile Tyr Pro Ser Gly Gly Ile Thr Phe Tyr Ala Asp Trp Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ile Lys Leu Gly Thr Val Thr Thr Val Asp Tyr Trp Gly Gln Gly
            100                 105                 110

Thr Leu Val Thr Val Ser Ser
        115

<210> SEQ ID NO 45
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu

-continued

```
                100                 105                 110
```

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Met Trp Val Arg Gln Ala Pro Gly Lys Gly Leu Glu Val Trp
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120
```

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 48
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide from human Fab library

<400> SEQUENCE: 48

```
atggagttgc ctgttaggct gttggtgctg atgttctgga ttcctgctag ctccagcgag    60
gtgcagctgc tggaatccgg cggaggactg gtgcagcctg gcggctccct gagactgtct   120
tgcgccgcct ccggcttcac cttctccagc tacatcatga tgtgggtgcg acaggcccct   180
ggcaagggcc tggaatgggt gtcctccatc taccccctcc gcggcatcac cttctacgcc   240
gacaccgtga agggccggtt caccatctcc cgggacaact ccaagaacac cctgtacctg   300
cagatgaact ccctgcgggc cgaggacacc gccgtgtact actgcgcccg gatcaagctg   360
ggcaccgtga ccaccgtgga ctactggggc cagggcaccc tggtgacagt gtcctccgcc   420
tccaccaagg gcccatcggt cttccccctg gcacctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcacg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctatagc aagctcaccg tggacaagag caggtggcag  1320
caggggaacg tcttctcatg ctccgtgatg catgaggctc tgcacaacca ctacacgcag  1380
aagagcctct ccctgtcccc gggtaaa                                       1407
```

<210> SEQ ID NO 49
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide from human Fab library

<400> SEQUENCE: 49

```
atggagttgc ctgttaggct gttggtgctg atgttctgga ttcctgcttc cttaagccag    60
tccgccctga cccagcctgc ctccgtgtct ggctcccctg gccagtccat caccatcagc   120
tgcaccggca cctccagcga cgtgggcggc tacaactacg tgtcctggta tcagcagcac   180
cccggcaagg cccccaagct gatgatctac gacgtgtcca accggccctc cggcgtgtcc   240
aacagattct ccggctccaa gtccggcaac accgcctccc tgaccatcag cggactgcag   300
gcagaggacg aggccgacta ctactgctcc tcctacacct cctccagcac cagagtgttc   360
ggcaccggca aaaagtgac cgtgctgggc cagcccaagg ccaacccaac cgtgacactg   420 ttcccccat cctccgagga actgcaggcc aacaaggcca ccctggtctg cctgatctca   480
gatttctatc caggcgccgt gaccgtggcc tggaaggctg atggctcccc agtgaaggcc   540
ggcgtggaaa ccaccaagcc ctccaagcag tccaacaaca aatacgccgc ctcctcctac   600
```

```
ctgtccctga ccccgagca gtggaagtcc caccggtcct acagctgcca ggtcacacac      660
gagggctcca ccgtggaaaa gaccgtcgcc cccaccgagt gctca                    705
```

TARGETED TGFβ INHIBITION

CROSS REFERENCE TO RELATED APPLICATIONS

This application is a continuation of U.S. patent application Ser. No. 15/617,876, filed Jun. 8, 2017, which is a continuation of U.S. patent application Ser. No. 14/618,454, filed Feb. 10, 2015, now U.S. Pat. No. 9,676,863, which claims priority to and the benefit of U.S. Provisional Patent Application No. 61/938,048, filed Feb. 10, 2014, the disclosures of each of which are incorporated herein by reference in their entireties.

FIELD OF THE INVENTION

This invention relates generally to bifunctional molecules including (a) a TGFβRII or fragment thereof capable of binding TGFβ and (b) an antibody, or antigen binding fragment thereof, that binds to an immune checkpoint protein, such as Programmed Death Ligand 1 (PD-L1), uses of such molecules (e.g., for treating cancer), and methods of making such molecules.

BACKGROUND

In cancer treatment, it has long been recognized that chemotherapy is associated with high toxicity and can lead to emergence of resistant cancer cell variants. Even with targeted therapy against overexpressed or activated oncoproteins important for tumor survival and growth, cancer cells invariably mutate and adapt to reduce dependency on the targeted pathway, such as by utilizing a redundant pathway. Cancer immunotherapy is a new paradigm in cancer treatment that instead of targeting cancer cells, focuses on the activation of the immune system. Its principle is to rearm the host's immune response, especially the adaptive T cell response, to provide immune surveillance to kill the cancer cells, in particular, the minimal residual disease that has escaped other forms of treatment, hence achieving long-lasting protective immunity.

FDA approval of the anti-CTLA-4 antibody ipilimumab for the treatment of melanoma in 2011 ushered in a new era of cancer immunotherapy. The demonstration that anti-PD-1 or anti-PD-L1 therapy induced durable responses in melanoma, kidney, and lung cancer in clinical trials further signify its coming of age (Pardoll, D. M., Nat Immunol. 2012; 13:1129-32). However, ipilimumab therapy is limited by its toxicity profile, presumably because anti-CTLA-4 treatment, by interfering with the primary T cell inhibitory checkpoint, can lead to the generation of new autoreactive T cells. While inhibiting the PD-L1/PD-1 interaction results in dis-inhibiting existing chronic immune responses in exhausted T cells that are mostly antiviral or anticancer in nature (Wherry, E. J., Nat Immunol. 2011; 12:492-9), anti-PD-1 therapy can nevertheless sometimes result in potentially fatal lung-related autoimmune adverse events. Despite the promising clinical activities of anti-PD1 and anti-PD-L1 so far, increasing the therapeutic index, either by increasing therapeutic activity or decreasing toxicity, or both, remains a central goal in the development of immunotherapeutics.

SUMMARY OF THE INVENTION

The present invention is based on the discovery that a bifunctional protein containing at least portion of TGFβ Receptor II (TGFβRII) that is capable of binding TGFβ and antibody or antigen-binding fragment that binds to an immune checkpoint protein such as human protein Programmed Death Ligand 1 (PD-L1) can be an effective anti-tumor and anti-cancer therapeutic. The protein can exhibit a synergistic effect in cancer treatment, as compared to the effect of administering the two agents separately.

Accordingly, in a first aspect, the present invention features a protein including (a) human TGFβRII, or a fragment thereof capable of binding TGFβ (e.g., a soluble fragment); and (b) an antibody, or an antigen-binding fragment thereof, that binds PD-L1 (e.g., any of the antibodies or antibody fragments described herein).

In a related aspect, the invention features a polypeptide including (a) at least a variable domain of a heavy chain of an antibody that binds PD-L1 (e.g., amino acids 1-120 of SEQ ID NO: 2); and (b) human TGFβRII, or a soluble fragment thereof capable of binding TGFβ (e.g., a human TGFβRII extra-cellular domain (ECD), amino acids 24-159 of SEQ ID NO: 9, or any of those described herein). The polypeptide may further include an amino acid linker connecting the C-terminus of the variable domain to the N-terminus of the human TGFβRII or soluble fragment thereof capable of binding TGFβ. The polypeptide may include the amino acid sequence of SEQ ID NO: 3 or an amino acid sequence substantially identical to SEQ ID NO: 3. The antibody fragment may be an scFv, Fab, F(ab')$_2$, or Fv fragment.

In certain embodiments, the protein or polypeptide includes an antibody or antigen-binding fragment thereof that includes SEQ ID NO: 2 and human TGFβRII. The antibody may optionally include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 2 and a fragment of human TGFβRII capable of binding TGFβ (e.g., a soluble fragment). The antibody may optionally include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 2 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes amino acids 1-120 of SEQ ID NO: 2 and human TGFβRII. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes amino acids 1-120 of SEQ ID NO: 2 and a fragment of human TGFβRII capable of binding TGFβ (e.g., a soluble fragment). The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes amino acids 1-120 of SEQ ID NO: 2 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 2 and human TGFβRII. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 2 and a fragment of human TGFβRII capable of binding TGFβ (e.g., a soluble fragment). The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 2 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 12 and human TGFβRII. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 12 and a fragment of human TGFβRII capable of binding TGFβ (e.g., a soluble fragment). The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 12 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 12 and human TGFβRII. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 12 and a fragment of human TGFβRII capable of binding TGFβ (e.g., a soluble fragment). The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes the hypervariable regions present in SEQ ID NO: 12 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 14 and human TGFβRII. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 14 and a fragment of human TGFβRII capable of binding TGFβ (e.g., a soluble fragment). The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

In certain embodiments, the protein or polypeptide includes an antibody or antigen-binding fragment thereof that includes SEQ ID NO: 14 and a human TGFβRII ECD. The antibody may include a modified constant region (e.g., any described herein, including a C-terminal Lys→Ala substitution, a mutation of the Leu-Ser-Leu-Ser (SEQ ID NO: 19) sequence to Ala-Thr-Ala-Thr (SEQ ID NO: 20), or a hybrid constant region including an IgG1 hinge region and an IgG2 CH2 domain).

The invention also features a nucleic acid that includes a nucleotide sequence that encodes a polypeptide described above. In certain embodiments, the nucleic acid further includes a second nucleotide sequence encoding at least a variable domain of a light chain of an antibody which, when combined with the polypeptide, forms an antigen-binding site that binds PD-L1 (e.g., including amino acids 1-110 of SEQ ID NO: 1). The second nucleotide sequence may encode the amino acid sequence of SEQ ID NO: 1 (secreted anti-PD-L1 lambda light chain) or an amino acid sequence substantially identical to SEQ ID NO: 1. The invention also features a cell including any of the nucleic acids described above.

The invention also features a method of producing a protein including (a) the extracellular domain of the human TGFβRII, or a fragment thereof capable of binding TGFβ (e.g., a soluble fragment), and (b) an antibody, or an antigen-binding fragment thereof, that binds human PD-L1. The method includes maintaining a cell described under conditions that permit expression of the protein. The method may further include harvesting the protein.

The invention also features a protein including the polypeptide described above and at least a variable domain of a light chain of an antibody which, when combined with the polypeptide, forms an antigen-binding site that binds PD-L1. The protein may include (a) two polypeptides, each having an amino acid sequence consisting of the amino acid sequence of SEQ ID NO: 3, and (b) two additional polypeptides each having an amino acid sequence consisting of the amino acid sequence of SEQ ID NO: 1.

The invention also features a protein described above for use in therapy. The therapy may include administration of radiation or administration of a chemotherapeutic, a biologic, or a vaccine.

The invention also features a protein described above for use in promoting local depletion of TGFβ at a tumor.

The invention also features a protein described above for use in inhibiting SMAD3 phosphorylation in a cell (e.g., a tumor cell or an immune cell).

The invention also features a protein described above for use in treating cancer or for use in inhibiting tumor growth. The cancer or tumor may be selected from the group consisting of colorectal, breast, ovarian, pancreatic, gastric, prostate, renal, cervical, myeloma, lymphoma, leukemia, thyroid, endometrial, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, and myelodisplastic syndromes. The use may further include administration of radiation or administration of a chemotherapeutic, a biologic, or a vaccine.

The invention also features a method of promoting local depletion of TGFβ. The method includes administering a protein described above, where the protein binds TGFβ in solution, binds PD-L1 on a cell surface, and carries the bound TGFβ into the cell (e.g., a cancer cell).

The invention also features a method of inhibiting SMAD3 phosphorylation in a cell (e.g., a cancer cell or an immune cell), the method including exposing the cell in the tumor microenvironment to a protein described above.

The invention also features a method of inhibiting tumor growth or treating cancer. The method includes exposing the tumor to a protein described above. The method may further include exposing the tumor to radiation or to a chemotherapeutic, a biologic, or a vaccine. In certain embodiments, the tumor or cancer is selected from the group consisting of colorectal, breast, ovarian, pancreatic, gastric, prostate, renal, cervical, myeloma, lymphoma, leukemia, thyroid, endometrial, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, and myelodisplastic syndromes.

By "TGFβRII" or "TGFβ Receptor II" is meant a polypeptide having the wild-type human TGFβ Receptor Type 2 Isoform A sequence (e.g., the amino acid sequence of NCBI Reference Sequence (RefSeq) Accession No. NP_001020018 (SEQ ID NO: 8)), or a polypeptide having the wild-type human TGFβ Receptor Type 2 Isoform B sequence (e.g., the amino acid sequence of NCBI RefSeq Accession No. NP_003233 (SEQ ID NO: 9)) or having a sequence substantially identical the amino acid sequence of SEQ ID NO: 8 or of SEQ ID NO: 9. The TGFβRII may retain at least 0.1%, 0.5%, 1%, 5%, 10%, 25%, 35%, 50%, 75%, 90%, 95%, or 99% of the TGFβ-binding activity of the wild-type sequence. The polypeptide of expressed TGFβRII lacks the signal sequence.

By a "fragment of TGFβRII capable of binding TGFβ" is meant any portion of NCBI RefSeq Accession No. NP_001020018 (SEQ ID NO: 8) or of NCBI RefSeq Accession No. NP 003233 (SEQ ID NO: 9), or a sequence substantially identical to SEQ ID NO: 8 or SEQ ID NO: 9 that is at least 20 (e.g., at least 30, 40, 50, 60, 70, 80, 90, 100, 110, 120, 130, 140, 150, 160, 175, or 200) amino acids in length that retains at least some of the TGFβ-binding activity (e.g., at least 0.1%, 0.5%, 1%, 5%, 10%, 25%, 35%, 50%, 75%, 90%, 95%, or 99%) of the wild-type receptor or of the corresponding wild-type fragment. Typically such fragment is a soluble fragment. An exemplary such fragment is a TGFβRII extra-cellular domain having the sequence of SEQ ID NO: 10.

By "substantially identical" is meant a polypeptide exhibiting at least 50%, desirably 60%, 70%, 75%, or 80%, more desirably 85%, 90%, or 95%, and most desirably 99% amino acid sequence identity to a reference amino acid sequence. The length of comparison sequences will generally be at least 10 amino acids, desirably at least 15 contiguous amino acids, more desirably at least 20, 25, 50, 75, 90, 100, 150, 200, 250, 300, or 350 contiguous amino acids, and most desirably the full-length amino acid sequence.

By "patient" is meant either a human or non-human animal (e.g., a mammal).

By "treating" a disease, disorder, or condition (e.g., a cancer) in a patient is meant reducing at least one symptom of the disease, disorder, or condition by administrating a therapeutic agent to the patient.

By "cancer" is meant a collection of cells multiplying in an abnormal manner.

Other embodiments and details of the invention are presented herein below.

BRIEF DESCRIPTION OF THE DRAWINGS

FIG. 7A shows tumor growth curves of average tumor volumes of surviving mice in different treatment groups (star: Group 1: filled circle: Group 2; filled triangle: Group 3; filled square: Group 4; open square: Group 5; filled square/dashed line: Group 6; filled square/stippled line: Group 7). FIG. 7B shows tumor growth curves of individual tumor volumes in different treatment groups. FIG. 7C is a Kaplan-Meier plot of percent survival in different treatment groups (symbols as in 7A).

FIG. 12A shows tumor growth curves of mice treated with both intermediate and low doses of the proteins (star: Group 1; filled squares: Group 2; open squares: Group 3; filled diamonds: Group 4; open diamonds Group 5). FIG. 12B (star: Group 1; filled square: Group 2; filled diamond: Group 4; *: p<0.0001 compared to Group 1; **: p<0.0001 compared to Group 2) and 12C (star: Group 1; filled square: Group 2; filled diamond: Group 3; filled diamond: Group 5; *: p<0.0001 compared to Group 1; **: p<0.0001 compared to Group 3) show statistical analysis of tumor growth curves of mice treated with intermediate and low doses of the proteins, respectively FIG. 13A shows tumor growth curves of mice in different treatment groups. FIG. 13B is a Kaplan-Meier plot of percent survival in different treatment groups.

DETAILED DESCRIPTION

Figure 1A:
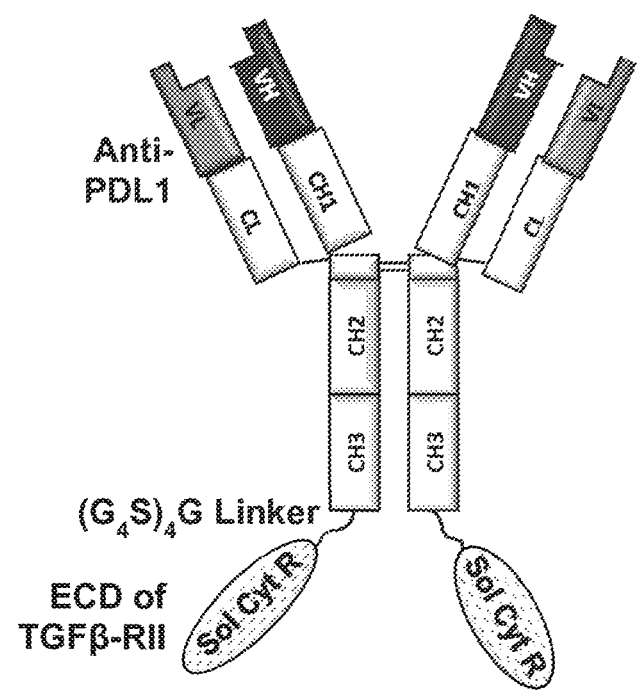
FIG. 1A is a schematic drawing of an anti-PD-L1/TGFβ Trap molecule comprising one anti-PD-L1 antibody fused to two extracellular domain (ECD) of TGFβ Receptor II via a (Gly$_4$Ser)$_4$Gly linker (SEQ ID NO: 11).

The current invention permits localized reduction in TGFβ in a tumor microenvironment by capturing the TGFβ using a soluble cytokine receptor (TGFβRII) tethered to an antibody moiety targeting a cellular immune checkpoint receptor found on the exterior surface of certain tumor cells or immune cells. An example of an antibody moiety of the invention to an immune checkpoint protein is anti-PD-L1. This bifunctional molecule, sometimes referred to in this document as an "antibody-cytokine trap," is effective precisely because the anti-receptor antibody and cytokine trap are physically linked. The resulting advantage (over, for example, administration of the antibody and the receptor as separate molecules) is partly because cytokines function predominantly in the local environment through autocrine and paracrine functions. The antibody moiety directs the cytokine trap to the tumor microenvironment where it can be most effective, by neutralizing the local immunosuppressive autocrine or paracrine effects. Furthermore, in cases where the target of the antibody is internalized upon antibody binding, an effective mechanism for clearance of the cytokine/cytokine receptor complex is provided. Antibody-mediated target internalization has been shown for PD-L1. This is a distinct advantage over using an anti-TGFβ antibody because first, an anti-TGFβ antibody might not be completely neutralizing; and second, the antibody can act as a carrier extending the half-life of the cytokine, and antibody/cytokine complexes often act as a circulating sink that builds up and ultimately dissociates to release the cytokine back in circulation (Montero-Julian et al., Blood. 1995; 85:917-24). The use of a cytokine trap to neutralize the ligand can also be a better strategy than blockading the receptor with an antibody, as in the case of CSF-1. Because CSF-1 is cleared from the circulation by receptor-mediated endocytosis, an anti-CSF-1 receptor antibody blockade caused a significant increase in circulating CSF-1 concentration (Hume et al., Blood. 2012; 119:1810-20)

Indeed, as described below, treatment with the anti-PD-L1/TGFβ Trap elicits a synergistic anti-tumor effect due to the simultaneous blockade of the interaction between PD-L1 on tumor cells and PD-1 on immune cells, and the neutralization of TGFβ in the tumor microenvironment. As demonstrated in the following examples, anti-PDL1/TGFβ Trap has efficacy superior to that of the single agent anti-PD-L1 or TGFβ Trap control. Without being bound by theory, this presumably is due to a synergistic effect obtained from simultaneous blocking the two major immune escape mechanisms, and in addition, the targeted depletion of the TGFβ in the tumor microenvironment by a single molecular entity. This depletion is achieved by (1) anti-PD-L1 targeting of tumor cells; (2) binding of the TGFβ autocrine/paracrine in the tumor microenvironment by the TGFβ Trap; and (3) destruction of the bound TGFβ through the PD-L1 receptor-mediated endocytosis. The aforementioned mechanisms of action cannot be achieved by the combination therapy of the two single agents anti-PD-L1 and TGFβ Trap. Furthermore, the TGFβRII fused to the C-terminus of Fc (fragment of crystallization of IgG) was several-fold more potent than the TGFβRII-Fc that places the TGFβRII at the N-terminus of Fc (see Example 3). The superb efficacy obtained with anti-PDL1/TGFβ Trap also allays some concerns that the TGFβRII does not trap TGFβ2. As pointed out by Yang et al., Trends Immunol. 2010; 31:220-227, although some tumor types do secrete TGFβ2 initially, as the tumor progresses, the TGFβ in the tumor microenvironment is predominantly secreted by myeloid-derived suppressor cells, which secrete TGFβ1. In addition to showing great promise as an effective immuno-oncology therapeutic, treatment with soluble TGFβRII can potentially reduce the cardiotoxicity concerns of TGFβ targeting therapies, especially the TGFβRI kinase inhibitors. This is because of the important roles TGFβ2 plays in embryonic development of the heart as well as in repair of myocardial damage after ischemia and reperfusion injury (Roberts et al., J Clin Invest. 1992; 90:2056-62).

TGFβ as a Cancer Target

TGFβ had been a somewhat questionable target in cancer immunotherapy because of its paradoxical roles as the molecular Jekyll and Hyde of cancer (Bierie et al., Nat Rev Cancer. 2006; 6:506-20). Like some other cytokines, TGFβ activity is developmental stage and context dependent. Indeed TGFβ can act as either a tumor promoter or a tumor suppressor, affecting tumor initiation, progression and metastasis. The mechanisms underlying this dual role of TGFβ remain unclear (Yang et al., Trends Immunol. 2010; 31:220-227). Although it has been postulated that Smad-dependent signaling mediates the growth inhibition of TGFβ signaling, while the Smad independent pathways contribute to its tumor-promoting effect, there are also data showing that the Smad-dependent pathways are involved in tumor progression (Yang et al., Cancer Res. 2008; 68:9107-11).

Both the TGFβ ligand and the receptor have been studied intensively as therapeutic targets. There are three ligand isoforms, TGFβ1, 2 and 3, all of which exist as homodimers. There are also three TGFβ receptors (TGFβR), which are called TGFβR type I, II and III (López-Casillas et al., J Cell Biol. 1994; 124:557-68). TGFβRI is the signaling chain and cannot bind ligand. TGFβRII binds the ligand TGFβ1 and 3, but not TGFβ2, with high affinity. The TGFβRII/TGFβ complex recruits TGFβRI to form the signaling complex (Won et al., Cancer Res. 1999; 59:1273-7). TGFβRIII is a positive regulator of TGFβ binding to its signaling receptors and binds all 3 TGFβ isoforms with high affinity. On the cell surface, the TGFβ/TGFβRIII complex binds TGFβRII and then recruits TGFβRI, which displaces TGFβRIII to form the signaling complex.

Although the three different TGFβ isoforms all signal through the same receptor, they are known to have differential expression patterns and non-overlapping functions in vivo. The three different TGF-3 isoform knockout mice have distinct phenotypes, indicating numerous non-compensated functions (Bujak et al., Cardiovasc Res. 2007; 74:184-95). While TGFβ1 null mice have hematopoiesis and vasculogenesis defects and TGFβ3 null mice display pulmonary development and defective palatogenesis, TGFβ2 null mice show various developmental abnormalities, the most prominent being multiple cardiac deformities (Bartram et al., Circulation. 2001; 103:2745-52; Yamagishi et al., Anat Rec. 2012; 295:257-67). Furthermore, TGFβ is implicated to play a major role in the repair of myocardial damage after ischemia and reperfusion injury. In an adult heart, cardiomyocytes secrete TGFβ, which acts as an autocrine to maintain the spontaneous beating rate. Importantly, 70-85% of the TGFβ secreted by cardiomyocytes is TGFβ2 (Roberts et al., J Clin Invest. 1992; 90:2056-62). In summary, given the predominant roles of TGFβ1 and TGFβ2 in the tumor microenvironment and cardiac physiology, respectively, a therapeutic agent that neutralizes TGFβ1 but not TGFβ2 could provide an optimal therapeutic index by minimizing the cardiotoxicity without compromising the anti-tumor activity. This is consistent with the findings by the present inventors, who observed a lack of toxicity, including cardiotoxicity, for anti-PD-L1/TGFβ Trap in monkeys.

Therapeutic approaches to neutralize TGFβ include using the extracellular domains of TGFβ receptors as soluble receptor traps and neutralizing antibodies. Of the receptor trap approach, soluble TGFβRIII may seem the obvious choice since it binds all the three TGFβ ligands. However, TGFβRIII, which occurs naturally as a 280-330 kD glucosaminoglycan (GAG)-glycoprotein, with extracellular domain of 762 amino acid residues, is a very complex protein for biotherapeutic development. The soluble TGFβRIII devoid of GAG could be produced in insect cells and shown to be a potent TGFβ neutralizing agent (Vilchis-Landeros et al, Biochem J 355:215, 2001). The two separate binding domains (the endoglin-related and the uromodulin-related) of TGFβRIII could be independently expressed, but they were shown to have affinities 20 to 100 times lower than that of the soluble TGFβRIII, and much diminished neutralizing activity (Mendoza et al., Biochemistry. 2009; 48:11755-65). On the other hand, the extracellular domain of TGFβRII is only 136 amino acid residues in length and can be produced as a glycosylated protein of 25-35 kD. The recombinant soluble TGFβRII was further shown to bind TGFβ1 with a $K_D$ of 200 pM, which is fairly similar to the $K_D$ of 50 pM for the full length TGFβRII on cells (Lin et al., J Biol Chem. 1995; 270:2747-54). Soluble TGFβRII-Fc was tested as an anti-cancer agent and was shown to inhibit established murine malignant mesothelioma growth in a tumor model (Suzuki et al., Clin Cancer Res. 2004; 10:5907-18). Since TGFβRII does not bind TGFβ2, and TGFβRIII binds TGFβ1 and 3 with lower affinity than TGFβRII, a fusion protein of the endoglin domain of TGFβRIII and extracellular domain of TGFβRII was produced in bacteria and was shown to inhibit the signaling of TGFβ1 and 2 in cell based assays more effectively than either TGFβRII or RIII (Verona et al., Protein Eng Des Sel. 2008; 21:463-73). Despite some encouraging anti-tumor activities in tumor models, to our knowledge no TGFβ receptor trap recombinant proteins have been tested in the clinic.

Still another approach to neutralize all three isoforms of the TGFβ ligands is to screen for a pan-neutralizing anti-TGFβ antibody, or an anti-receptor antibody that blocks the receptor from binding to TGFβ1, 2 and 3. GC1008, a human antibody specific for all isoforms of TGFβ, was in a Phase I/II study in patients with advanced malignant melanoma or renal cell carcinoma (Morris et al., J Clin Oncol 2008; 26:9028 (Meeting abstract)). Although the treatment was found to be safe and well tolerated, only limited clinical efficacy was observed, and hence it was difficult to interpret the importance of anti-TGFβ therapy without further characterization of the immunological effects (Flavell et al., Nat Rev Immunol. 2010; 10:554-67). There were also TGFβ-isoform-specific antibodies tested in the clinic. Metelimumab, an antibody specific for TGFβ1 was tested in Phase 2 clinical trial as a treatment to prevent excessive postoperative scarring for glaucoma surgery; and Lerdelimumab, an antibody specific for TGFβ2, was found to be safe but ineffective at improving scarring after eye surgery in a Phase 3 study (Khaw et al., Ophthalmology 2007; 114:1822-1830). Anti-TGFβRII antibodies that block the receptor from binding to all three TGFβ isoforms, such as the anti-human TGFβRII antibody TR1 and anti-mouse TGFβRII antibody MT1, have also shown some therapeutic efficacy against primary tumor growth and metastasis in mouse models (Zhong et al., Clin Cancer Res. 2010; 16:1191-205). To date, the vast majority of the studies on TGFβ targeted anticancer treatment, including small molecule inhibitors of TGFβ signaling that often are quite toxic, are mostly in the preclinical stage and the anti-tumor efficacy obtained has been limited (Calone et al., Exp Oncol. 2012; 34:9-16; Connolly et al., Int J Biol Sci. 2012; 8:964-78).

The antibody-TGFβ trap of the invention is a bifunctional protein containing at least portion of a human TGFβ Receptor II (TGFβRII) that is capable of binding TGFβ. In one embodiment, the TGFβ trap polypeptide is a soluble portion of the human TGFβ Receptor Type 2 Isoform A (SEQ ID NO: 8) that is capable of binding TGFβ. In a further embodiment, TGFβ trap polypeptide contains at least amino acids 73-184 of SEQ ID NO:8. In yet a further embodiment, the TGFβ trap polypeptide contains amino acids 24-184 of SEQ ID NO:8. In another embodiment, the TGFβ trap polypeptide is a soluble portion of the human TGFβ Receptor Type 2 Isoform B (SEQ ID NO: 9) that is capable of binding TGFβ. In a further embodiment, TGFβ trap polypeptide contains at least amino acids 48-159 of SEQ ID NO:9. In yet a further embodiment, the TGFβ trap polypeptide contains amino acids 24-159 of SEQ ID NO:9. In yet a further embodiment, the TGFβ trap polypeptide contains amino acids 24-105 of SEQ ID NO:9.

Immune Checkpoint Dis-Inhibition

The approach of targeting T cell inhibition checkpoints for dis-inhibition with therapeutic antibodies is an area of intense investigation (for a review, see Pardoll, Nat Rev Cancer. 2012; 12:253-264). In one approach, the antibody moiety or antigen binding fragment thereof targets T cell inhibition checkpoint receptor proteins on the T cell, such as, for example: CTLA-4, PD-1, BTLA, LAG-3, TIM-3, and LAIR1. In another approach, the antibody moiety targets the counter-receptors on antigen presenting cells and tumor cells (which co-opt some of these counter-receptors for their own immune evasion), such as, for example: PD-L1 (B7-H1), B7-DC, HVEM, TIM-4, B7-H3, or B7-H4.

The invention contemplates antibody TGFβ traps that target, through their antibody moiety or antigen binding fragment thereof, T cell inhibition checkpoints for dis-inhibition. To that end the present inventors have tested the anti-tumor efficacy of combining a TGFβ trap with antibodies targeting various T cell inhibition checkpoint receptor proteins, such as anti-PD-1, anti-PD-L1, anti-TIM-3 and anti-LAG3. The experimental results are further detailed in Examples 7-18. The present inventors found that combining a TGFβ trap with an anti-PD-L1 antibody exhibited remarkable anti-tumor activity beyond what was observed with the monotherapies. In contrast, none of the other combinations with antibodies to the targets listed above showed any superior efficacy. In particular, one may have expected that a combination treatment of a TGFβ trap with an anti-PD-1 antibody would demonstrate similar activity to the one observed with anti-PD-L1, as PD-1/PD-L1 are cognate receptors that bind to each other to effect the immune checkpoint inhibition. However, this is not what the present inventors have found.

Anti-PD-L1 Antibodies

The invention can include any anti-PD-L1 antibody, or antigen-binding fragment thereof, described in the art. Anti-PD-L1 antibodies are commercially available, for example, the 29E2A3 antibody (Biolegend, Cat. No. 329701). Antibodies can be monoclonal, chimeric, humanized, or human. Antibody fragments include Fab, F(ab')2, scFv and Fv fragments, which are described in further detail below.

Exemplary antibodies are described in PCT Publication WO 2013/079174. These antibodies can include a heavy chain variable region polypeptide including an HVR-H1, HVR-H2, and HVR-H3 sequence, where:

(a) the HVR-H1 sequence is $X_1YX_2MX_3$ (SEQ ID NO: 21);
(b) the HVR-H2 sequence is SIYPSGGX$_4$TFYADX$_5$VKG (SEQ ID NO: 22);
(c) the HVR-H3 sequence is IKLGTVTTVX$_6$Y (SEQ ID NO: 23);

further where: $X_1$ is K, R, T, Q, G, A, W, M, I, or S; $X_2$ is V, R, K, L, M, or I; $X_3$ is H, T, N, Q, A, V, Y, W, F, or M; $X_4$ is F or I; $X_5$ is S or T; $X_6$ is E or D.

In a one embodiment, $X_1$ is M, I, or S; $X_2$ is R, K, L, M, or I; $X_3$ is F or M; $X_4$ is F or I; $X_5$ is S or T; $X_6$ is E or D.

In another embodiment $X_1$ is M, I, or S; $X_2$ is L, M, or I; $X_3$ is F or M; $X_4$ is I; $X_5$ is S or T; $X_6$ is D.

In still another embodiment, $X_1$ is S; $X_2$ is I; $X_3$ is M; $X_4$ is I; $X_5$ is T; $X_6$ is D.

In another aspect, the polypeptide further includes variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4).

In yet another aspect, the framework sequences are derived from human consensus framework sequences or human germline framework sequences.

In a still further aspect, at least one of the framework sequences is the following:

```
HC-FR1 is EVQLLESGGGLVQPGGSLRLSCAASGFTFS (SEQ ID NO: 24);

HC-FR2 is WVRQAPGKGLEWVS (SEQ ID NO: 25);

HC-FR3 is RFTISRDNSKNTLYLQMNSLRAEDTAVYYCAR
(SEQ ID NO: 26);

HC-FR4 is WGQGTLVTVSS (SEQ ID NO: 27).
```

In a still further aspect, the heavy chain polypeptide is further combined with a variable region light chain including an HVR-L1, HVR-L2, and HVR-L3, where:
  (a) the HVR-L1 sequence is TGTX$_7$X$_8$DVGX$_9$YNYVS (SEQ ID NO: 28);
  (b) the HVR-L2 sequence is X$_{10}$VX$_{11}$X$_{12}$RPS (SEQ ID NO: 29);
  (c) the HVR-L3 sequence is SSX$_{13}$TX$_{14}$X$_{15}$X$_{16}$X$_{17}$RV (SEQ ID NO: 30);
further where: X$_7$ is N or S; X$_8$ is T, R, or S; X$_9$ is A or G; X$_{10}$ is E or D; X$_{11}$ is I, N or S; X$_{12}$ is D, H or N; X$_{13}$ is F or Y; X$_{14}$ is N or S; X$_{15}$ is R, T or S; X$_{16}$ is G or S; X$_{17}$ is I or T.

In another embodiment, X$_7$ is N or S; X$_8$ is T, R, or S; X$_9$ is A or G; X$_{10}$ is E or D; X$_{11}$ is N or S; X$_{12}$ is N; X$_{13}$ is F or Y; X$_{14}$ is S; X$_{15}$ is S; X$_{16}$ is G or S; X$_{17}$ is T.

In still another embodiment, X$_7$ is S; X$_8$ is S; X$_9$ is G; X$_{10}$ is D; X$_{11}$ is S; X$_{12}$ is N; X$_{13}$ is Y; X$_{14}$ is S; X$_{15}$ is S; X$_{16}$ is S; X$_{17}$ is T.

In a still further aspect, the light chain further includes variable region light chain framework sequences juxtaposed between the HVRs according to the formula: (LC-FR1MHVR-L1)-(LC-FR2)-(HVR-L2)-(LC-FR3)-(HVR-L3)-(LC-FR4).

In a still further aspect, the light chain framework sequences are derived from human consensus framework sequences or human germline framework sequences.

In a still further aspect, the light chain framework sequences are lambda light chain sequences.

In a still further aspect, at least one of the framework sequence is the following:

```
LC-FR1 is QSALTQPASVSGSPGQSITISC (SEQ ID NO: 31);

LC-FR2 is WYQQHPGKAPKLMIY (SEQ ID NO: 32);

LC-FR3 is GVSNRFSGSKSGNTASLTISGLQAEDEADYYC
(SEQ ID NO: 33);

LC-FR4 is FGTGTKVTVL (SEQ ID NO: 34).
```

In another embodiment, the invention provides an anti-PD-L1 antibody or antigen binding fragment including a heavy chain and a light chain variable region sequence, where:
  (a) the heavy chain includes an HVR-H1, HVR-H2, and HVR-H3, wherein further: (i) the HVR-H1 sequence is X$_1$YX$_2$MX$_3$ (SEQ ID NO: 21); (ii) the HVR-H2 sequence is SIYPSGGX$_4$TFYADX$_5$VKG (SEQ ID NO: 22); (iii) the HVR-H3 sequence is IKLGTVTTVX$_6$Y (SEQ ID NO: 23), and;
  (b) the light chain includes an HVR-L1, HVR-L2, and HVR-L3, wherein further: (iv) the HVR-L1 sequence is TGTX$_7$X$_8$DVGX$_9$YNYVS (SEQ ID NO: 28); (v) the HVR-L2 sequence is X$_{10}$VX$_{11}$X$_{12}$RPS (SEQ ID NO: 29); (vi) the HVR-L3 sequence is SSX$_{13}$TX$_{14}$X$_{15}$X$_{16}$X$_{17}$RV (SEQ ID NO: 30); wherein: X$_1$ is K, R, T, Q, G, A, W, M, I, or S; X$_2$ 1S V, R, K, L, M, or I; X$_3$ is H, T, N, Q, A, V, Y, W, F, or M; X$_4$ is F or I; X$_5$ is S or T; X$_6$ is E or D; X$_7$ is N or S; X$_8$ is T, R, or S; X$_9$ is A or G; X$_{10}$ is E or D; X$_{11}$ is I, N, or S; X$_{12}$ is D, H, or N; X$_{13}$ is F or Y; X$_{14}$ is N or S; X$_{15}$ is R, T, or S; X$_{16}$ is G or S; X$_{17}$ is I or T.

In one embodiment, X$_1$ is M, I, or S; X$_2$ is R, K, L, M, or I; X$_3$ is F or M; X$_4$ is F or I; X$_5$ is S or T; X$_6$ is E or D; X$_7$ is N or S; X$_8$ is T, R, or S; X$_9$ is A or G; X$_{10}$ is E or D; X$_{11}$ is N or S; X$_{12}$ is N; X$_{13}$ is F or Y; X$_{14}$ is S; X$_{15}$ is S; X$_{16}$ is G or S; X$_{17}$ is T.

In another embodiment, X$_1$ is M, I, or S; X$_2$ is L, M, or I; X$_3$ is F or M; X$_4$ is I; X$_5$ is S or T; X$_6$ is D; X$_7$ is N or S; X$_8$ is T, R, or S; X$_9$ is A or G; X$_{10}$ is E or D; X$_{11}$ is N or S; X$_{12}$ is N; X$_{13}$ is F or Y; X$_{14}$ is S; X$_{15}$ is S; X$_{16}$ is G or S; X$_{17}$ is T.

In still another embodiment, X$_1$ is S; X$_2$ is I; X$_3$ is M; X$_4$ is I; X$_5$ is T; X$_6$ is D; X$_7$ is S; X$_8$ is S; X$_9$ is G; X$_{10}$ is D; X$_{11}$ is S; X$_{12}$ is N; X$_{13}$ is Y; X$_{14}$ is S; X$_{15}$ is S; X$_{16}$ is S; X$_{17}$ is T.

In a further aspect, the heavy chain variable region includes one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions include one or more framework sequences juxtaposed between the HVRs as: (LC-FR1 MHVR-L1)-(LC-FR2)-(HVR-L2)-(LC-FR3)-(HVR-L3)-(LC-FR4).

In a still further aspect, the framework sequences are derived from human consensus framework sequences or human germline sequences.

In a still further aspect, one or more of the heavy chain framework sequences is the following:

HC-FR1 is EVQLLESGGGLVQPGGSLRLSCAASGFTFS (SEQ ID NO: 24);

HC-FR2 is WVRQAPGKGLEWVS (SEQ ID NO: 25);

HC-FR3 is RFTISRDNSKNTLYLQMNSLRAEDTAVYYCAR (SEQ ID NO: 26);

HC-FR4 is WGQGTLVTVSS (SEQ ID NO: 27).

In a still further aspect, the light chain framework sequences are lambda light chain sequences.

In a still further aspect, one or more of the light chain framework sequences is the following:

LC-FR1 is QSALTQPASVSGSPGQSITISC (SEQ ID NO: 31);

LC-FR2 is WYQQHPGKAPKLMIY (SEQ ID NO: 32);

LC-FR3 is GVSNRFSGSKSGNTASLTISGLQAEDEADYYC (SEQ ID NO: 33);

LC-FR4 is FGTGTKVTVL (SEQ ID NO: 34).

In a still further aspect, the heavy chain variable region polypeptide, antibody, or antibody fragment further includes at least a $C_H1$ domain.

In a more specific aspect, the heavy chain variable region polypeptide, antibody, or antibody fragment further includes a $C_H1$, a $C_H2$, and a $C_H3$ domain.

In a still further aspect, the variable region light chain, antibody, or antibody fragment further includes a $C_L$ domain.

In a still further aspect, the antibody further includes a $C_HL$ a $C_H2$, a $C_H3$, and a $C_L$ domain.

In a still further specific aspect, the antibody further includes a human or murine constant region.

In a still further aspect, the human constant region is selected from the group consisting of IgG1, IgG2, IgG2, IgG3, IgG4.

In a still further specific aspect, the human or murine constant region is 1gG1.

In yet another embodiment, the invention features an anti-PD-L1 antibody including a heavy chain and a light chain variable region sequence, where:
  (a) the heavy chain includes an HVR-H1, an HVR-H2, and an HVR-H3, having at least 80% overall sequence identity to SYIMM (SEQ ID NO: 35), SIYPSGGITFY-ADTVKG (SEQ ID NO: 36), and IKLGTVTTVDY (SEQ ID NO: 37), respectively, and
  (b) the light chain includes an HVR-L1, an HVR-L2, and an HVR-L3, having at least 80% overall sequence identity to TGTSSDVGGYNYVS (SEQ ID NO: 38), DVSNRPS (SEQ ID NO: 39), and SSYTSSSTRV (SEQ ID NO: 40), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99%, or 100%.

In yet another embodiment, the invention features an anti-PD-L1 antibody including a heavy chain and a light chain variable region sequence, where:
  (a) the heavy chain includes an HVR-H1, an HVR-H2, and an HVR-H3, having at least 80% overall sequence identity to MYMMM (SEQ ID NO: 41), SIYPSG-GITFYADSVKG (SEQ ID NO: 42), and IKLGTVTTVDY (SEQ ID NO: 37), respectively, and
  (b) the light chain includes an HVR-L1, an HVR-L2, and an HVR-L3, having at least 80% overall sequence identity to TGTSSDVGAYNYVS (SEQ ID NO: 43), DVSNRPS (SEQ ID NO: 39), and SSYTSSSTRV (SEQ ID NO: 40), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99%, or 100%.

In a still further aspect, in the antibody or antibody fragment according to the invention, as compared to the sequences of HVR-H1, HVR-H2, and HVR-H3, at least those amino acids remain unchanged that are highlighted by underlining as follows:
  (a) in HVR-H1 SYIMM (SEQ ID NO: 35),
  (b) in HVR-H2 SIYPSGGITFYADTVKG (SEQ ID NO: 36),
  (c) in HVR-H3 IKLGTVTTVDY (SEQ ID NO: 37);
and further where, as compared to the sequences of HVR-L1, HVR-L2, and HVR-L3 at least those amino acids remain unchanged that are highlighted by underlining as follows:
  (a) HVR-L1 TGTSSDVGGYNYVS (SEQ ID NO: 38)
  (b) HVR-L2 DVSNRPS (SEQ ID NO: 39)
  (c) HVR-L3 SSYTSSSTRV (SEQ ID NO: 40).

In another aspect, the heavy chain variable region includes one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions include one or more framework sequences juxtaposed between the HVRs as: (LC-FR1)-(HVR-L1)-(LC-FR2)-(HVR-L2)-(LC-FR3)-(HVR-L3)-(LC-FR4).

In yet another aspect, the framework sequences are derived from human germline sequences.

In a still further aspect, one or more of the heavy chain framework sequences is the following:

HC-FR1 is EVQLLESGGGLVQPGGSLRLSCAASGFTFS (SEQ ID NO: 24);

HC-FR2 is WVRQAPGKGLEWVS (SEQ ID NO: 25);

HC-FR3 is RFTISRDNSKNTLYLQMNSLRAEDTAVYYCAR
(SEQ ID NO: 26);

HC-FR4 is WGQGTLVTVSS (SEQ ID NO: 27).

In a still further aspect, the light chain framework sequences are derived from a lambda light chain sequence.

In a still further aspect, one or more of the light chain framework sequences is the following:

LC-FR1 is QSALTQPASVSGSPGQSITISC (SEQ ID NO: 31);

LC-FR2 is WYQQHPGKAPKLMIY (SEQ ID NO: 32);

LC-FR3 is GVSNRFSGSKSGNTASLTISGLQAEDEADYYC
(SEQ ID NO: 33);

LC-FR4 is FGTGTKVTVL (SEQ ID NO: 34).

In a still further specific aspect, the antibody further includes a human or murine constant region.

In a still further aspect, the human constant region is selected from the group consisting of IgG1, IgG2, IgG2, IgG3, IgG4.

In a still further embodiment, the invention features an anti-PD-L1 antibody including a heavy chain and a light chain variable region sequence, where:

(a) the heavy chain sequence has at least 85%
sequence identity to the heavy chain sequence:
EVQLLESGGGLVQPGGSLRLSCAASGFTFSSYIMMVWRQAPGKGLEWVS

SIYPSGGITFYADWKGRFTISRDNSKNTLYLQMNSLRAEDTAVYYCARI

KLGTVTTVDYWGQGTLVTVSS (SEQ ID NO: 44),
and (b) the light chain sequence has at least 85%
sequence identity to the light chain sequence:
QSALTQPASVSGSPGQSITISCTGTSSDVGGYNYVSWYQQHPGKAPKLM

IYDVSNRPSGVSNRFSGSKSGNTASLTISGLQAEDEADYYCSSYTSSST

RVFGTGTKVTVL (SEQ ID NO: 45).

In a specific aspect, the sequence identity is 86%, 87%, 88%, 89%, 90%, 91%, 92%, 93%, 94%, 95%, 96%, 97%, 98%, 99%, or 100%.

In a still further embodiment, the invention provides for an anti-PD-L1 antibody including a heavy chain and a light chain variable region sequence, where:

(a) the heavy chain sequence has at least 85%
sequence identity to the heavy chain sequence:
EVQLLESGGGLVQPGGSLRLSCAASGFTFSMYMMMVWRQAPGKGLEVWS

SIYPSGGITFYADSVKGRFTISRDNSKNTLYLQMNSLRAEDTAIYYCAR

IKLGTVTTVDYWGQGTLVTVSS (SEQ ID NO: 46),
and (b) the light chain sequence has at least 85%
sequence identity to the light chain sequence:
QSALTQPASVSGSPGQSITISCTGTSSDVGAYNYVSWYQQHPGKAPKLM

IYDVSNRPSGVSNRFSGSKSGNTASLTISGLQAEDEADYYCSSYTSSST

RVFGTGTKVTVL (SEQ ID NO: 47).

In a specific aspect, the sequence identity is 86%, 87%, 88%, 89%, 90%, 91%, 92%, 93%, 94%, 95%, 96%, 97%, 98%, 99% or 100%.

In another embodiment the antibody binds to human, mouse, or cynomolgus monkey PD-L1. In a specific aspect the antibody is capable of blocking the interaction between human, mouse, or cynomolgus monkey PD-L1 and the respective human, mouse, or cynomolgus monkey PD-1 receptors.

In another embodiment, the antibody binds to human PD-L1 with a $K_D$ of $5\times10^{-9}$ M or less, preferably with a $K_D$ of $2\times10^{-9}$ M or less, and even more preferred with a $K_D$ of $1\times10^{-9}$ M or less.

In yet another embodiment, the invention relates to an anti-PD-L1 antibody or antigen binding fragment thereof which binds to a functional epitope including residues Y56 and D61 of human PD-L1.

In a specific aspect, the functional epitope further includes E58, E60, Q66, R113, and M115 of human PD-L1.

In a more specific aspect, the antibody binds to a conformational epitope, including residues 54-66 and 112-122 of human PD-L1.

In a further embodiment, the invention is related to an anti-PD-L1 antibody, or antigen binding fragment thereof, which cross-competes for binding to PD-L1 with an antibody according to the invention as described herein.

In a still further embodiment, the invention features proteins and polypeptides including any of the above described anti-PD-L1 antibodies in combination with at least one pharmaceutically acceptable carrier.

In a still further embodiment, the invention features an isolated nucleic acid encoding a polypeptide, or light chain or a heavy chain variable region sequence of an anti-PD-L1 antibody, or antigen binding fragment thereof, as described herein. In a still further embodiment, the invention provides for an isolated nucleic acid encoding a light chain or a heavy chain variable region sequence of an anti-PD-L1 antibody, wherein:

(a) the heavy chain includes an HVR-H1, an HVR-H2, and an HVR-H3 sequence having at least 80% sequence identity to SYIMM (SEQ ID NO: 35), SIYPSGGITFYADTVKG (SEQ ID NO: 36), and IKLGTVTTVDY (SEQ ID NO: 37), respectively, or (b) the light chain includes an HVR-L1, an HVR-L2, and an HVR-L3 sequence having at least 80% sequence identity to TGTSSDVGGYNYVS (SEQ ID NO: 38), DVSNRPS (SEQ ID NO: 39), and SSYTSSSTRV (SEQ ID NO: 40), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99%, or 100%.

In a further aspect, the nucleic acid sequence for the heavy chain is SEQ ID NO:48:

```
atggagttgc ctgttaggct gttggtgctg atgttctgga ttcctgctag ctccagcgag   60
gtgcagctgc tggaatccgg cggaggactg gtgcagcctg gcggctccct gagactgtct  120
tgcgccgcct ccggcttcac cttctccagc tacatcatga tgtgggtgcg acaggcccct  180
ggcaagggcc tggaatgggt gtcctccatc tacccctccg gcggcatcac cttctacgcc  240
gacaccgtga agggccggtt caccatctcc cgggacaact ccaagaacac cctgtacctg  300
cagatgaact ccctgcgggc cgaggacacc gccgtgtact actgcgcccg gatcaagctg  360
ggcaccgtga ccaccgtgga ctactggggc cagggcaccc tggtgacagt gtcctccgcc  420
tccaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaactcct ggggggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacaacagc  960
acgtaccgtg tggtcagcgt cctcaccgtc ctgcaccagg actggctgaa tggcaaggag 1020
tacaagtgca aggtctccaa caaagccctc ccagccccca tcgagaaaac catctccaaa 1080
gccaaagggc agccccgaga accacaggtg tacaccctgc ccccatcacg ggatgagctg 1140
accaagaacc aggtcagcct gacctgcctg gtcaaaggct tctatcccag cgacatcgcc 1200
gtggagtggg agagcaatgg gcagccggag aacaactaca agaccacgcc tcccgtgctg 1260
gactccgacg gctccttctt cctctatagc aagctcaccg tggacaagag caggtggcag 1320
caggggaacg tcttctcatg ctccgtgatg catgaggctc tgcacaacca ctacacgcag 1380
aagagcctct ccctgtcccc gggtaaa                                    1407
``` and the nucleic acid sequence for the light chain is SEQ ID NO:49:

```
atggagttgc ctgttaggct gttggtgctg atgttctgga ttcctgcttc cttaagccag   60
tccgccctga cccagcctgc ctccgtgtct ggctcccctg gccagtccat caccatcagc  120
tgcaccggca cctccagcga cgtgggcggc tacaactacg tgtcctggta tcagcagcac  180
cccggcaagg cccccaagct gatgatctac gacgtgtcca accggccctc cggcgtgtcc  240
aacagattct ccggctccaa gtccggcaac accgcctccc tgaccatcag cggactgcag  300
gcagaggacg aggccgacta ctactgctcc tcctacacct cctccagcac cagagtgttc  360
ggcaccggca aaaagtgac cgtgctgggc cagcccaagg ccaacccaac cgtgacactg  420
ttcccccat cctccgagga actgcaggcc aacaaggcca cctggtctg cctgatctca  480
gatttctatc caggcgccgt gaccgtggcc tggaaggctg atggctcccc agtgaaggcc  540
ggcgtggaaa ccaccaagcc ctccaagcag tccaacaaca aatacgccgc ctcctcctac  600
ctgtccctga ccccgagca gtggaagtcc caccggtcct acagctgcca ggtcacacac  660
gagggctcca ccgtggaaaa gaccgtcgcc cccaccgagt gctca                 705
```

Further exemplary anti-PD-L1 antibodies that can be used in an anti-PD-L1/TGFβ Trap are described in US patent application publication US 2010/0203056. In one embodiment of the invention, the antibody moiety is YW243.55S70. In another embodiment of the invention, the antibody moiety is MPDL3280A.

In a further embodiment, the invention features an anti-PD-L1 antibody moiety including a heavy chain and a light chain variable region sequence, where:

```
(a) the heavy chain sequence has at least 85% sequence
identity to the heavy chain sequence:
                                            (SEQ ID NO: 12)
EVQLVESGGGLVQPGGSLRLSCAASGFTFSDSWIHWVRQAPGKGLEWVAWISPYGGSTYY ADSVKGRFTISADTSKNTAYLQMNSLRAEDTAVYYCARRHWPGGFDYWGQGTLVTVSS,
and
(b) the light chain sequence has at least 85% sequence
identity to the light chain sequence:
                                            (SEQ ID NO: 13)
DIQMTQSPSSLSASVGDRVTITCRASQDVSTAVAWYQQKPGKAPKLLIYSASFLY-
SGVPSRFSG

SGSGTDFTLTISSLQPEDFATYYCQQYLYHPATFGQGTKVEIKR.
```

In a specific aspect, the sequence identity is 86%, 87%, 88%, 89%, 90%, 91%, 92%, 93%, 94%, 95%, 96%, 97%, 98%, or 99%.

In a further embodiment, the invention features an anti-PD-L1 antibody moiety including a heavy chain and a light chain variable region sequence, where:

```
(a) the heavy chain variable region sequence is:
                                            (SEQ ID NO: 12)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS,
and (b) the light chain variable region sequence is:
                                            (SEQ ID NO: 13)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a further embodiment, the invention features an anti-PD-L1 antibody moiety including a heavy chain and a light chain variable region sequence, where:

```
(a) the heavy chain variable region sequence is:
                                            (SEQ ID NO: 14)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA,
and (b) the light chain variable region sequence is:
                                            (SEQ ID NO: 13)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

Yet further exemplary anti-PD-L1 antibodies that can be used in an anti-PD-L1/TGFβ Trap are described in US patent publication U.S. Pat. No. 7,943,743.

In one embodiment of the invention, the anti-PD-L1 antibody is MDX-1105.

In yet a further embodiment, the anti-PD-L1 antibody is MEDI-4736.

Constant Region

The proteins and peptides of the invention can include a constant region of an immunoglobulin or a fragment, analog, variant, mutant, or derivative of the constant region. In preferred embodiments, the constant region is derived from a human immunoglobulin heavy chain, for example, IgG1, IgG2, IgG3, IgG4, or other classes. In one embodiment, the constant region includes a CH2 domain. In another embodiment, the constant region includes CH2 and CH3 domains or includes hinge-CH2-CH3. Alternatively, the constant region can include all or a portion of the hinge region, the CH2 domain and/or the CH3 domain.

In one embodiment, the constant region contains a mutation that reduces affinity for an Fc receptor or reduces Fc effector function. For example, the constant region can contain a mutation that eliminates the glycosylation site within the constant region of an IgG heavy chain. In some embodiments, the constant region contains mutations, deletions, or insertions at an amino acid position corresponding to Leu234, Leu235, Gly236, Gly237, Asn297, or Pro331 of IgG1 (amino acids are numbered according to EU nomenclature). In a particular embodiment, the constant region contains a mutation at an amino acid position corresponding to Asn297 of IgG1. In alternative embodiments, the constant region contains mutations, deletions, or insertions at an amino acid position corresponding to Leu281, Leu282, Gly283, Gly284, Asn344, or Pro378 of IgG1.

In some embodiments, the constant region contains a CH2 domain derived from a human IgG2 or IgG4 heavy chain. Preferably, the CH2 domain contains a mutation that eliminates the glycosylation site within the CH2 domain. In one embodiment, the mutation alters the asparagine within the Gln-Phe-Asn-Ser (SEQ ID NO: 15) amino acid sequence within the CH2 domain of the IgG2 or IgG4 heavy chain. Preferably, the mutation changes the asparagine to a glutamine. Alternatively, the mutation alters both the phenylalanine and the asparagine within the Gln-Phe-Asn-Ser (SEQ ID NO: 15) amino acid sequence. In one embodiment, the Gln-Phe-Asn-Ser (SEQ ID NO: 15) amino acid sequence is replaced with a Gln-Ala-Gln-Ser (SEQ ID NO: 16) amino acid sequence. The asparagine within the Gln-Phe-Asn-Ser (SEQ ID NO: 15) amino acid sequence corresponds to Asn297 of IgG1.

In another embodiment, the constant region includes a CH2 domain and at least a portion of a hinge region. The hinge region can be derived from an immunoglobulin heavy chain, e.g., IgG1, IgG2, IgG3, IgG4, or other classes. Preferably, the hinge region is derived from human IgG1, IgG2, IgG3, IgG4, or other suitable classes. More preferably the hinge region is derived from a human IgG1 heavy chain. In one embodiment the cysteine in the Pro-Lys-Ser-Cys-Asp-Lys (SEQ ID NO: 17) amino acid sequence of the IgG1 hinge region is altered. In a preferred embodiment the Pro-Lys-Ser-Cys-Asp-Lys (SEQ ID NO: 17) amino acid sequence is replaced with a Pro-Lys-Ser-Ser-Asp-Lys (SEQ ID NO: 18) amino acid sequence. In one embodiment, the constant region includes a CH2 domain derived from a first antibody isotype and a hinge region derived from a second antibody isotype. In a specific embodiment, the CH2 domain is derived from a human IgG2 or IgG4 heavy chain, while the hinge region is derived from an altered human IgG1 heavy chain.

The alteration of amino acids near the junction of the Fc portion and the non-Fc portion can dramatically increase the serum half-life of the Fc fusion protein (PCT publication WO 01/58957, the disclosure of which is hereby incorporated by reference). Accordingly, the junction region of a protein or polypeptide of the present invention can contain alterations that, relative to the naturally-occurring sequences of an immunoglobulin heavy chain and erythropoietin, preferably lie within about 10 amino acids of the junction point. These amino acid changes can cause an increase in hydrophobicity. In one embodiment, the constant region is derived from an IgG sequence in which the C-terminal lysine residue is replaced. Preferably, the C-terminal lysine of an IgG sequence is replaced with a non-lysine amino acid, such as alanine or leucine, to further increase serum half-life. In another embodiment, the constant region is derived from an IgG sequence in which the Leu-Ser-Leu-Ser (SEQ ID NO: 19) amino acid sequence near the C-terminus of the constant region is altered to eliminate potential junctional T-cell epitopes. For example, in one embodiment, the Leu-Ser-Leu-Ser (SEQ ID NO: 19) amino acid sequence is replaced with an Ala-Thr-Ala-Thr (SEQ ID NO: 20) amino acid sequence. In other embodiments, the amino acids within the Leu-Ser-Leu-Ser (SEQ ID NO: 19) segment are replaced with other amino acids such as glycine or proline. Detailed methods of generating amino acid substitutions of the Leu-Ser-Leu-Ser (SEQ ID NO: 19) segment near the C-terminus of an IgG1, IgG2, IgG3, IgG4, or other immunoglobulin class molecule have been described in U.S. Patent Publication No. 2003/0166877, the disclosure of which is hereby incorporated by reference.

Suitable hinge regions for the present invention can be derived from IgG1, IgG2, IgG3, IgG4, and other immunoglobulin classes. The IgG1 hinge region has three cysteines, two of which are involved in disulfide bonds between the two heavy chains of the immunoglobulin. These same cysteines permit efficient and consistent disulfide bonding formation between Fc portions. Therefore, a preferred hinge region of the present invention is derived from IgG1, more preferably from human IgG1. In some embodiments, the first cysteine within the human IgG1 hinge region is mutated to another amino acid, preferably serine. The IgG2 isotype hinge region has four disulfide bonds that tend to promote oligomerization and possibly incorrect disulfide bonding during secretion in recombinant systems. A suitable hinge region can be derived from an IgG2 hinge; the first two cysteines are each preferably mutated to another amino acid. The hinge region of IgG4 is known to form interchain disulfide bonds inefficiently. However, a suitable hinge region for the present invention can be derived from the IgG4 hinge region, preferably containing a mutation that enhances correct formation of disulfide bonds between heavy chain-derived moieties (Angal S, et al. (1993) Mol. Immunol., 30:105-8).

In accordance with the present invention, the constant region can contain CH2 and/or CH3 domains and a hinge region that are derived from different antibody isotypes, i.e., a hybrid constant region. For example, in one embodiment, the constant region contains CH2 and/or CH3 domains derived from IgG2 or IgG4 and a mutant hinge region derived from IgG1. Alternatively, a mutant hinge region from another IgG subclass is used in a hybrid constant region. For example, a mutant form of the IgG4 hinge that allows efficient disulfide bonding between the two heavy chains can be used. A mutant hinge can also be derived from an IgG2 hinge in which the first two cysteines are each mutated to another amino acid. Assembly of such hybrid constant regions has been described in U.S. Patent Publication No. 2003/0044423, the disclosure of which is hereby incorporated by reference.

In accordance with the present invention, the constant region can contain one or more mutations described herein. The combinations of mutations in the Fc portion can have additive or synergistic effects on the prolonged serum half-life and increased in vivo potency of the bifunctional molecule. Thus, in one exemplary embodiment, the constant region can contain (i) a region derived from an IgG sequence in which the Leu-Ser-Leu-Ser (SEQ ID NO: 19) amino acid sequence is replaced with an Ala-Thr-Ala-Thr (SEQ ID NO: 20) amino acid sequence; (ii) a C-terminal alanine residue instead of lysine; (iii) a CH2 domain and a hinge region that are derived from different antibody isotypes, for example, an IgG2 CH2 domain and an altered IgG1 hinge region; and (iv) a mutation that eliminates the glycosylation site within the IgG2-derived CH2 domain, for example, a Gln-Ala-Gln-Ser (SEQ ID NO: 16) amino acid sequence instead of the Gln-Phe-Asn-Ser (SEQ ID NO: 15) amino acid sequence within the IgG2-derived CH2 domain.

Antibody Fragments

The proteins and polypeptides of the invention can also include antigen-binding fragments of antibodies. Exemplary antibody fragments include scFv, Fv, Fab, F(ab')$_2$, and single domain VHH fragments such as those of camelid origin.

Single-chain antibody fragments, also known as single-chain antibodies (scFvs), are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

Fragments of antibodies that have the same or comparable binding characteristics to those of the whole antibody may also be present. Such fragments may contain one or both Fab fragments or the F(ab')$_2$ fragment. The antibody fragments may contain all six CDRs of the whole antibody, although fragments containing fewer than all of such regions, such as three, four or five CDRs, are also functional.

Protein Production

The antibody-cytokine trap proteins are generally produced recombinantly, using mammalian cells containing a nucleic acid engineered to express the protein. Although one example of a suitable cell line and protein production method is described in Examples 1 and 2, a wide variety of suitable vectors, cell lines and protein production methods have been used to produce antibody-based biopharmaceuticals and could be used in the synthesis of these antibody-cytokine trap proteins.

Therapeutic Indications

The anti-PD-L1/TGFβ Trap proteins described in the application can be used to treat cancer or reduce tumor growth in a patient. Exemplary cancers include colorectal, breast, ovarian, pancreatic, gastric, prostate, renal, cervical, myeloma, lymphoma, leukemia, thyroid, endometrial, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, and myelodisplastic syndromes.

The cancer or tumor to be treated with an anti-PD-L1/TGFβ Trap may be selected based on the expression or elevated expression of PD-L1 and TGFβ in the tumor, the correlation of their expression levels with prognosis or disease progression, and preclinical and clinical experience on the sensitivity of the tumor to treatments targeting PD-L1 and TGFβ. Such cancers or tumors include but are not limited to colorectal, breast, ovarian, pancreatic, gastric, prostate, renal, cervical, bladder, head and neck, liver, non-small cell lung cancer, melanoma, Merkel cell carcinoma, and mesothelioma.

Pharmaceutical Compositions

The present invention also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The pharmaceutical compositions are intended for parenteral, intranasal, topical, oral, or local administration, such as by a transdermal means, for therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The optimal dose of the antibody-TGFβ trap is based on the percent receptor occupancy by the antibody moiety to achieve maximal therapeutic effect because the cytokine trap is used in a large excess. For example, the therapeutic dose for a monoclonal antibody targeting a cellular receptor is determined such that the trough level is around 10 to 100 µg/ml, i.e., 60 to 600 nM (for antibody with a dissociation constant ($K_D$) of 6 nM, this trough level would ensure that between 90 to 99% of the target receptors on the cells are occupied by the antibody). This is in large excess of cytokines, which are typically present in pg to ng/ml in circulation.

The optimal dose of antibody-TGFβ trap polypeptide of the invention will depend on the disease being treated, the severity of the disease, and the existence of side effects. The optimal dose can be determined by routine experimentation. For parenteral administration a dose between 0.1 mg/kg and 100 mg/kg, alternatively between 0.5 mg/kg and 50 mg/kg, alternatively, between 1 mg/kg and 25 mg/kg, alternatively between 2 mg/kg and 10 mg/kg, alternatively between 5 mg/kg and 10 mg/kg is administered and may be given, for example, once weekly, once every other week, once every third week, or once monthly per treatment cycle.

EXAMPLES

The invention now being generally described, will be more readily understood by reference to the following examples, which are included merely for purposes of illustration of certain aspects and embodiments of the present invention, and are not intended to limit the scope of the invention in any way.

Example 1 DNA Construction and Protein Expression

Anti-PD-L1/TGFβ Trap is an anti-PD-L1 antibody-TGFβ Receptor II fusion protein. The light chain of the molecule is identical to the light chain of the anti-PD-L1 antibody (SEQ ID NO:1). The heavy chain of the molecule (SEQ ID NO:3) is a fusion protein comprising the heavy chain of the anti-PD-L1 antibody (SEQ ID NO:2) genetically fused to via a flexible (Gly$_4$Ser)$_4$Gly linker (SEQ ID NO:11) to the N-terminus of the soluble TGFβ Receptor II (SEQ ID NO:10). At the fusion junction, the C-terminal lysine residue of the antibody heavy chain was mutated to alanine to reduce proteolytic cleavage. For expression of anti-PD-L1/TGFβ Trap, the DNA encoding the anti-PD-L1 light chain (SEQ ID NO:4) and the DNA encoding the anti-PD-L1/TGFβ Receptor II (SEQ ID NO:5) in either the same expression vector or separate expression vectors were used to transfect mammalian cells using standard protocols for transient or stable transfection. Conditioned culture media were harvested and the anti-PD-L1/TGFβ Trap fusion protein was purified by standard Protein A Sepharose chromatography. The purified protein comprising one anti-PD-L1 antibody and two soluble TGFβ Receptor II molecules (FIG. 1A) has an estimated molecular weight (MW) of about 190 kilodaltons on size exclusion chromatography and SDS-polyacrylamide electrophoresis under non-reducing conditions. Under reducing conditions, the light and heavy chains have apparent MW of 28 and 75 kilodaltons, respectively (FIG. 1B).

The anti-PD-L1(mut)/TGFβ Trap fusion protein, which contains an analogous heavy chain fusion polypeptide (SEQ ID NO:7) and a light chain with the mutations A31G, D52E, R99Y in the variable region that abrogate the binding to PD-L1 (SEQ ID NO:6), was similarly prepared. It was used in subsequent experiments as a TGFβ Trap control.

Example 2 Production of Anti-PD-L1/TGFβ Trap as a Biotherapeutic

Figure 1B:
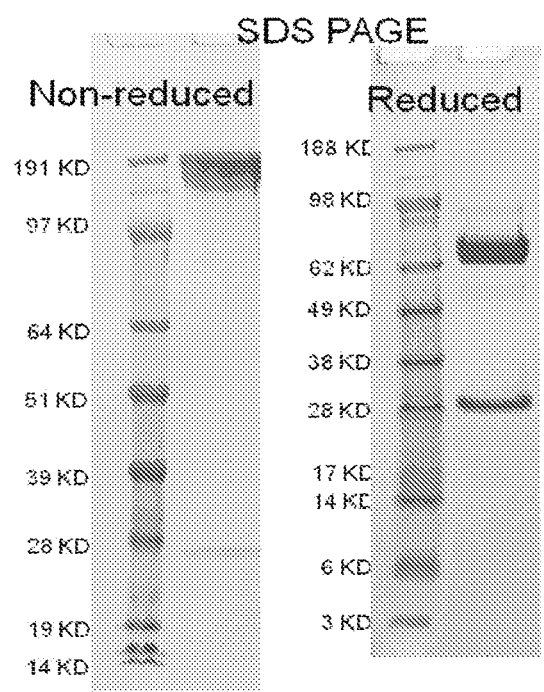
FIG. 1B is a photograph of a sodium dodecyl sulfate-polyacrylamide gel electrophoresis (SDS-PAGE) analysis of anti-PD-L1/TGFβ Trap under non-reducing and reducing conditions.

The anti-PD-L1/TGFβ Trap produced by transient transfection of human embryonic kidney 293 (HEK) cells was found to contain varying degrees of a clipped species, which appeared as a faint band with an apparent MW of about 60 kD on SDS-PAGE under reducing conditions (FIG. 1B). This band was confirmed to be the heavy chain of the anti-PD-L1/TGFβ Trap cleaved at a site in the N-terminal portion of TGFβRII close to the fusion junction.

Figure 2:
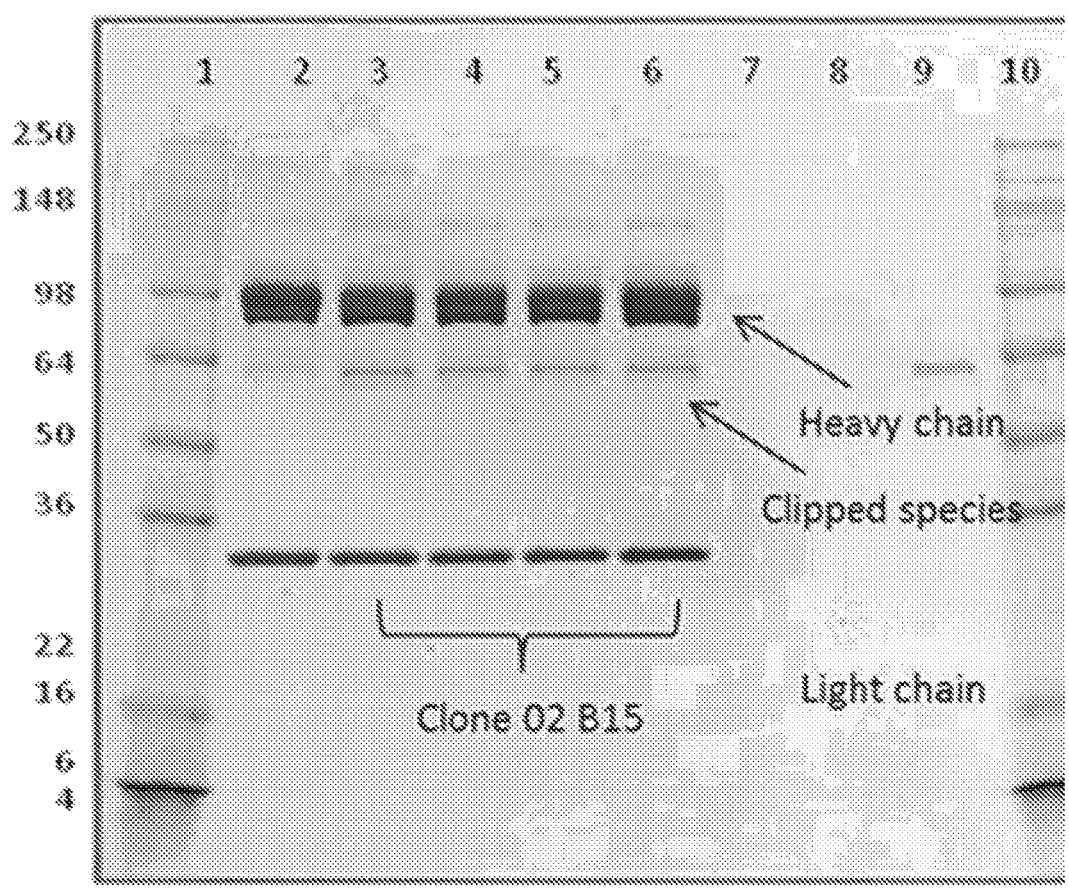
FIG. 2 is photograph of an SDS-PAGE gel showing analysis of extent of clipping of anti-PD-L1/TGFβ Trap expressed by clone 02B15 at various population doubling levels. Anti-PD-L1/TGFβ Trap from clone 02B15 after a single protein A chromatography step was analyzed by SDS-PAGE under reducing conditions. Lanes 1 and 10, See Blue Plus 2 MW Standard; lane 2, purified anti-PD-L1/TGFβ Trap reference; lane 3, clone 02B15 at PDL0; lane 4, clone 02B15 at PDL30; lane 5, clone 02B15 at PDL60; and lane 6, clone 02B15 at PDL90. (PDL, population doubling level).

Stable clones expressing anti-PD-L1/TGFβ Trap were generated in the CHO-S host cell line, which was pre-adapted for growth in serum-free media in suspension culture. Cells were transfected with an expression vector containing a gene encoding the anti-PD-L1-TGFβRII protein and a glutamine synthetase selection marker. Subsequent selection of stable integrants was made with L-methionine sulfoximine (MSX). Anti-PD-L1/TGFβ Trap expressing cell lines were generated using a minipool approach, followed by the deposition of single cells into 384-well plates, using a Beckton-Dickinson fluorescence activated cell sorter (FACS Aria II). Growth, productivity, and protein quality were evaluated in a generic platform fed-batch assay. Based on these analyses, 14 clones were selected as lead candidates for further studies. A stability study with the clones was carried out to 90 PDL (population doubling level) from research cell banks established during scale up of clones. At the conclusion of minipool development it was discovered that the heavy chain-linker-TGFβRII subunit underwent clipping, as was seen in transient expression. All clones in the stability study produced the clipped species, although it was shown in the protein A-purified material that the percent clipped species relative to the intact subunit varied with each clone. In addition, an improved purification process consisting a protein A chromatography followed by strong cation exchange was developed to reduce co-purification of the clipped species. Even with the improved process, purified material with the required final levels of clipped species of <5% could only be achieved using clones producing low levels of clipping. Based on these combined analyses, clone 02B15 was selected as the final candidate clone. Analysis of anti-PD-L1/TGFβ Trap expressed by this clone at zero PDL, thirty PDL, sixty PDL and ninety PDL shows that the percentage of clipping did not increase with population doubling levels (FIG. 2).

Example 3 Fluorescence-Activated Cell Sorting (FACS) Analysis of Binding of Anti-PD-L1/TGFβ Trap and Controls to Human PD-L1 on Cells The binding of anti-PD-L1 antibody and fusion proteins on HEK cells stably transfected to express human PD-L1 was studied using the following procedure.

The following exemplary procedure was used determine PD-L1 binding by FACS:
 a. 50 µl serial dilutions of test samples were set up in FACS buffer.
 b. 50 µl of HEK cells stably transfected to express human PD-L1 at 5×10$^6$ cells/ml were dispensed to the wells with test samples and mixed.
 c. Plate(s) were incubated in the dark on ice for 1 hour.
 d. Cells were pelleted at 300×g for 5 minutes.
 e. Supernatant was decanted and cells were resuspended in 300 µl FACS buffer and re-pelleted at 300×g for 5.
 f. Sample rinse was repeated.
 g. Cells were resuspended in 100 µl FACS buffer containing DyLight 488 conjugated whole IgG Goat Anti-Human IgG, Fcγ (1:300 diluted).
 h. Plate(s) was incubated in the dark on ice for 45 minutes.
 i. Cells were pelleted at 300×g for 5.
 j. Supernatant was decanted and cells were resuspended in 300 µl FACS buffer and re-pelleted at 300×g for 5 minutes
 k. Sample rinse was repeated and cells were finally resuspended in 200 µl FACS buffer.
 l. Data was acquired on FACS Caliber and was analyzed using Microsoft Excel. EC50 was calculated using non-linear regression (Sigmoidal dose-response) with Graphpad Prism5.

Figure 3:
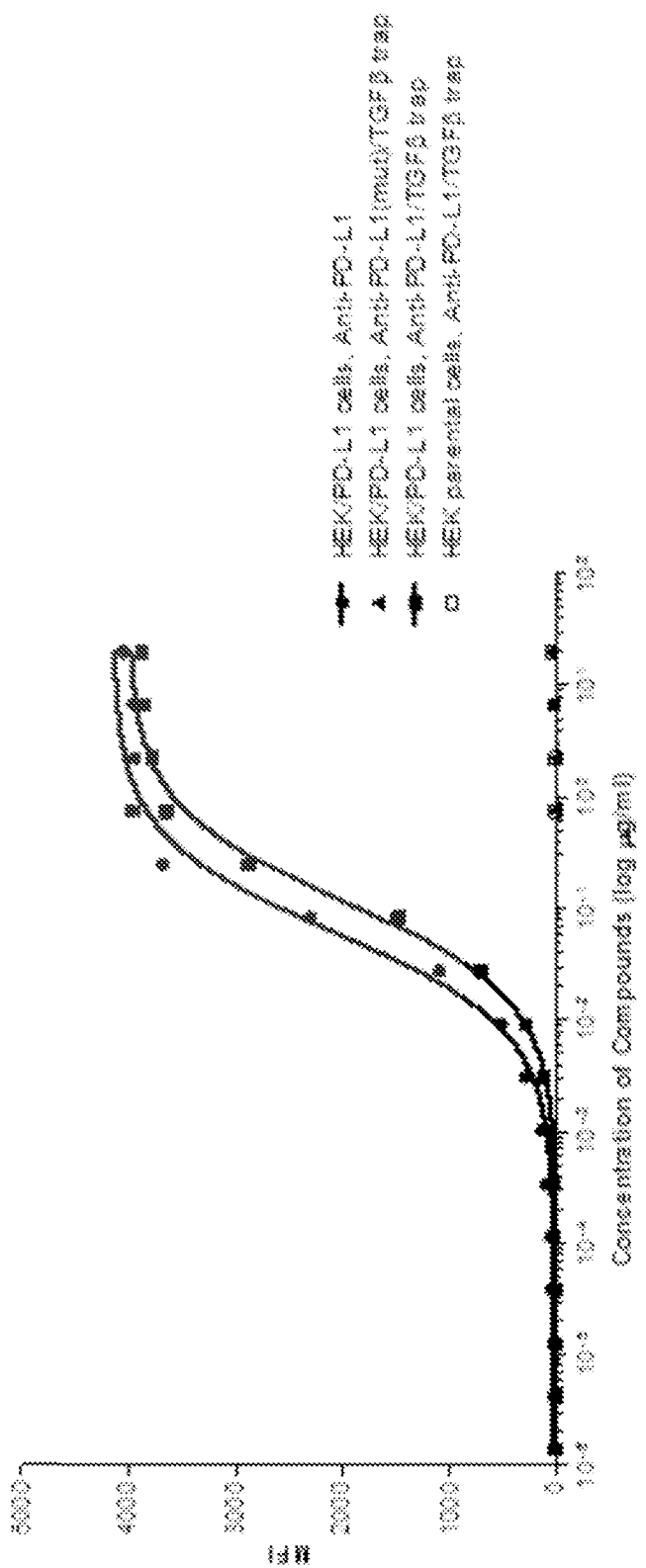
FIG. 3 is a graph showing FACS analysis of anti-PD-L1/TGFβ Trap binding to HEK cells transfected to express human PD-L1.

As shown in FIG. 3, FACS analysis showed that the anti-PD-L1/TGFβ Trap fusion protein retains similar binding affinity as the positive control anti-PD-L1 antibody on HEK cells stably transfected to express human PD-L1 (HEK/PD-L1 cells). The EC50's for anti-PD-L1/TGFβ Trap and anti-PD-L1 are 0.116 µg/ml (0.64 nM) and 0.061 µg/ml (0.41 nM), respectively. The observed MFI (mean fluorescent intensity) was specific to binding to human PD-L1 since no MFI was observed on the parental HEK cells that were not transfected. The anti-PD-L1(mut)/TGFβ Trap negative control did not show any binding to the HEK cells stably transfected to express human PD-L1.

Example 4 Determination of Ability of Anti-PD-L1/TGFβ Trap to Inhibit TGFβ Induced Phosphorylation of SMAD3

The ability of anti-PD-L1/TGFβ Trap to neutralize TGFβ was determined using 4T1 cells carrying a SMAD3-luciferase reporter. In the assay detailed below, inhibition of TGFβ-induced phosphorylation of SMAD3 was measured using a luciferase reporter under the control of the SMAD3 promoter.

An exemplary assay to evaluate potency to inhibit TGFβ-induced reporter activity was performed as follows.
1. One day prior to the study, 4T1 cells carrying SMAD3-luciferase reporter were fed.
2. On day 0, cells were plated in a Biocoat 96-well plate at a concentration of $5 \times 10^4$ cells/well in 100 μl of fresh media and incubated overnight at 37° C. and 5% $CO_2$.
3. On day 1:
   i. 50 μl of fresh complete media containing indicated concentration of anti-PD-L1/TGFβ trap samples to be tested or its controls was added to the wells and incubated for one hour. All samples were tested in triplicates.
   ii. 50 μl of fresh complete media containing 20 ng/ml human TGFβ was added to each well and samples were incubated overnight (final concentration in the well is 5 ng/ml).
4. On day 2:
   i. 100 μl culture supernatant was removed and 100 μl fresh complete media, containing 150 ng/ml D-Luciferin was added, and samples were incubated for at least five minutes.
   ii. Luminescence was measured using Envision 2104 plate reader by recording CPM.
5. Data was analyzed using MS Excel or Graphpad prism 5. Luciferase activity was recorded as CPM. Inhibitory Activity of (%) was calculated using the following equation:

Inhibition(%)=(1−CPM of sample/CPM max of anti-PD-L1 treated sample)×100

6. Nonlinear regression fit was carried out using Sigmoidal dose-response (variable slope) of Graphpad prism 5. IC50 values were calculated.

Figure 4:
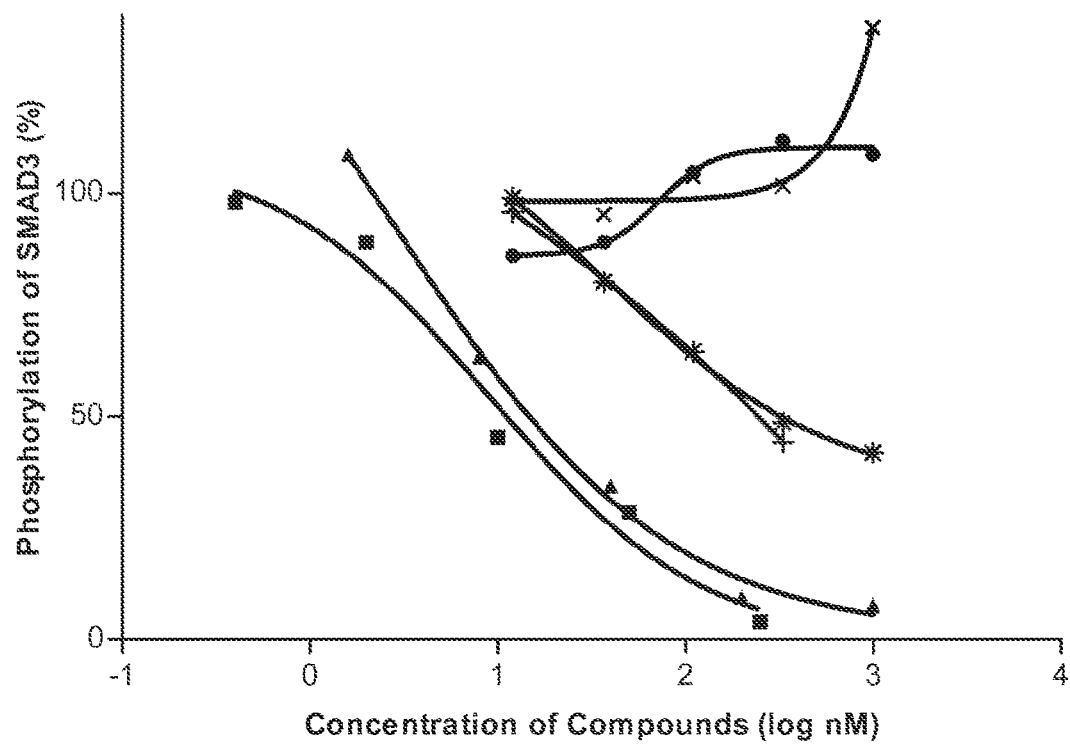
FIG. 4 is a graph showing the ability of anti-PD-L1/TGFβ Trap to inhibit TGFβ-induced phosphorylation of SMAD3 using a pSMAD3-luciferase reporter cell line (filled circle: anti-PD-L1; X: anti-PD-L1 (mut); filled square: anti-PD-L1/TGFβ Trap; filled triangle: anti-PD-L1(mut)/TGFβ Trap; +: anti-TGFβ antibody 1D11; star: TGFβ RII-Fc).

FIG. 4 shows that anti-PD-L1/TGFβ Trap inhibits TGFβ-induced pSMAD3 reporter activity in a dose dependent manner. The fact that the anti-PD-L1(mut)/TGFβ Trap control had comparable potency and IC50 (concentration required to inhibit 50% of the maximal activity) plus the fact that the anti-PD-L1 antibody had no effect showed that this inhibition of signaling is independent of anti-PD-L1 activity. Surprisingly, anti-PD-L1/TGFβ Trap was several-fold more potent than TGFβRII-Fc (R&D Systems), which places the TGFβRII at the N-terminus instead of the C-terminus of the fusion protein. It is also noteworthy that anti-PD-L1/TGFβ Trap is significantly more potent than 1D11 (GC1008), the anti-TGFβ antibody that was tested in patients with advanced malignant melanoma or renal cell carcinoma (Morris et al., J Clin Oncol 2008; 26:9028 (Meeting abstract)). In this assay, 1D11 and TGFβRII-Fc showed similar activity.

Example 5 Pharmacokinetic (PK) Analysis in Mice

Eighteen male C57BL/6 mice, 5-6 weeks old, were randomly assigned to 3 groups (N=6/group), and each group received one of the three proteins (anti-PD-L1/TGFβ Trap, anti-PD-L1(mut)/TGFβ Trap, and anti-PD-L1). Mouse body weight was recorded before dosing. After a brief warm-up under a heating lamp, each mouse received 120 ng of protein in 200 μl intravenously (IV) via the tail vein regardless of its body weight. Each group dosed with the same protein was further divided into 2 subgroups (n=3). Blood samples were alternately taken from each of two subgroups, i.e. one subgroup was withdrawn for blood samples at 1 h, 24 h, 72 h, and 168 h, whereas another subgroup was for blood samples at 7 h, 48 h, 120 h, and 240 h. At each time point, approximate 50 μl of blood samples were collected from each mouse via tail vein using a heparinized micro glass capillary (100 μl in capacity). The blood sample was then transferred to a tube pre-coated with Li-Heparin and kept at 4° C. Within 10 min of collection, the blood samples were spun at 14,000 rpm for 10 min. At least 20 μl of plasma sample was transferred into a new set of pre-labeled tubes and stored at −20° C. until the day of analysis.

The ELISA to measure total human IgG used goat anti-Human IgG (H+L) (heavy and light chains) (Jackson ImmunoResearch Laboratories) coated wells for capture and peroxidase-AffiniPure mouse anti-Human IgG, F(ab')2 (Jackson ImmunoResearch Laboratories) for detection. The ELISA to measure fully functional anti-PD-L1 antibody and/or fusion protein used PD-L1-Fc (extracellular domain of human PD-L1 fused to Fc) coated wells (coated at 1.25 ng/ml) for capture and peroxidase-AffiniPure mouse anti-Human IgG, F(ab')2 for detection. The ELISA to measure fully functional anti-PD-L1 and intact TGFβRII used PD-L1-Fc coated wells for capture and biotinylated anti-human TGFβRII (R&D Systems) for detection.

Figure 5A:
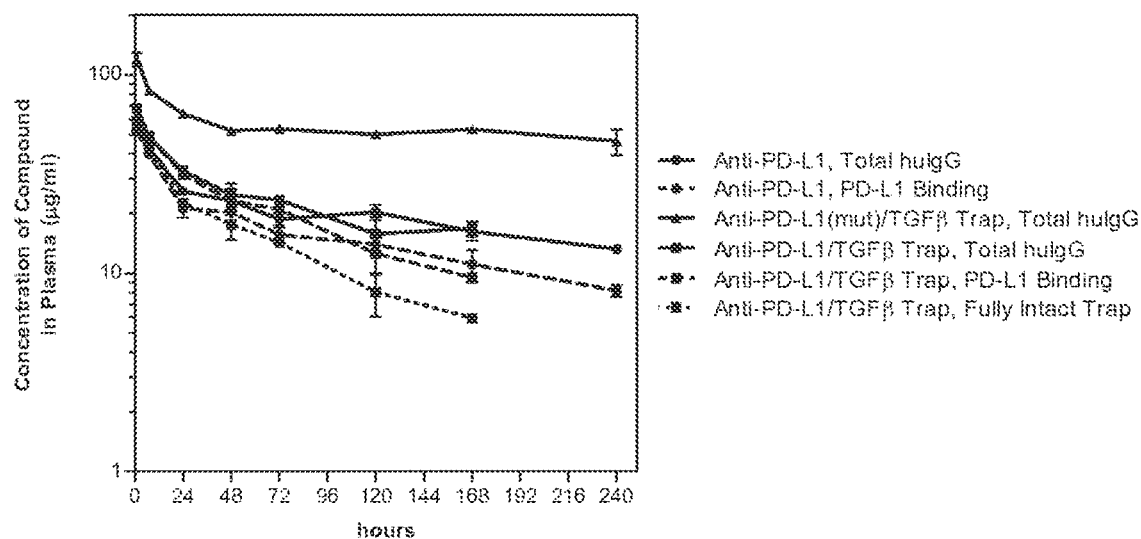
FIGS. 5A and 5B are graphs showing pharmacokinetics of intravenously administered anti-PD-L1/TGFβ Trap and related proteins in mice.

FIG. 5A shows that the anti-PD-L1/TGFβ Trap fusion protein had a PK profile very similar to that of the anti-PD-L1 antibody. For example, as measured by the total human IgG ELISA, the serum concentrations at the 168 hr time point of anti-PD-L1/TGFβ Trap and anti-PD-L1 were 16.8 and 16.2 ng/ml, respectively, and the respective area under the curve (AUC) from 0 to 168 hr were 4102 and 3841 hr-ng/ml. Similarly, when the serum concentrations were measured by the total functional anti-PD-L1 ELISA, the serum concentrations at the 168 hr time point of anti-PD-L1/TGFβ Trap and anti-PD-L1 were 9.5 and 11.1 ng/ml, respectively, and the respective AUC from 0 to 168 hr were 3562 and 3086 hr-ng/ml. The serum concentration of intact anti-PD-L1/TGFβ Trap fusion protein was determined by the ELISA, which detects fully functional anti-PD-L1 and the fused TGFβRII. In this case, the serum concentration of anti-PD-L1/TGFβ Trap was 5.9 ng/ml at the 168 hr time point and the AUC (0 to 168 hr) was 2656 hr-ng/ml, which were somewhat lower than those from the fully functional anti-PD-L1 ELISA, presumably due to degradation of the TGFβRII moiety after receptor-mediated endocytosis. Antibody binding to PD-L1 has been shown to result in PD-L1-mediated endocytosis, and an antibody-X fusion protein is known to undergo degradation of the X moiety after receptor-mediated endocytosis (Gillies et al., Clin Cancer Res. 2002; 8:210-6). This is supported by the finding in FIG. 5 that when the antibody moiety does not bind PD-L1, as in the anti-PD-L1(mut)/TGFβ Trap control, the exposure is about 3 times higher, with a serum concentration of 53 μg/ml at the 168 hr time point and AUC(0 to 168 hr) of 9585 hr-μg/ml, suggesting that at least part of the clearance is receptor-mediated.

In order to confirm the 3-fold difference in exposure between anti-PD-L1/TGFβ Trap and anti-PD-L1(mut)/TGFβ Trap, the pharmacokinetics experiment was repeated and the concentrations of the intact fusion proteins in the serum samples were determined. Mice (B6.129S2 female mice, 8 wks old, Jackson Lab) were injected with anti-PD-L1/TGFβ Trap or anti-PD-L1(mut)/TGFβ Trap (164 μg/mouse). The serum concentrations of the two fusion proteins were measured by an ELISA using anti-human IgG Fab (Jackson Immunoresearch, West Grove, Pa.) for capture and biotinylated anti-human TGFβRII (R&D Systems, Minneapolis, Minn.) and peroxidase-conjugated streptavidin (Zymed/ThermoFisher Scientific, Grand Island, N.Y.) to detect intact anti-PD-L1/TGFβ Trap proteins. The serum concentrations of the intact fusion proteins at various time points were shown in the Table below and plotted in FIG. 5B. The total area under the curve (AUC) up to 336 hr is 11781 hr-μg/ml for anti-PD-L1/TGFβ Trap and 35575 hr-μg/ml for anti-PD-L1(mut)/TGFβ Trap (Table 1), therefore confirming the three-fold higher exposure of the Trap control molecule.

TABLE 1

Figure 5B:
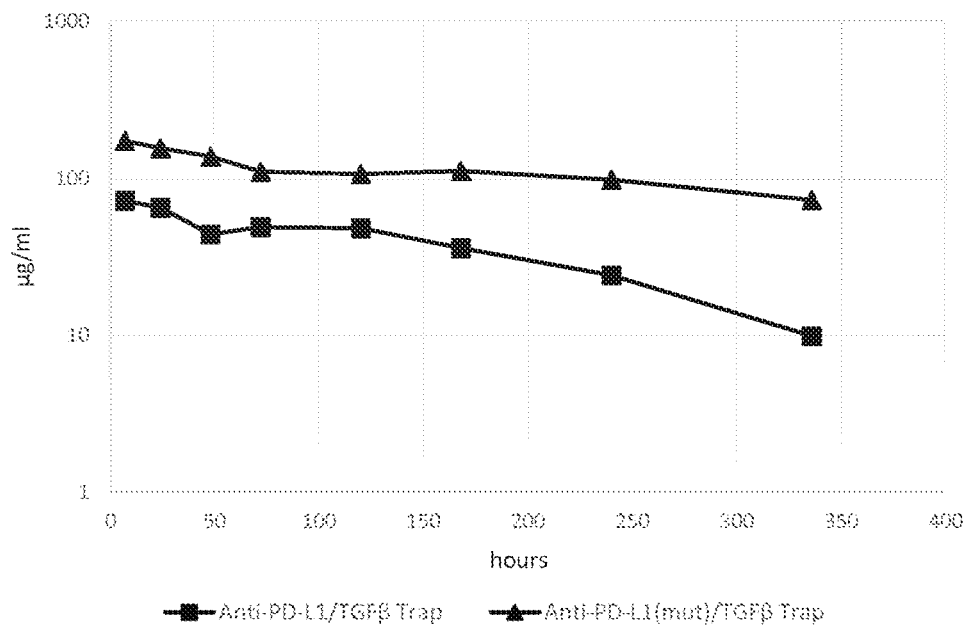

Exposures of anti-PD-L1/TGFβ Trap and the anti-PD-L1(mut)/TGFβ Trap control as determined by the area under the curve (AUC) in the pharmacokinetics graph in FIG. 5B.

| Time (h) | AUC (h * μg/ml) | |
| --- | --- | --- |
|  | Anti-PD-L1/TGFβ Trap | Anti-PD-L1(mut)/TGFβ Trap |
| 7 | 72 | 173 |
| 24 | 1161 | 2789 |
| 48 | 1306 | 3511 |
| 72 | 1113 | 2968 |
| 120 | 2327 | 5192 |
| 168 | 2014 | 5225 |
| 240 | 2159 | 7530 |
| 336 | 1629 | 8188 |
| total | 11781 | 35575 |

Example 6 PD-L1 Target-Mediated Endocytosis of Anti-PD-L1/TGFβ Trap

Figure 6A:
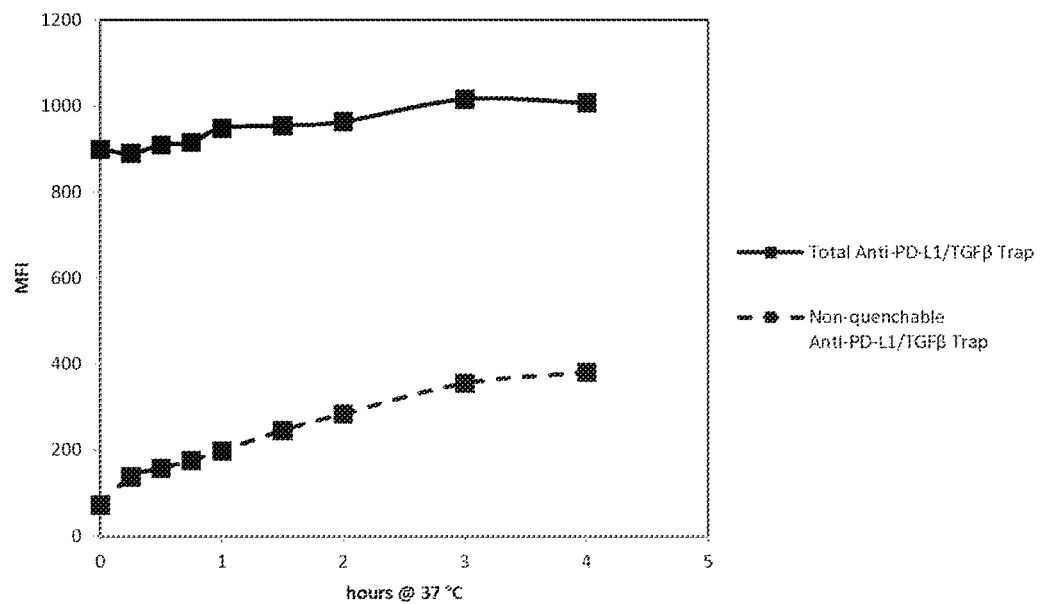
FIG. 6A is a graph showing PD-L1 target-mediated endocytosis of anti-PD-L1/TGFβ Trap.
Figure 6B:
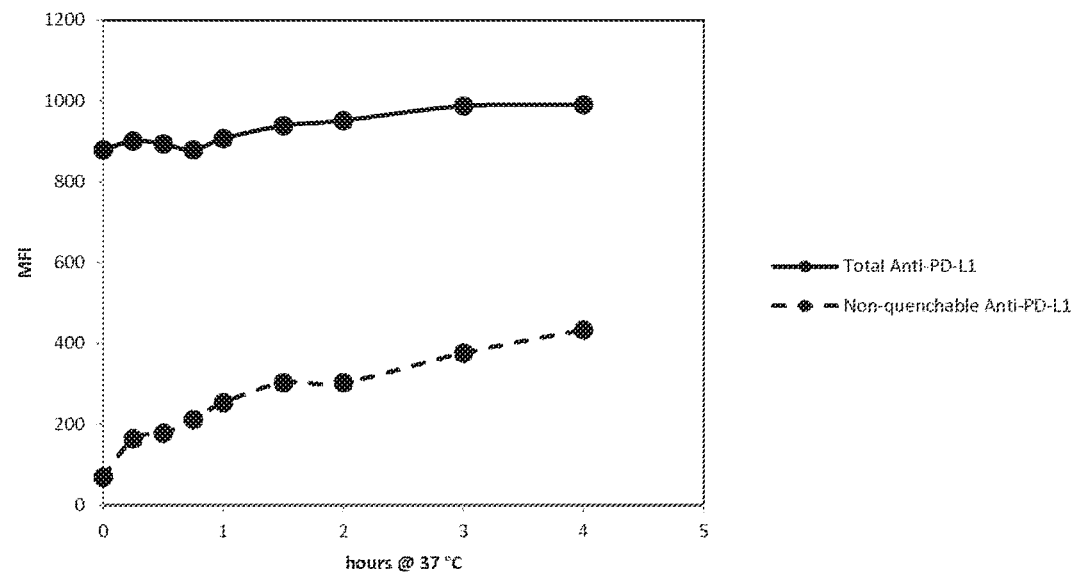
FIG. 6B is a graph showing PD-L1 target-mediated endocytosis of anti-PD-L1.
Figure 6C:
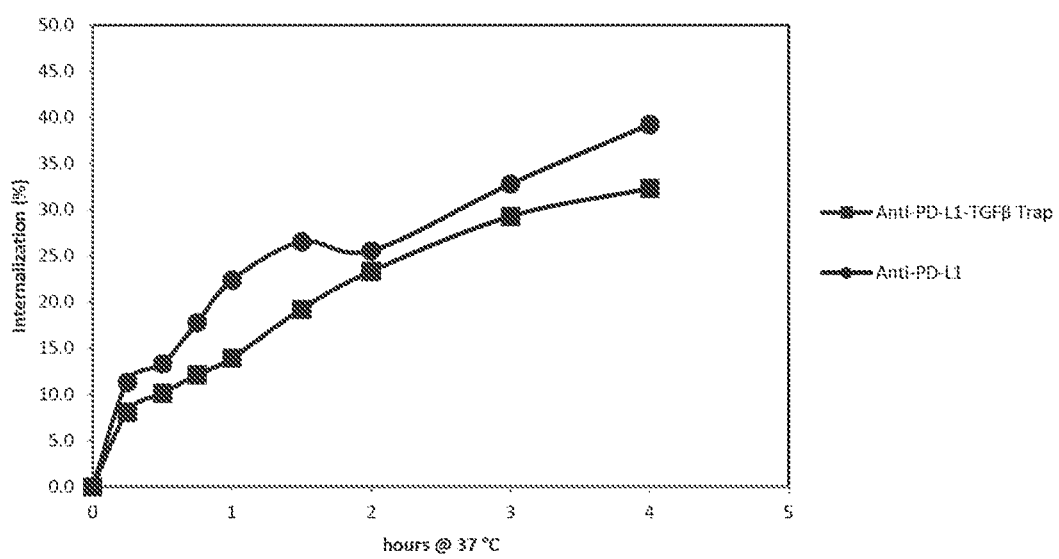
FIG. 6C is a graph showing percent internalization of anti-PD-L1/TGFβ Trap and anti-PD-L1 bound on HEK/PD-L1 cells.

Receptor-mediated endocytosis was studied using the Alexa Fluor 488 quenching techniques according to manufacturer's protocol (Life Technologies, Carlsbad, Calif.). Briefly, HEK cells expressing PD-L1 (HEK/PD-L1 cells) were incubated with 10 μg/ml Alexa Fluor 488-conjugated anti-PD-L1/TGFβ Trap on ice for about 1 hr and washed 4 times with cold media. Washed cells were then pulsed at 37° C. for 0.25, 0.5, 0.75, 1, 1.5, 2, 3 and 4 hr to allow internalization. Cell samples at each time point were then divided into two portions. One portion was incubated on ice and total fluorescence from the Alexa Fluor 488-conjugated anti-PD-L1/TGFβ Trap bound on the cell surface and internalized was measured; the other portion was incubated with anti-Alexa Fluor 488 at 4° C. for about an hour and the non-quenchable fluorescence from the internalized Alexa Fluor 488-conjugated anti-PD-L1/TGFβ Trap was measured. A graph showing a time course of the non-quenchable and total mean fluorescence intensity (MFI) of anti-PD-L1/TGFβ Trap at 37° C. is shown in FIG. 6A. The receptor-mediated internalization kinetics is very similar to that of the anti-PD-L1 antibody, which is shown in FIG. 6B. The percentage of receptor-mediated internalization of anti-PD-L1/TGFβ Trap and anti-PD-L1 on HEK/PD-L1 cells at various time points at 37° C. is shown in FIG. 6C, using the following formula to account for the fact that the quenching by the anti-Alexa Fluor 488 is not 100%:

Internalized fluorescence=Total MFI−(Total MFI Non−quenchable MFI)/Quenching efficiency Example 7 Anti-PD-L1/TGFβ Trap Demonstrated a Superior Anti-Tumor Effect that is Synergistic of Anti-PD-L1 and TGFβ Trap Activities in the EMT-6 (Breast Carcinoma) Subcutaneous Model 8-12 week old female Jh (Igh-J$^{tm1Dhu}$) Balb/C mice (Taconic Farms, Hudson, N.Y.) were inoculated with 0.5× 10$^6$ viable EMT6 cells in 0.1 ml PBS on the right flanks subcutaneously. About five days later, when tumors reached an average size of 20-30 mm$^3$, mice were sorted into groups (N=10) so that the average tumor sizes of all groups were similar, and treatment by intravenous injections was initiated (Day 0). Group 1 received 400 μg of isotype antibody control three times weekly (or "eod" (every other day); Group 2 received 400 μg of anti-PD-L1 antibody three times weekly; Group 3 received 164 μg of anti-PD-L1(mut)/TGFβ Trap three times weekly; Group 4 received 492 μg of anti-PD-L1/TGFβ Trap three times weekly; Group 5 received 492 μg of anti-PD-L1/TGFβ Trap twice weekly (equimolar to 400 μg of anti-PD-L1 antibody); Group 6 received 164 μg of anti-PD-L1/TGFβ Trap three times weekly; and Group 7 received 55 μg of anti-PD-L1/TGFβ Trap three times weekly. Body weights were measured twice weekly to monitor toxicity. Tumor volumes were determined at different time points using the formula: tumor volume (mm$^3$)=length×width×height×0.5236. Any mice with tumors over 2500 mm$^3$ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 7A:
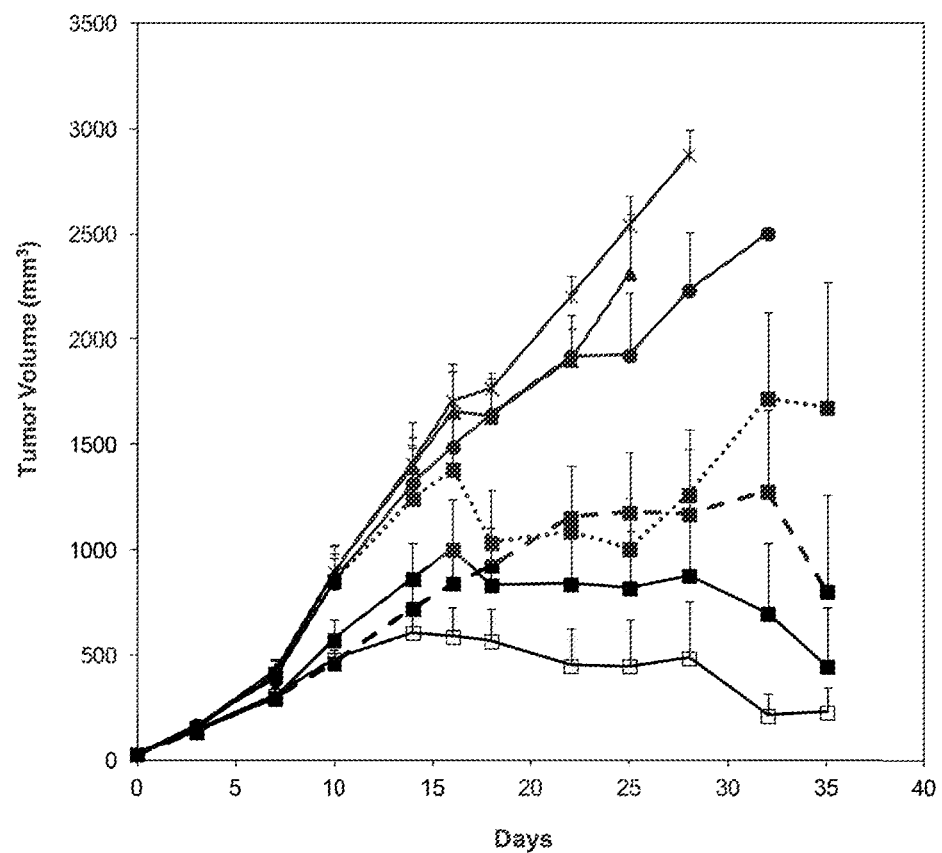
FIGS. 7A-7C are graphs showing anti-tumor efficacy of anti-PD-L1/TGFβ Trap and related proteins in the EMT-6 breast carcinoma subcutaneous model (Example 7).
Figure 7B:
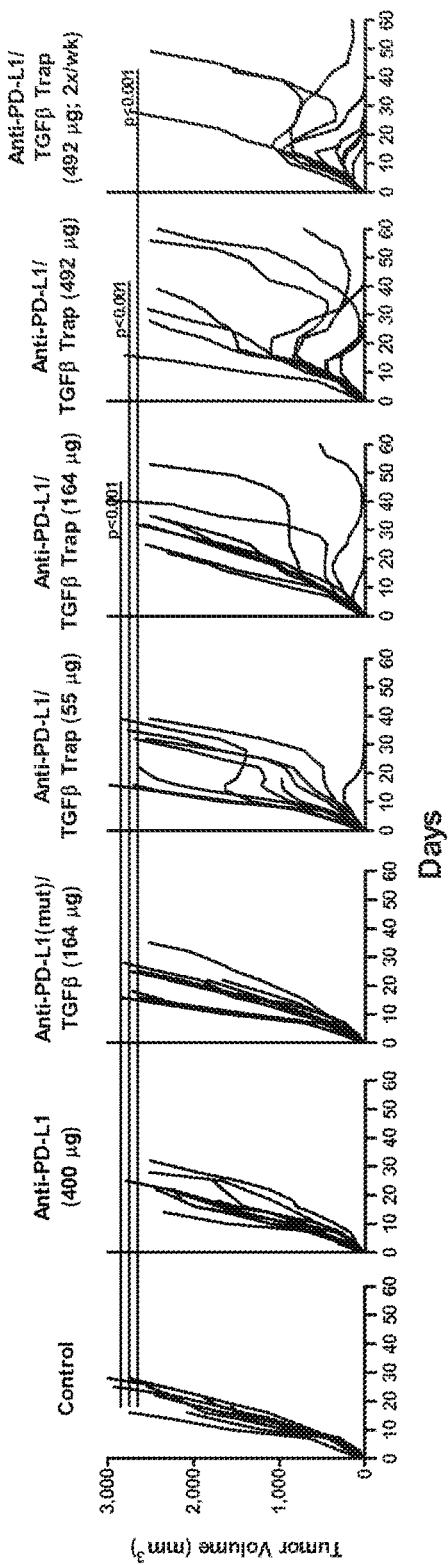
Figure 7C:
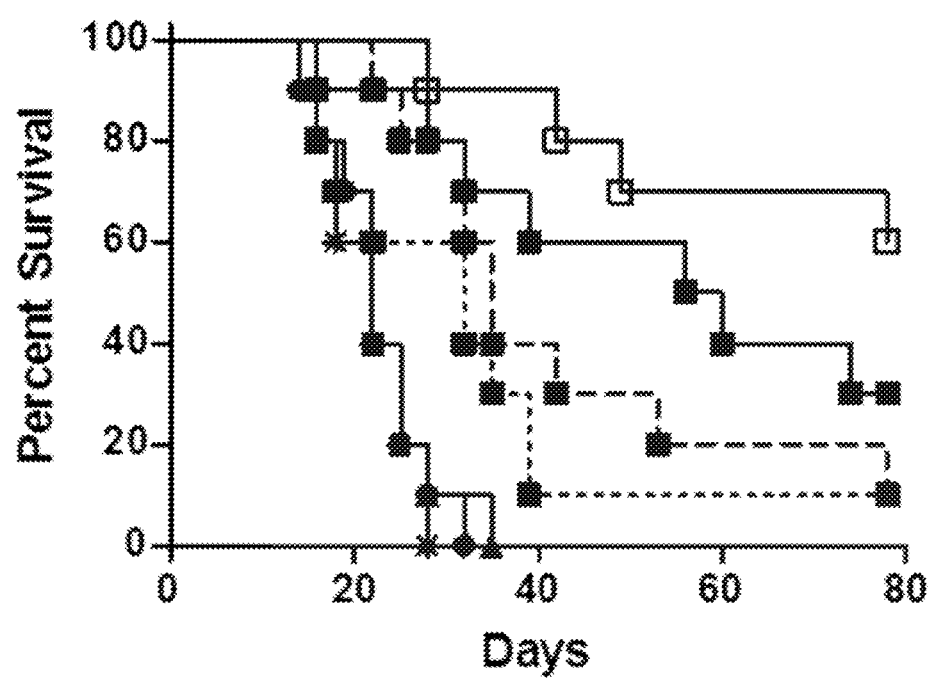

All the treatments were well tolerated. The inhibition of tumor growth by the various treatments is shown in FIG. 7A, which showed the average tumor volumes of the surviving mice, and FIG. 7B, which showed the individual tumor volume of the surviving mice, noting that mice with tumors over 2500 mm$^3$ had to be euthanized. Anti-PD-L1/TGFβ Trap demonstrated potent anti-tumor efficacy, achieving T/C ratios of 0.30, 0.40, and 0.44 for the high (492 μg, Group 4), medium (164 μg, Group 6), and low (55 μg, Group 7) dose groups, respectively on Day 28). While the anti-PD-L1 antibody (Group 2, T/C=0.87, p>0.05, on Day 16, the last day for which the average tumor volume of all the mice were available, i.e., before mice with tumors over 2500 mm$^3$ were euthanized) or the TGFβ Trap control (Group 2, T/C=0.97 on Day 16, p>0.05) alone had marginal efficacy in this model, combining the two agents in a single molecule resulted in profound synergistic anti-tumor effect. This is evident in the median survival times observed for the 492 μg dose (58 and greater than 80 days, respectively, for three times weekly dosing and twice weekly dosing) and 164 μg dose (35 days) of the fusion protein (log rank test: p<0.0001) (FIG. 7C). Importantly, anti-PD-L1/TGFβ Trap at the medium dose of 164 μg (Group 6), with a median survival of 35 days, was far more efficacious than the same dose of anti-PD-L1(mut)/TGFβ Trap (Group 3) or three times the equivalent dose of anti-PD-L1 (Group 2), both of which yielded a median survival of 22 days, respectively (log rank test: p<0.0001). This synergistic anti-tumor activity is especially striking because the exposure of the TGFβ Trap moiety of the 164 μg dose of PD-L1(mut)/TGFβ Trap should be about 3 times higher than that of the 164 μg dose of PD-L1/TGFβ Trap due to receptor-mediated clearance of the latter (see Examples 5 and 6). It is remarkable that tumors in mice which received the high dose of anti-PD-L1/TGFβ Trap continued to regress after dosing was stopped on Day 18 (3 of 10 from Group 4 and 6 of 10 from Group 5 with complete regressions at day 78), demonstrating the long-lasting immunologic anti-tumor effect of targeting the two immunosuppressive mechanisms simultaneously (FIG. 7C). It is also noteworthy that the efficacy for Group 4 is not any better than that of Group 5, suggesting that the dose of 492 μg administered twice weekly was near the saturating dose, or was a more optimal dosing regimen than the 492 µg administered three times weekly.

The protective effect of the anti-tumor immunity elicited by the anti-PD-L1/TGFβ Trap treatment was evident when the mice with tumors in complete regression were challenged with 25,000 viable EMT6 cells injected subcutaneously. While all ten nave mice in a control group developed tumors to an average tumor volume of 726 mm³ by Day 18 post challenge, none of the eleven mice previously treated with PD-L1/TGFβ Trap (three from Group 4, six from Group 5, and one each from Groups 6 and 7) showed any sign of tumor growth.

Example 8 Anti-PD-L1/TGF-β Trap Showed Profound Synergistic Anti-Tumor Activity in the MC38 (Colorectal Carcinoma) Subcutaneous Tumor Model 8-12 week old female B6.129S2-Ighm$^{tm1Cgn}$/J mice (Jackson Laboratory, Bar Harbor, Me.) were injected with 0.5×10⁶ viable MC38 tumor cells in 0.1 ml PBS subcutaneously into the right flank. About eight days later, when average tumor size reached about 80-100 mm³, mice were sorted into groups (N=10) so that the average tumor sizes of all groups were similar, and treatment by intravenous injections was initiated (Day 0). Group 1 received 400 µg of isotype antibody control; Group 2 received 400 µg of anti-PD-L1 antibody; Group 3 received 133 µg of anti-PD-L1 antibody; Group 4 received 492 µg of anti-PD-L1(mut)/TGFβ Trap; Group 5 received 164 µg of anti-PD-L1(mut)/TGFβ Trap; Group 6 received 492 µg of anti-PD-L1/TGFβ Trap; and Group 7 received 164 µg of anti-PD-L1/TGFβ Trap. The treatment was administered three times weekly for two weeks. Body weights were measured twice weekly to monitor toxicity. Tumor volumes were determined at different time points using the formula: tumor volume (mm³)=length×width×height×0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 8:
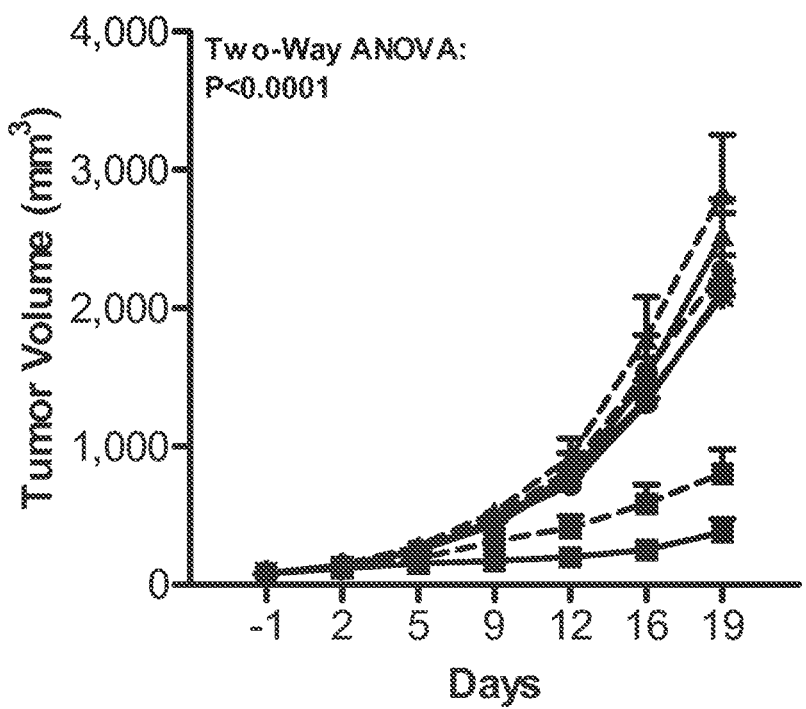
FIG. 8 is a graph showing anti-tumor efficacy of anti-PD-L1/TGFβ Trap and related proteins in the MC38 colorectal carcinoma subcutaneous tumor model (Example 8; star: Group 1; filled circle: Group 2; filled circle/dashed line: Group 3; filled triangle: Group 4; filled triangle/dashed line: Group 5; filled square: Group 6; filled square/dashed line: Group 7).

All the treatments were well tolerated. The inhibition of tumor growth by the various treatments is shown in FIG. 8. On day 19 of the study, anti-PD-L1/TGFβ Trap demonstrated potent dose-dependent anti-tumor efficacy, achieving T/C ratios of 0.18 (p<0.001) and 0.38 (p<0.001) for the high (492 µg, Group 6) and low (164 µg, Group 7) dose groups, respectively. On the other hand, neither anti-PD-L1 or anti-PD-L1(mut)/TGFβ Trap showed any anti-tumor activity at all. Therefore, a profound synergistic anti-tumor activity was obtained when the anti-PD-L1 antibody and the TGFβ Trap moiety were combined into one molecule to target these two immunosuppressive mechanisms simultaneously.

Example 9 Anti-PDL1/TGFβ Trap was Effective in the EMT-6 Orthotopic Model of Metastatic Breast Cancer 8-12 week old female Jh (Igh-J$^{tm1Dhu}$) Balb/C mice (Taconic Farms, Hudson, N.Y.) were inoculated with 0.25× 10⁶ viable EMT6 cells in 0.1 ml PBS into the right mammary pad. About a week later, when average tumor size reached about 50 mm³, mice were sorted into groups (N=10) so that the average tumor sizes of all groups were similar, and treatment by intravenous injections was initiated (Day 0). Group 1 received 133 µg of isotype antibody control; Group 2 received 133 µg of anti-PD-L1 antibody; Group 3 received 164 µg of anti-PD-L1 (mut)/TGFβ Trap; Group 4 received 164 µg of anti-PD-L1/TGFβ Trap; and Group 5 received a combination of 133 µg of anti-PD-L1 and 164 µg of anti-PD-L1(mut)/TGFβ Trap. Treatment was repeated on Days 0, 2, 4, 7, 9, 11 (i.e. 3 times weekly for two weeks). Body weights were measured twice weekly to monitor toxicity. Tumor volumes were determined at different time points using the formula: tumor volume (mm³)=length×width×height×0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 9:
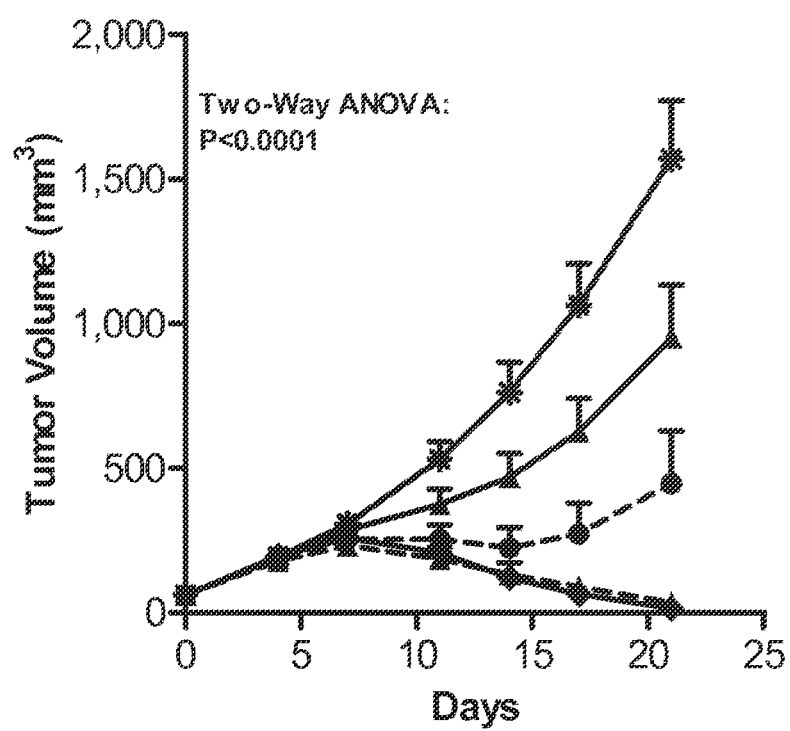
FIG. 9 is a graph showing anti-tumor efficacy of anti-PDL1/TGFβ Trap and related proteins in an orthotopic EMT-6 breast cancer model (Example 9; star: Group 1; filled circle/dashed line: Group 2; filled triangle: Group 3; filled triangle/dashed line: Group 4; filled diamond: Group 5).

All treatments were well tolerated. The inhibition of tumor growth by the various treatments is shown in FIG. 9. Anti-PD-L1/TGFβ Trap demonstrated potent anti-tumor efficacy, achieving T/C ratio of 0.03 (p<0.001) on Day 21. On the other hand, equimolar doses of anti-PD-L1 or anti-PD-L1(mut)/TGFβ Trap were less efficacious, giving T/C ratios of 0.31 (p<0.001 vs. Group 1; p<0.001 vs. Group 4) and 0.68 (p<0.001 vs. Group 1; p<0.001 vs. Group 4), respectively. The combination therapy of equimolar doses of anti-PD-L1 and anti-PD-L1(mut)/TGFβ Trap achieved almost identical anti-tumor efficacy as the fusion protein, although the exposure of the TGFβ Trap of the fusion protein (Group 4) was estimated to be about 3-fold lower than that of the anti-PD-L1(mut)/TGFβ Trap in the combination (Group 5) based on pharmacokinetics analysis (see Example 5). It is also remarkable that the tumors in Groups 4 and 5 continued to regress after the last day of dosing, e.g., average tumor size decreased from 212 mm³ on Day 11, the last day of dosing, to 26 mm³ on Day 24 for anti-PD-L1/TGFβ Trap treatment, demonstrating the long-lasting immunologic anti-tumor effect of targeting the two immunosuppressive mechanisms simultaneously.

Example 10—Anti-PD-L1/TGFβ Trap has Better Anti-Tumor Efficacy than the Combination of Anti-PD-L1 and TGFβ Trap in an Intramuscular MC38 Colorectal Carcinoma Model 8-12 week old female B6.129S2-Ighm$^{tm1Cgn}$/J mice (Jackson Laboratory, Bar Harbor, Me.) were injected with 0.5×10⁶ viable MC38 tumor cells in 0.1 ml PBS intramuscularly in the right thigh. About a week later, when average tumor size reaches about 50 mm³, mice were sorted into groups (N=8) so that the average tumor sizes of all groups were similar, and treatment by intravenous injections was initiated (Day 0) and repeated again two days later (Day 2). Group 1 received 400 µg of isotype antibody control; Group 2 received 400 µg of anti-PD-L1 antibody; Group 3 received 133 µg of anti-PD-L1 antibody; Group 4 received 164 µg of anti-PD-L1(mut)/TGFβ Trap; Group 5 received 492 µg of anti-PD-L1/TGFβ Trap; Group 6 received 164 µg of anti-PD-L1/TGFβ Trap; and Group 7 received a combination of 133 µg of anti-PD-L1 and 164 µg of anti-PD-L1(mut)/TGFβ Trap. Body weights were measured twice weekly to monitor toxicity. Tumor volumes were determined at different time points using the formula: tumor volume (mm³)=length×width×height×0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 10:
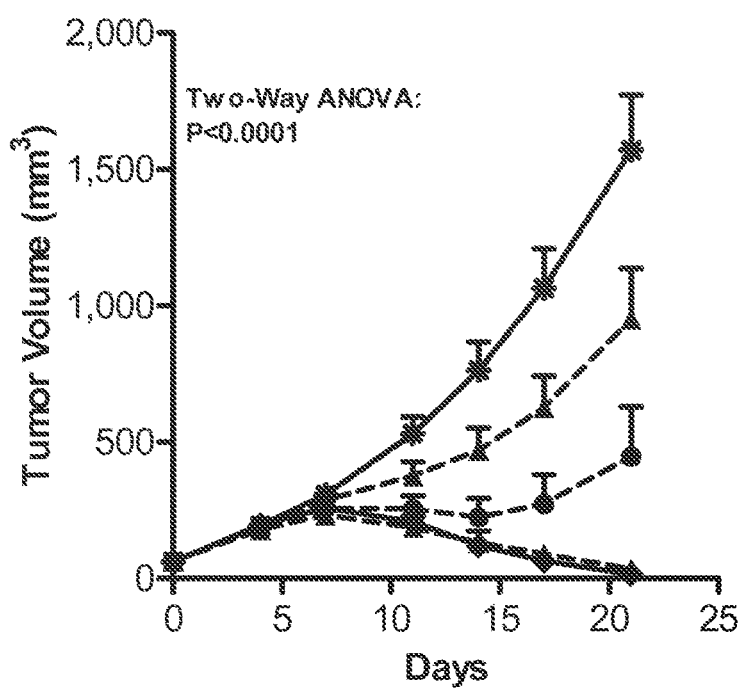
FIG. 10 is a graph showing anti-tumor efficacy of anti-PDL1/TGFβ Trap and related proteins in an intramuscular MC38 colorectal carcinoma model (Example 10; star: Group 1; filled circle: Group 2; filled circle/dashed line: Group 3; filled diamond/dashed line: Group 4; filled square: Group 5; filled square/dashed line: Group 6; filled diamond: Group 7).
Figure 11:
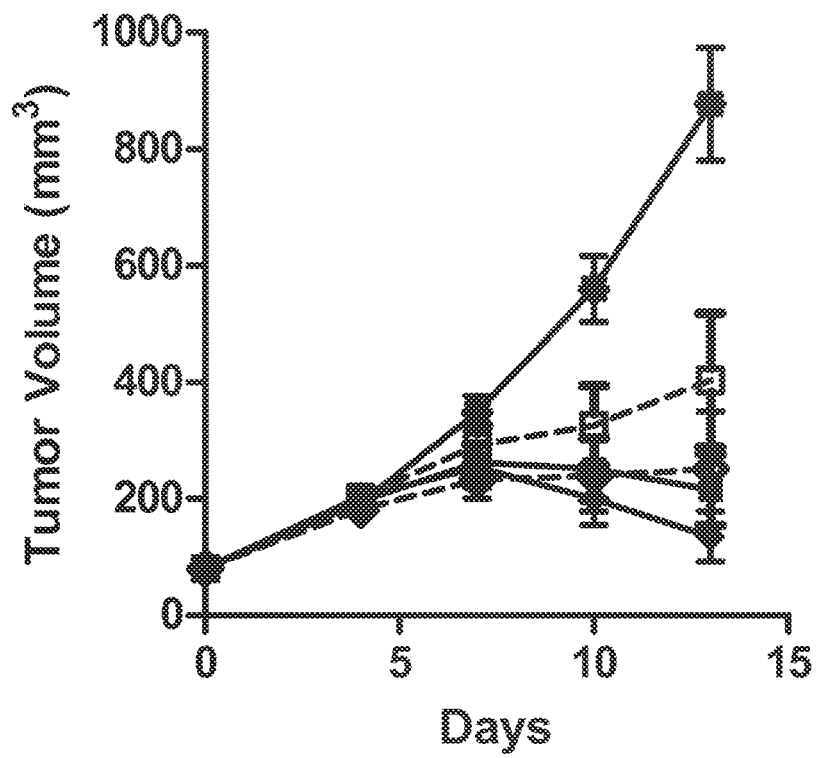
FIG. 11 is a graph showing anti-tumor efficacy of anti-PD-L1/TGF-β Trap and the combination of anti-PD-L1 and TGFβ Trap control administered to give equivalent in vivo exposure in an orthotopic EMT-6 breast tumor model (Example 11; star: Group 1; filled square: Group 2; open square: Group 3; filled diamond: Group 4; open diamond: Group 5).

All the treatments were well tolerated. The inhibition of tumor growth by the various treatments is shown in FIG. 10. Anti-PD-L1/TGFβ Trap demonstrated very potent anti-tumor efficacy, achieving T/C ratios of 0.024 (p<0.001) and 0.052 (p<0.001) for the high (492 µg, Group 5) and low (164 µg, Group 6) dose groups, respectively, on Day 15. On the other hand, equimolar doses of anti-PD-L1 were less efficacious, giving T/C ratios of 0.59 (p<0.001) and 0.45 (p<0.001) for the high (400 µg, Group 2) and low (133 µg, Group 3) dose groups, respectively. Anti-PD-L1(mut)/TGFβ Trap at164 µg (Group 4) was completely ineffective, and it should be pointed out that although this dose is equimolar with the low dose anti-PD-L1/TGFβ Trap group (Group 6), the exposure of the TGFβ Trap should be fairly similar to that of the high dose anti-PD-L1/TGFβ Trap group (Group 5) because of the differences in pharmacokinetics (see Example 5). Therefore, the data demonstrated that anti-PD-L1/TGFβ Trap had potent synergistic anti-tumor activity in this model. It is especially noteworthy that, anti-PD-L1/TGFβ Trap was more efficacious than the combination therapy of equimolar doses of anti-PD-L1 and anti-PD-L1 (mut)/TGFβ Trap, which had a T/C ratio of 0.16 (p<0.001 vs. Group 1 and p>0.05 vs. Group 6) despite a higher TGFβ Trap exposure of about threefold (see Example 5). In addition, anti-PD-L1/TGFβ Trap treatment resulted in 4 out of 10 mice with complete tumor regression, while the combination of anti-PD-L1 and the Trap control induced complete regression in only 2 out of 10 mice (data not shown). It is also remarkable that the tumors in the mice treated with anti-PD-L1/TGFβ Trap continued to regress after the last day of dosing on day 2, and stayed completely regressed thereafter (until at least Day 102), demonstrating the profound and long-lasting immunologic anti-tumor effect of this fusion protein. Without being bound by theory, the data supports a mechanism in which the anti-PD-L1/TGFβ Trap fusion protein not only exploits the synergistic effect of blocking the two major immune escape pathways, but is superior to the combination therapy due to the targeting of the tumor microenvironment by a single molecular entity. Many immunosuppressive cytokines secreted by tumor cells or subverted immune cells (e.g. tumor associated macrophages, myeloid-derived suppressor cells) have autocrines or paracrine functions. Therefore, anti-PD-L1/TGFβ Trap has the capability to deliver the TGFβ Trap to the tumor microenvironment via binding to PD-L1+ tumor cells, where the Trap neutralizes the locally secreted TGFβ. In addition, instead of acting just like a sink for bound TGFβ that accumulates in circulation, anti-PD-L1/TGFβ Trap bound TGFβ could be effectively destroyed through the PD-L1 receptor-mediated endocytosis (Examples 5 and 6).

Example 11 Treatment with Anti-PDL1/TGFβ Trap or the Combination of Anti-PD-L1 and TGFβ Trap Control at Equivalent Exposure in the EMT-6 Orthotopic Model of Metastatic Breast Cancer At equimolar doses, anti-PDL1/TGFβ Trap had similar efficacy as the combination of anti-PD-L1 and TGFβ Trap control in the orthotopic EMT-6 breast cancer model (Example 9). In the following study the efficacy of anti-PDL1/TGFβ Trap or the combination of anti-PD-L1 and TGFβ Trap control administered for equivalent exposure was tested.

8-12 week old female Jh (Igh-J$^{tm1Dhu}$) Balb/C mice (Taconic Farms, Hudson, N.Y.) were inoculated with 0.25× 10$^6$ viable EMT6 cells in 0.1 ml PBS into the right mammary pad. About a week later, when average tumor size reached about 80 mm$^3$, mice were sorted into groups (N=12) so that the average tumor sizes of all groups were similar, and treatment by intravenous injections was initiated on Day 0 and repeated 7 days later. Group 1 received 133 µg of isotype antibody control; Group 2 received 164 µg of anti-PD-L1/TGFβ Trap; Group 3 received 55 µg of anti-PD-L1/TGFβ Trap; Group 4 received a combination of 133 µg of anti-PD-L1 and 55 µg of anti-PD-L1(mut)/TGFβ Trap; and Group 5 received a combination of 44.3 µg of anti-PD-L1 and 18.3 µg of anti-PD-L1(mut)/TGFβ Trap. Body weights were measured twice weekly to monitor toxicity. Tumor volumes were determined at different time points using the formula: tumor volume (mm$^3$)=length×width×height×0.5236. Any mice with tumors over 2500 mm$^3$ were sacrificed following the institute's animal health protocol. Anti-tumor efficacy is reported as a T/C ratio, where T and C are the average tumor volumes of the group treated with antibody or fusion protein, and the group treated with the isotype control, respectively.

All the treatments were well tolerated. Anti-PD-L1/TGFβ Trap and the combination therapy demonstrated potent anti-tumor efficacy at both dose levels tested.

Example 12 Anti-PD-L1/TGF-β Trap has Better Antitumor Efficacy than the Combination of Anti-PD-L1 and TGFβ Trap Administered to Give Equivalent Exposure in an Intramuscular MC38 Colorectal Carcinoma Model The results in Example 10 suggested that at equimolar doses the anti-PD-L1/TGF-β Trap has better antitumor efficacy than the combination of anti-PD-L1 and TGFβ Trap control even though the in vivo exposure of anti-PD-L1 (mut)/TGFβ Trap control is about 3 times that of anti-PD-L1/TGFβ Trap (Example 5). In a follow-up study the anti-tumor efficacy of anti-PD-L1/TGFβ Trap and the combination of anti-PD-L1 and anti-PD-L1(mut)/TGFβ Trap based on equal exposure was compared. Lower doses than in Example 10 were administered to avoid dosing near saturating levels.

8-12 week old female B6.129S2-Ighm$^{tm1Cgn}$/J mice (Jackson Laboratory, Bar Harbor, Me.) were injected with 0.5×10$^6$ viable MC38 tumor cells in 0.1 ml PBS intramuscularly in the right thigh. A week later, when average tumor size reached about 200 mm$^3$, mice were sorted into groups (N=12) so that the average tumor sizes of all groups were similar. Treatment by intravenous injections was initiated (Day 0) and repeated again on Day 4. Group 1 received 133 µg of isotype antibody control; Group 2 received 164 µg of anti-PD-L1/TGFβ Trap; Group 3 received 55 µg of anti-PD-L1/TGFβ Trap; Group 4 received a combination of 133 µg of anti-PD-L1 and 55 µg of anti-PD-L1(mut)/TGFβ Trap; and Group 5 received a combination of 44.3 µg of anti-PD-L1 and 18.3 µg of anti-PD-L1(mut)/TGFβ Trap. Body weights were measured twice weekly to monitor toxicity. Tumor volumes were determined at different time points using the formula: tumor volume (mm$^3$)=length×width×height×0.5236. Any mice with tumors over 2500 mm$^3$ were sacrificed following the institute's animal health protocol. Anti-tumor efficacy is reported as a T/C ratio, where T and C are the average tumor volumes of the group treated with antibody or fusion protein, and the group treated with the isotype control, respectively.

Figure 12A:
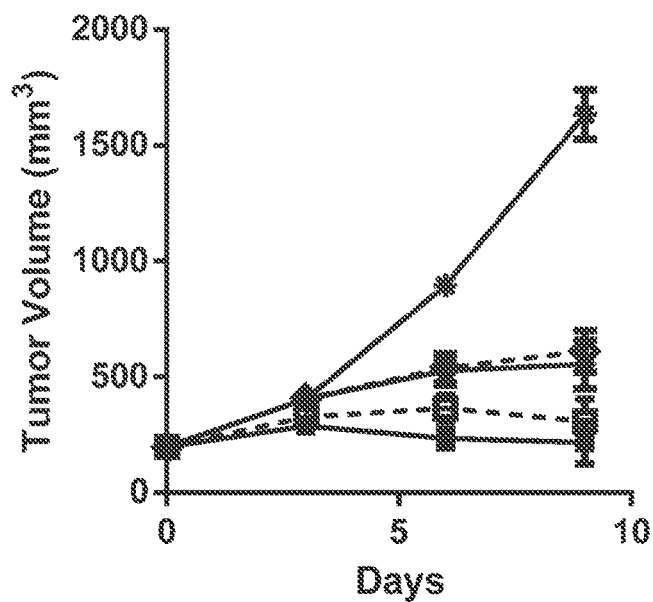
FIGS. 12A-12C are graphs showing anti-tumor efficacy of anti-PD-L1/TGF-β Trap and the combination of anti-PD-L1 and TGFβ Trap control administered to give equivalent in vivo exposure in an intramuscular MC38 colorectal carcinoma model (Example 12).
Figure 12B:
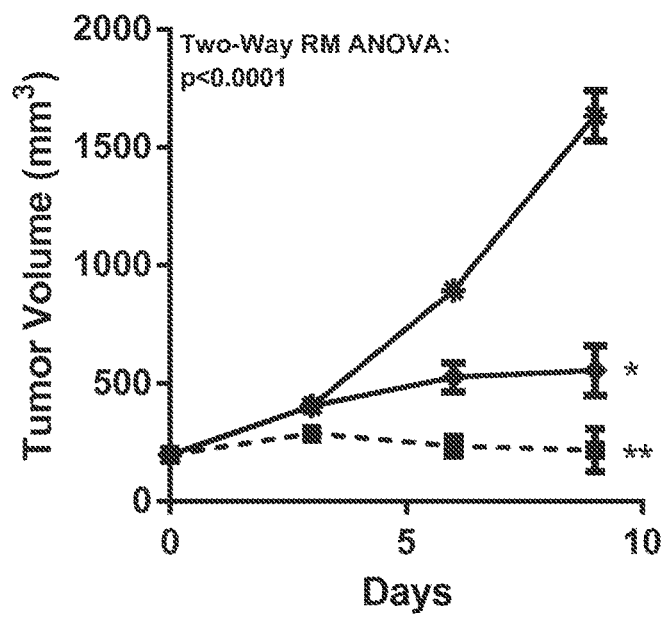
Figure 12C:
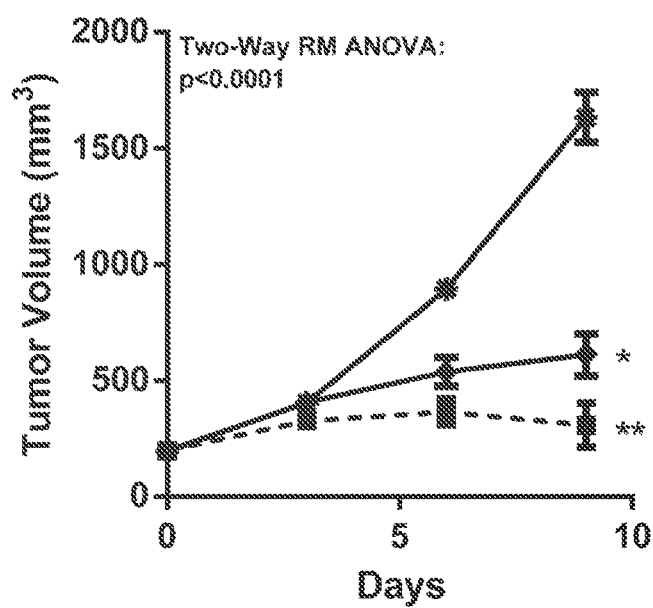

All the treatments were well tolerated. Anti-PD-L1/TGFβ Trap demonstrated very potent anti-tumor efficacy, achieving T/C ratios of 0.13 (p<0.001) and 0.19 (p<0.001) for the intermediate (164 ng, Group 2, called intermediate dose relative to the high dose of 492 ng that seemed to be saturating in Example 10) and low (55 ng, Group 3) dose groups, respectively, on Day 9. On the other hand, the combination of anti-PD-L1 and anti-PD-L1(mut)/TGFβ Trap were less efficacious, giving T/C ratios of 0.34 (p<0.001) and 0.37 (p<0.001) for the intermediate (Group 4) and low (Group 5) dose groups, respectively (FIG. 12A or Table). It is especially noteworthy that when administered to give equivalent in vivo exposure of the anti-PD-L1 antibody and the TGFβ Trap component, anti-PD-L1/TGFβ Trap was significantly more efficacious than the combination therapy of anti-PD-L1 and anti-PD-L1(mut)/TGFβ Trap at both dose levels (at the intermediate dose, T/C of 0.13 for anti-PD-L1/TGFβ Trap vs. 0.34 for the combination p<0.0001 (FIG. 12B); at the low dose, T/C of 0.19 for anti-PD-L1/TGFβ Trap vs. 0.37 for the combination p<0.0001 (FIG. 12C)).

Example 13 Anti-PD-L1(YW)/TGFβ Trap has Superior Anti-Tumor Effect that is Synergistic of Anti-PD-L1 and TGFβ Trap Activities in the EMT-6 (Breast Carcinoma) Orthotopic Model YW243.55S70 is a human antibody that recognizes both human and murine PD-L1 (US Patent Application Publication No. US2010/0203056 A1). Its variable region sequence of the heavy chain (VH) and variable region sequence of the light chain (VL) (provided as SEQ ID NO: 14 and SEQ ID NO: 13, respectively) were used to replace the corresponding variable region sequences of the anti-PD-L1/TGFβ Trap described in Example 1 to give anti-PD-L1(YW)/TGFβ Trap by standard molecular biology techniques. After construction of the DNA coding for anti-PD-L1(YW)/TGFβ Trap, the antibody fusion protein was expressed as described in Example 1. The anti-PD-L1 antibody YW243.55570 is similarly expressed for comparison of efficacy in murine tumor models.

8-12 week old female Jh (Igh-Jtm1Dhu) Balb/C mice (Taconic Farms, Hudson, N.Y.) were inoculated with 0.25× $10^6$ viable EMT6 cells in 0.1 ml PBS into the right mammary pad. About a week later, when average tumor size reached about 50-100 mm³, mice were sorted into groups (N=10) so that the average tumor sizes of all groups were similar, and treatment by intravenous injections was initiated (Day 0). Group 1 received 133 μg of isotype antibody control; Group 2 received 133 μg of anti-PD-L1(YW) antibody; Group 3 received 164 μg of anti-PD-L1(mut)/TGFβ Trap; Group 4 received 164 μg of anti-PD-L1(YW)/TGFβ Trap; and Group 5 received a combination of 133 μg of anti-PD-L1(YW) and 164 μg of anti-PD-L1 (mut)/TGFβ Trap. Treatment was repeated on Days 4 and 7. Body weights were measured twice weekly to monitor toxicity. Tumor volumes were determined at different time points using the formula tumor volume (mm³)=length×width× height×0.5236. Any mice with tumors over 2500 mm³ were sacrificed following the institute's animal health protocol. Anti-tumor efficacy is reported as a T/C ratio, where T and C are the average tumor volumes of the group treated with antibody or fusion protein, and the group treated with the isotype control, respectively.

Figure 13A:
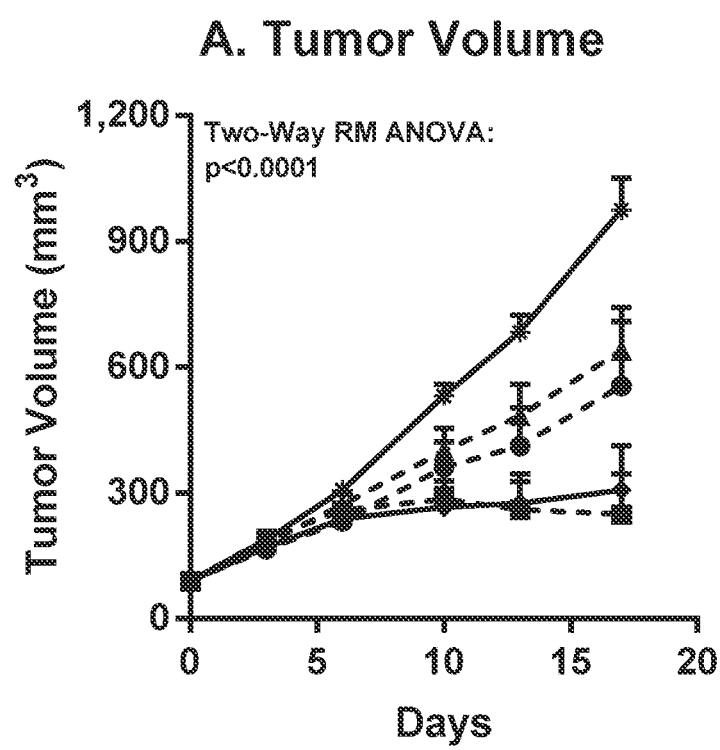
FIGS. 13A-13B are graphs showing anti-tumor efficacy of anti-PD-L1(YW)/TGF-β Trap and related proteins in an orthotopic EMT-6 breast tumor model (Example 13; star: Group 1; filled circle: Group 2; filled triangle: Group 3; filled square: Group 4; filled diamond: Group 5).
Figure 13B:
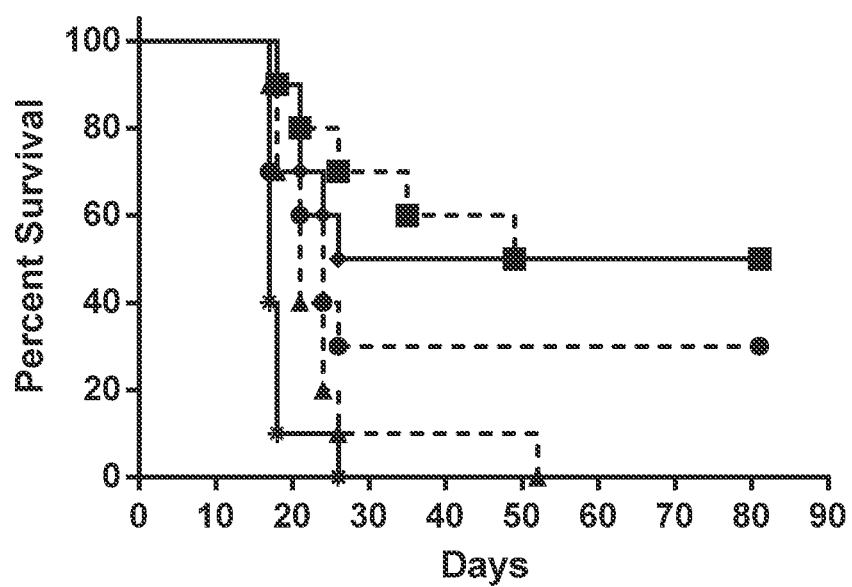

All the treatments were well tolerated. The inhibition of tumor growth by the various treatments is shown in FIG. 13A, which showed the average tumor volumes of the mice on Day 17, the last day for which the average tumor volume of all the mice were available, i.e., before mice with tumors over 2500 mm³ were euthanized. Anti-PD-L1(YW)/TGFβ Trap demonstrated potent anti-tumor efficacy, achieving a T/C ratio of 0.25 (p<0.0001) that is slightly better than that of the combination treatment in Group 5 (T/C=0.31, p<0.0001), but superior to that of the anti-PD-L1(YW) antibody in Group 2 (T/C=0.57, p<0.0001) and the TGFβ Trap control in Group 3 (T/C=0.66, p<0.0001). The synergistic anti-tumor effect of the antibody fusion protein also resulted in prolonged survival of the treated mice, as shown in FIG. 13B. The anti-PD-L1/TGFβ Trap treated group had a median survival time of 65 days, which was significantly better than that of the anti-PD-L1(YW) antibody treated group (24 days) or the TGFβ Trap control treated group (21 days). It also compares favorably with the median survival time of 53.5 days for the combination treatment group. Despite dosing stopped after day 7, the continual tumor growth inhibition and the prolonged survival of the anti-PD-L1(YW)/TGFβ Trap treated mice demonstrate the long-lasting immunologic anti-tumor effect resulting from dual blockade of the two major immunosuppressive pathways.

Example 14 Anti-PD-L1(YW)/TGF-β Trap has Superior Anti-Tumor Effect that is Synergistic of Anti-PD-L1 and TGFβ Trap Activities in the MC38 (Colorectal Carcinoma) Intramuscular Tumor Model 8-12 week old female B6.129S2-Ighm$^{tm1Cgn}$/J mice (Jackson Laboratory, Bar Harbor, Me.) were injected with 0.5×$10^6$ viable MC38 tumor cells in 0.1 ml PBS intramuscularly in the right thigh. About a week later, when average tumor size reaches about 150-200 mm³, mice were sorted into groups (N=10) so that the average tumor sizes of all groups were similar, and treatment by intravenous injections was initiated (Day 0) and repeated again four days later (Day 4). Group 1 received 133 μg of isotype antibody control; Group 2 received 133 μg of anti-PD-L1(YW) antibody; Group 3 received 164 μg of anti-PD-L1(mut)/TGFβ Trap; Group 4 received 164 μg of anti-PD-L1(YW)/TGFβ Trap; and Group 5 received a combination of 133 μg of anti-PD-L1(YW) and 164 μg of anti-PD-L1(mut)/TGFβ Trap. Body weights were measured twice weekly to monitor toxicity. Tumor volumes were determined at different time points using the formula tumor volume (mm³)=length×width× height×0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 14A:
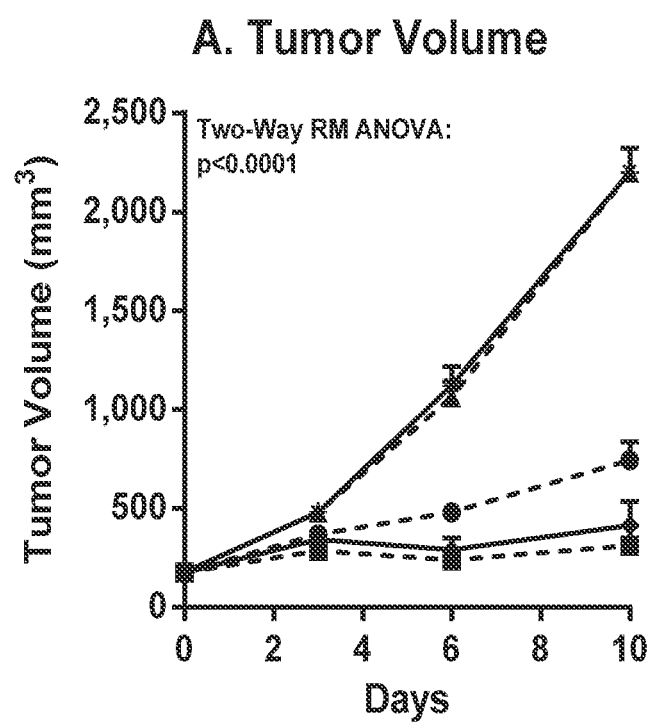
FIGS. 14A-14B are graphs showing anti-tumor efficacy of anti-PD-L1(YW)/TGF-β Trap and related proteins based on (A) tumor volumes and (B) tumor weights, in an intramuscular MC38 colorectal carcinoma model (Example 14; star: Group 1; filled circle: Group 2; filled triangle: Group 3; filled square: Group 4; filled diamond: Group 5).
Figure 14B:
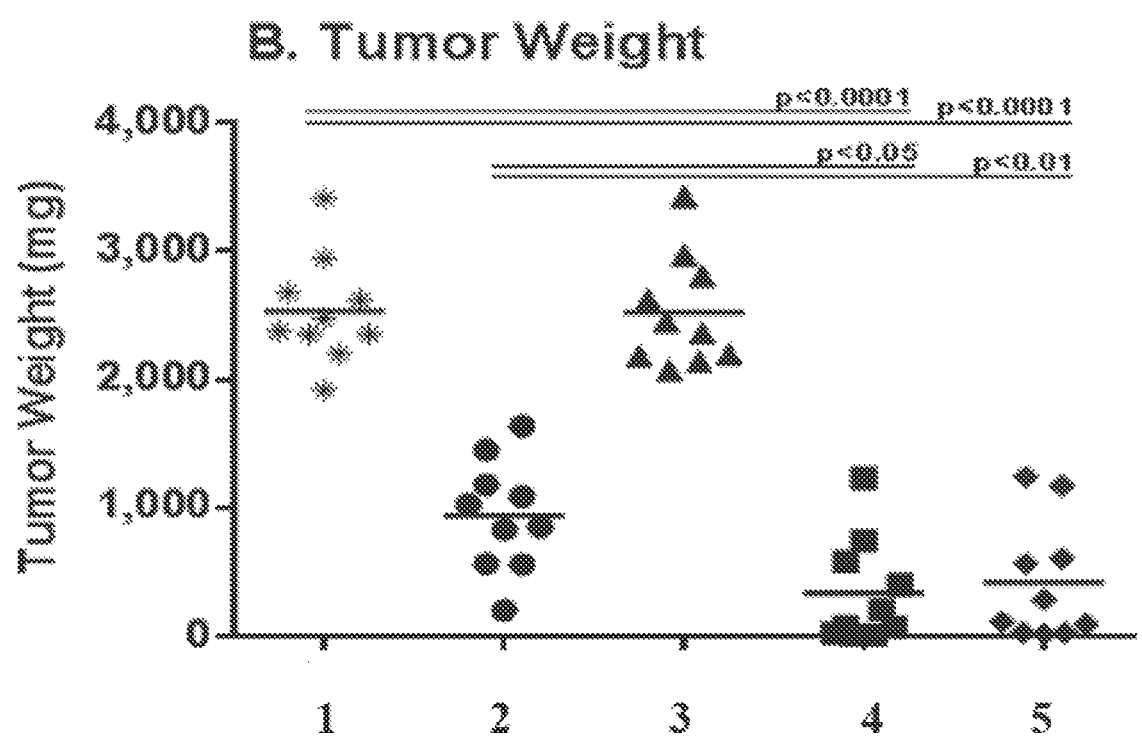

All the treatments were well tolerated. The inhibition of tumor growth by the various treatments is shown in FIG. 14A, which showed the average tumor volumes of the mice on Day 10, the last day for which the average tumor volume of all the mice were available. Anti-PD-L1(YW)/TGFβ Trap demonstrated very potent anti-tumor efficacy, achieving a T/C ratio of 0.14 (p<0.0001) that is slightly better than that of the combination treatment in Group 5 (T/C=0.19, p<0.0001), but superior to that of the anti-PD-L1(YW) antibody in Group 2 (T/C=0.34, p<0.0001) and the TGFβ Trap control in Group 3 (T/C=0.99, p<0.0001), which had no activity in this model. The anti-tumor efficacy of anti-PD-L1(YW)/TGFβ Trap was further confirmed by tumor weight measurements taken on Day 11. By this time, the isotype control group had to be euthanized because the tumors had grown beyond 2500 mm³. Therefore, the experiment was terminated and all the groups were euthanized and the tumor weights determined. The individual tumor weights are shown in FIG. 14B. The analysis of tumor weights confirmed that anti-PD-L1(YW)/TGFβ Trap therapy significantly inhibited MC38 tumor growth (T/C=0.13; p<0.0001). The efficacy of anti-PD-L1(YW)/TGFβ Trap was significantly better than that observed with anti-PD-L1 (T/C=0.37; p=0.003) or the TGFβ Trap control (T/C=1.0, p<0.0001). The anti-tumor efficacy of anti-PD-L1(YW)/TGFβ Trap, based on the tumor weight analysis, was not statistically better than the mice treated with the combination of anti-PD-L1 and the TGFβ Trap control (T/C=0.17; p=0.96).

Example 15 Combination Treatment of Anti-PD-1 and TGFβ Trap do not Provide any Additive Anti-Tumor Effect in an EMT-6 (Breast Carcinoma) Orthotopic Model In this study we tested if the combination treatment of anti-PD-1 and TGFβ Trap provides any additive anti-tumor effect in the EMT-6 orthotopic model. CT-011, also known as pidiluzumab, is a humanized anti-human PD1 antibody that was tested in the clinic for treatment of hematological malignancies (Berger et al, Clin Cancer Res. 2008; 14:3044-3051). It also recognizes murine PD-1 and has shown anti-tumor activity that synergizes with cyclophosphamide and vaccine treatment in syngeneic tumor models (Mkrtichyan et al., Eur J Immunol. 2011; 41:2977-86). The VH and VL sequences of CT-011 were used to produce a recombinant antibody with human IgG1/kappa constant regions by standard molecular biology techniques.

8-12 week old female Jh (Igh-Jtm1Dhu) Balb/C mice (Taconic Farms, Hudson, N.Y.) were inoculated with 0.25× $10^6$ viable EMT6 cells in 0.1 ml PBS into the right mammary pad. About a week later, when average tumor size reached about 100 mm$^3$, mice were sorted into groups (N=10) so that the average tumor sizes of all groups were similar, and treatment by intravenous injections was initiated (Day 0). Group 1 received 364 µg of isotype antibody control; Group 2 received 164 µg of anti-PD-L1(mut)/TGFβ Trap, which served as the TGFβ Trap control; Group 3 received 200 µg of anti-PD-1(CT-011); and Group 4 received a combination of 200 µg of anti-PD-1(CT-011) and 164 µg of anti-PD-L1(mut)/TGFβ Trap control. Treatment was repeated on Days 2, 4, 7, 9, and 11, i.e. 3 times weekly for two weeks. Body weights were measured twice weekly to monitor toxicity. Tumor volumes were determined at different time points using the formula tumor volume (mm$^3$)=length×width×height×0.5236. Any mice with tumors over 2500 mm$^3$ were sacrificed following the institute's animal health protocol. Anti-tumor efficacy was reported as a T/C ratio, where T and C are the average tumor volumes of the group treated with antibody or fusion protein, and the group treated with the isotype control, respectively.

Figure 15:
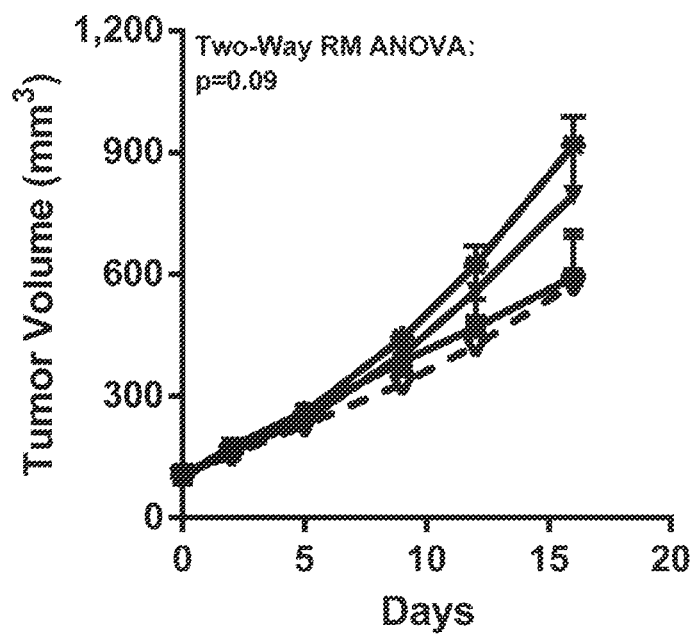
FIG. 15 is a graph comparing the anti-tumor efficacy of an anti-PD-1 antibody treatment with and without TGFβ Trap control in an orthotopic EMT-6 breast tumor model (Example 15; star: Group 1; filled square: Group 2; filled inverted triangle: Group 3; open inverted triangle: Group 4).
Figure 16:
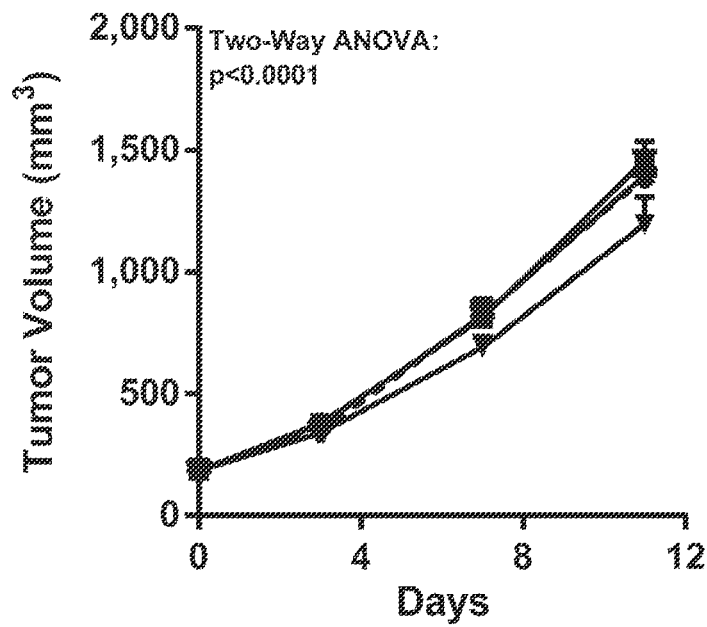
FIG. 16 is a graph comparing the anti-tumor efficacy of an anti-PD-1 antibody treatment with and without TGFβ Trap control in an intramuscular MC38 colorectal tumor model (Example 16; star: Group 1; filled square: Group 2; filled inverted triangle: Group 3; open inverted triangle: Group 4).
Figure 17:
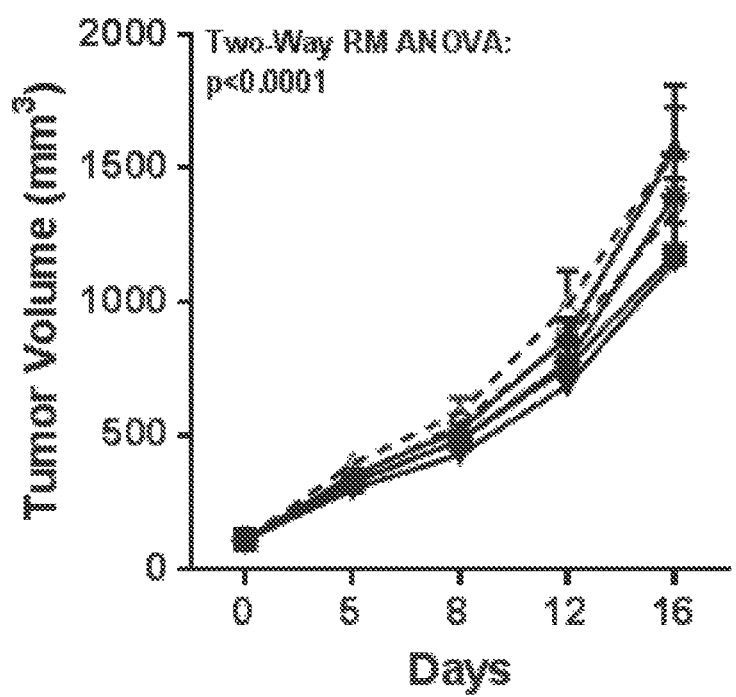
FIG. 17 is a graph comparing the anti-tumor efficacy of an anti-LAG3 or anti-TIM3 antibody treatment with and without TGFβ Trap control in an orthotopic EMT-6 breast tumor model (Example 17; star: Group 1; filled square: Group 2; filled triangle: Group 3; filled inverted triangle: Group 4; open triangle: Group 5; open inverted triangle: Group 6).
Figure 18:
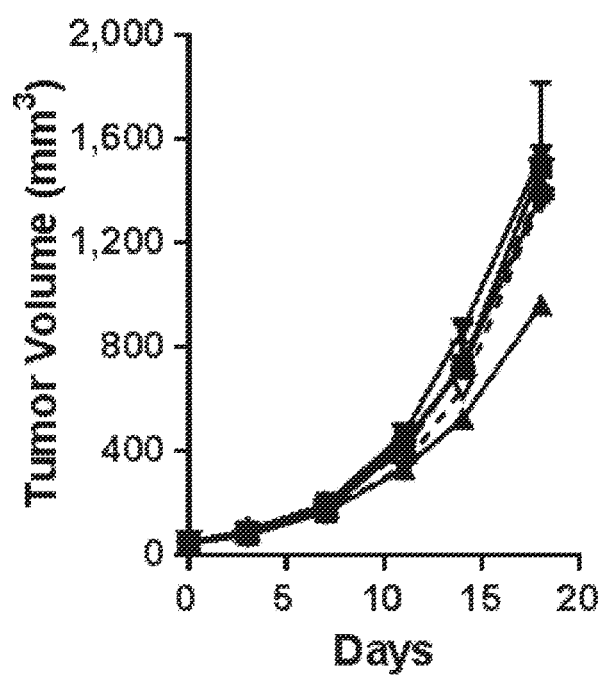
FIG. 18 is a graph comparing the anti-tumor efficacy of an anti-LAG3 or anti-TIM3 antibody treatment with and without TGFβ Trap control in an intramuscular MC38 colorectal tumor model (Example 18; star: Group 1; filled square: Group 2; filled triangle: Group 3; filled inverted triangle: Group 4; open triangle: Group 5; open inverted triangle: Group 6).

All the treatments were well tolerated. Anti-PD-1(CT-011) showed very modest anti-tumor efficacy (T/C=0.87, p>0.05) in this model, while its combination with the TGFβ Trap control had the same efficacy as the TGFβ Trap control alone (FIG. 15).

Example 16 Combination Treatment of Anti-PD-1 and TGFβ Trap do not Provide any Additive Anti-Tumor Effect in an MC38 (Colorectal Carcinoma) Intramuscular Tumor Model In this study we tested if the combination treatment of anti-PD-1 and TGFβ Trap provides any additive anti-tumor effect in the intramuscular MC38 colorectal tumor model. 8-12 week old female B6.129S2-Ighm$^{tm1Cgn}$/J mice (Jackson Laboratory, Bar Harbor, Me.) were injected with 0.5× $10^6$ viable MC38 tumor cells in 0.1 mL PBS intramuscularly in the right thigh. About a week later, when average tumor size reaches about 190 mm$^3$, mice are sorted into groups (N=10) so that the average tumor sizes of all groups are similar, and treatment by intravenous injections is initiated (Day 0). Group 1 received 364 µg of isotype antibody control on Days 0, 2, 4, and 7; Group 2 received 164 µg of the anti-PD-L1(mut)/TGFβ Trap control on Days 0 and 2; Group 3 received 200 µg of anti-PD-1(CT-011) on Days 0, 2, 4, and 7; and Group 4 received a combination of 200 µg of anti-PD-1(CT-011) on Days 0, 2, 4, and 7, and 164 µg of anti-PD-L1(mut)/TGFβ Trap control on Days 0 and 2. Body weights were measured twice weekly to monitor toxicity. Tumor volumes were determined at different time points using the formula tumor volume (mm$^3$)=length×width×height×0.5236. Any mice with tumors over 2500 mm$^3$ were sacrificed following the institute's animal health protocol. Anti-tumor efficacy was reported as a T/C ratio, where T and C are the average tumor volumes of the group treated with antibody or fusion protein, and the group treated with the isotype control, respectively.

All the treatments were well tolerated. Anti-PD-1(CT-011) showed very modest anti-tumor efficacy (T/C=0.87, p>0.05), while the anti-PD-L1(mut)/TGFβ Trap control had no efficacy in this model, as seen in previous examples. The combination of anti-PD-1(CT-011) with the TGFβ Trap control had no efficacy at all (FIG. 15).

Example 17 Combination Treatment of TGFβ Trap with Either Anti-LAG3 or Anti-TIM-3 do not Provide any Additive Anti-Tumor Effect in an EMT-6 (Breast Carcinoma) Orthotopic Model In this study we tested if the combination treatment of TGFβ Trap with either anti-LAG3 or anti-TIM3 provides any additive anti-tumor effect in the orthotopic EMT-6 breast tumor model. The anti-LAG3 antibody used is a rat IgG1 monoclonal anti-murine LAG3 antibody C9B7W (BioXcell, Beverly, Mass.), which was shown to synergize with anti-murine PD-1 treatment in syngeneic tumor models (Woo et al, Cancer Res, 2011; 72:917-27). The anti-TIM-3 antibody used is a rat IgG2a monoclonal anti-murine TIM3 antibody RMT3-23 (BioXcell, Beverly, Mass.), which also was shown to synergize with anti-murine PD-1 treatment in syngeneic tumor models, although its efficacy as a single agent was relatively modest (Ngiow et al, Cancer Res, 2011; 71:3540-51).

8-12 week old female Jh (Igh-Jtm1Dhu) Balb/C mice (Taconic Farms, Hudson, N.Y.) were inoculated with 0.25× $10^6$ viable EMT6 cells in 0.1 ml PBS into the right mammary pad. About a week later, when average tumor size reached about 110 mm$^3$, mice were sorted into groups (N=9) so that the average tumor sizes of all groups were similar, and treatment by intravenous injections was initiated (Day 0). Group 1 received 133 ng of isotype antibody control; Group 2 received 164 ng of the anti-PD-L1(mut)/TGFβ Trap control; Group 3 received 200 ng of anti-LAG3; Group 4 received 250 ng of anti-TIM3; Group 5 received a combination of 200 ng of anti-LAG3 and 164 ng of anti-PD-L1(mut)/TGFβ Trap control; and Group 6 received a combination of 250 ng of anti-TIM3 and 164 ng of anti-PD-L1(mut)/TGFβ Trap control. Treatment was repeated on Days 2, 4, 7, 9, and 11, i.e. 3 times weekly for two weeks. Body weights were measured twice weekly to monitor toxicity. Tumor volumes were determined at different time points using the formula tumor volume (mm$^3$)=length×width× height×0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

As observed previously, the anti-PD-L1(mut)/TGFβ Trap control (Group 2) showed very modest efficacy in this EMT-6 model. Anti-TIM3 (Group 4) as a single agent showed a similarly modest efficacy as the Trap control, and in combination therapy with the Trap control (Group 6) showed no additive effect. Anti-LAG3 either as a single agent (Group 3) or in combination therapy with the Trap control (Group 5) did not show any efficacy.

Example 18 Combination Treatment of TGFβ Trap with Either Anti-LAG3 or Anti-TIM-3 do not Provide any Additive Anti-Tumor Effect in an MC38 (Colorectal Carcinoma) Intramuscular Tumor Model In this study we tested if the combination treatment of TGFβ Trap with either anti-LAG3 (C9B7W) or anti-TIM3 (RMT3-23) provides any additive anti-tumor effect in the intramuscular MC38 colorectal tumor model.

8-12 week old female B6.129S2-Ighm$^{tm1Cgn}$/J mice (Jackson Laboratory, Bar Harbor, Me.) were injected with 0.5×10⁶ viable MC38 tumor cells in 0.1 mL PBS intramuscularly in the right thigh. About a week later, when average tumor size reaches about 50 mm³, mice were sorted into groups (N=8) so that the average tumor sizes of all groups were similar, and treatment by intravenous injections is initiated (Day 0). Group 1 received 133 μg of isotype antibody control; Group 2 received 164 μg of the anti-PD-L1(mut)/TGFβ Trap control; Group 3 received 200 μg of anti-LAG3; Group 4 received 250 μg of anti-TIM3; Group 5 received a combination of 200 μg of anti-LAG3 and 164 μg of anti-PD-L1(mut)/TGFβ Trap control; and Group 6 received a combination of 250 μg of anti-TIM3 and 164 μg of anti-PD-L1(mut)/TGFβ Trap control. Treatment was repeated on Days 2, 4, 7, 9, 11, 15 and 18. Body weights were measured twice weekly to monitor toxicity. Tumor volumes were determined at different time points using the formula tumor volume (mm³)=length×width×height× 0.5236. Any mice with tumors over 2500 mm³ were sacrificed following the institute's animal health protocol. Anti-tumor efficacy was reported as a T/C ratio, where T and C are the average tumor volumes of the group treated with antibody or fusion protein, and the group treated with the isotype control, respectively.

As observed previously, the anti-PD-L1(mut)/TGFβ Trap control (Group 2) did not have any efficacy in this MC38 model. Anti-LAG3 as a single agent (Group 3) showed a moderate efficacy, achieving a T/C of 0.66 (p<0.05). However, combination with the Trap control (Group 5) did not improve its efficacy. Anti-TIM3 either as a single agent (Group 4) or in combination therapy with the Trap control (Group 6) did not show any efficacy.

SEQUENCES

SEQ ID NO: 1
Peptide sequence of the secreted anti-PD-L1 lambda light chain
QSALTQPASVSGSPGQSITISCTGTSSDVGGYNYVSWYQQHPGKAPKLMIYDVSNRPSGVSNRF
SGSKSGNTASLTISGLQAEDEADYYCSSYTSSSTRVEGTGTKVTVLGQPKANPTVTLEPPSSEE
LQANKATLVCLISDFYPGAVTVAWKADGSPVKAGVETTKPSKQSNNKYAASSYLSLTPEQWKSH
RSYSCQVTHEGSTVEKTVAPTECS SEQ ID NO: 2
Peptide sequence of the secreted H chain of anti-PDL1
EVQLLESGGGLVQPGGSLRLSCAASGFTESSYIMMWVRQAPGKGLEWVSSIYPSGGITFYADTV
KGRFTISRDNSKNTLYLQMNSLRAEDTAVYYCARIKLGTVTTVDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGGPSVFLEPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTIPPVLDSDGSFELYSKLTVDKSRWQQGNVFSCSVMHEALHNHYTQKSLSLSP
GK SEQ ID NO: 3
Peptide sequence of the secreted H chain of anti-PDL1/TGFβ Trap
EVQLLESGGGLVQPGGSLRLSCAASGFTESSYIMMWVRQAPGKGLEWVSSIYPSGGITFYADTV
KGRFTISRDNSKNTLYLQMNSLRAEDTAVYYCARIKLGTVTTVDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGGPSVFLEPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTIPPVLDSDGSFELYSKLTVDKSRWQQGNVESCSVMHEALHNHYTQKSLSLSP
GAGGGGSGGGGSGGGGSGGGGSGIPPHVQKSVNNDMIVTDNNGAVKFPQLCKFCDVRFSTCDNQ
KSCMSNCSITSICEKPQEVCVAVWRKNDENITLETVCHDPKLPYHDFILEDAASPKCIMKEKKK
PGETFFMCSCSSDECNDNIIFSEEYNTSNPD SEQ ID NO: 4
DNA sequence from the translation initiation codon to the translation
stop codon of the anti-PD-L1 lambda light chain (the leader sequence
preceding the VL is the signal peptide from urokinase plasminogen
activator)
atgagggccctgctggctagactgctgctgtgcgtgctggtcgtgtccgacagcaagggcCAGT
CCGCCCTGACCCAGCCTGCCTCCGTGTCTGGCTCCCCTGGCCAGTCCATCACCATCAGCTGCAC
CGGCACCTCCAGCGACGTGGGCGGCTACAACTACGTGTCCTGGTATCAGCAGCACCCCGGCAAG
GCCCCCAAGCTGATGATCTACGACGTGTCCAACCGGCCCTCCGGCGTGTCCAACAGATTCTCCG
GCTCCAAGTCCGGCAACACCGCCTCCCTGACCATCAGCGGACTGCAGGCAGAGGACGAGGCCGA
CTACTACTGCTCCTCCTACACCTCCTCCAGCACCAGAGTGTTCGGCACCGGCACAAAAGTGACC

```
GTGCTGggccagcccaaggccaacccaaccgtgacactgttccccccatcctccgaggaactgc
aggccaacaaggccaccctggtctgcctgatctcagatttctatccaggcgccgtgaccgtggc
ctggaaggctgatggctccccagtgaaggccggcgtggaaaccaccaagccctccaagcagtcc
aacaacaaatacgccgcctcctcctacctgtccctgacccccgagcagtggaagtcccaccggt
cctacagctgccaggtcacacacgagggctccaccgtggaaaagaccgtcgcccccaccgagtg
ctcaTGA SEQ ID NO: 5
DNA sequence from the translation initiation codon to the translation
stop codon (mVK SP leader: small underlined; VH: capitals; IgG1m3
with K to A mutation: small letters; (G4S)x4-G linker
(SEQ ID NO: 11):
bold capital letters; TGFPRII: bold underlined small letters; two stop
codons: bold underlined capital letters):

atggaaacagacaccctgctgctgtgggtgctgctgctgtgggtgcccggctccacaggcGAGG
TGCAGCTGCTGGAATCCGGCGGAGGACTGGTGCAGCCTGGCGGCTCCCTGAGACTGTCTTGCGC
CGCCTCCGGCTTCACCTTCTCCAGCTACATCATGATGTGGGTGCGACAGGCCCCTGGCAAGGGC
CTGGAATGGGTGTCCTCCATCTACCCCTCCGGCGGCATCACCTTCTACGCCGACACCGTGAAGG
GCCGGTTCACCATCTCCCGGGACAACTCCAAGAACACCCTGTACCTGCAGATGAACTCCCTGCG
GGCCGAGGACACCGCCGTGTACTACTGCGCCCGGATCAAGCTGGGCACCGTGACCACCGTGGAC
TACTGGGGCCAGGGCACCCTGGTGACAGTGTCCTCCgctagcaccaagggcccatcggtcttcc
ccctggcaccctcctccaagagcacctctgggggcacagcggccctgggctgcctggtcaagga
ctacttccccgaacggtgacggtgtcgtggaactcaggcgccctgaccagcggcgtgcacacc
ttccggctgtcctacagtcctcaggactctactccctcagcagcgtggtgaccgtgccctca
gcagcttgggcacccagacctacatctgcaacgtgaatcacaagcccagcaacaccaaggtgga
caagagagttgagcccaaatcttgtgacaaaactcacacatgcccaccgtgcccagcacctgaa
ctcctggggggaccgtcagtcttcctcttccccccaaaacccaaggacaccctcatgatctccc
ggacccctgaggtcacatgcgtggtggtggacgtgagccacgaagaccctgaggtcaagttcaa
ctggtacgtggacggcgtggaggtgcataatgccaagacaaagccgcgggaggagcagtacaac
agcacgtaccgtgtggtcagcgtcctcaccgtcctgcaccaggactggctgaatggcaaggagt
acaagtgcaaggtctccaacaaagcctcccagccccatcgagaaaaccatctccaaagccaa
agggcagccccgagaaccacaggtgtacaccctgcccccatcccgggaggagatgaccaagaac
caggtcagcctgacctgcctggtcaaaggcttctatcccagcgacatcgccgtggagtgggaga
gcaatgggcagccggagaacaactacaagaccacgcctcccgtgctggactccgacggctcctt
cttcctctatagcaagctcaccgtggacaagagcaggtggcagcaggggaacgtcttctcatgc
tccgtgatgcatgaggctctgcacaaccactacacgcagaagagcctctccctgtcccgggtg
ctGGCGGCGGAGGAAGCGGAGGAGGTGGCAGCGGTGGCGGTGGCTCCGGCGGAGGTGGCTCCGG
Aatccctccccacgtgcagaagtccgtgaacaacgacatgatcgtgaccgacaacaacggcgcc
gtgaagttccctcagctgtgcaagttctgcgacgtgaggttcagcacctgcgacaaccagaagt
cctgcatgagcaactgcagcatcacaagcatctgcgagaagcccaggaggtgtgtgtggccgt
gtggaggaagaacgacgaaaacatcaccctcgagaccgtgtgccatgaccccaagctgccctac
cacgacttcatcctggaagacgccgcctcccccaagtgcatcatgaaggagaagaagaagcccg
gcgagaccttcttcatgtgcagctgcagcagcgacgagtgcaatgacaacatcatctttagcga
ggagtacaacaccagcaaccccgacTGATAA SEQ ID NO: 6
Polypeptide sequence of the secreted lambda light chain of
anti-PD-L1(mut)/TGFβ Trap, with mutations A31G, D52E, R99Y
QSALTQPASVSGSPGQSITISCTGTSSDVGGYNYVSWYQQHPGKAPKLMIYEVSNRPSGVSNRF
SGSKSGNTASLTISGLQAEDEADYYCSSYTSSSTYVEGTGTKVTVLGQPKANPTVTLEPPSSEE
LQANKATLVCLISDFYPGAVTVAWKADGSPVKAGVETTKPSKQSNNKYAASSYLSLTPEQWKSH
RSYSCQVTHEGSTVEKTVAPTECS SEQ ID NO: 7
Polypeptide sequence of the secreted heavy chain of anti-PD-L1(mut)/
TGFβ Trap
EVQLLESGGGLVQPGGSLRLSCAASGFTESMYMMMWVRQAPGKGLEWVSSIYPSGGITFYADSV
KGRFTISRDNSKNTLYLQMNSLRAEDTAIYYCARIKLGTVTTVDYWQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGGPSVFLEPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTIPPVLDSDGSFELYSKLTVDKSRWQQGNVFSCSVMHEALHNHYTQKSLSLSP
GAGGGGSGGGGSGGGGSGGGGSGIPPHVQKSVNNDMIVTDNNGAVKFPQLCKFCDVRFSTCDNQ
KSCMSNCSITSICEKPQEVCVAVWRKNDENITLETVCHDPKLPYHDFILEDAASPKCIMKEKKK
PGETFFMCSCSSDECNDNIIFSEEYNTSNPD SEQ ID NO: 8
Human TGFβRII Isoform A Precursor Polypeptide (NCBI RefSeq
Accession No: NP_001020018)
MGRGLLRGLWPLHIVLWTRIASTIPPHVQKSDVEMEAQKDEIICPSCNRTAHPLRHINNDMIVT
DNNGAVKFPQLCKFCDVRFSTCDNQKSCMSNCSITSICEKPQEVCVAVWRKNDENITLETVCHD
PKLPYHDFILEDAASPKCIMKEKKKPGETFFMCSCSSDECNDNIIFSEEYNTSNPDLLLVIFQV
TGISLLPPLGVAISVIIIFYCYRVNRQQKLSSTWETGKTRKLMEFSEHCAIILEDDRSDISSTC
ANNINHNTELLPIELDTLVGKGRFAEVYKAKLKQNTSEQFETVAVKIFPYEEYASWKTEKDIFS
DINLKHENILQFLTAEERKTELGKQYWLITAFHAKGNLQEYLTRHVISWEDLRKLGSSLARGIA
HLHSDHTPCGRPKMPIVHRDLKSSNILVKNDLTCCLCDFGLSLRLDPTLSVDDLANSGQVGTAR
```

```
YMAPEVLESRMNLENVESFKQTDVYSMALVLWEMTSRCNAVGEVKDYEPPFGSKVREHPCVESM
KDNVLRDRGRPEIPSFWLNHQGIQMVCETLTECWDHDPEARLTAQCVAERFSELEHLDRLSGRS
CSEEKIPEDGSLNTTK

SEQ ID NO: 9
Human TGFβRII Isoform B Precursor Polypeptide
(NCBI RefSeq Accession No: NP_003233
MGRGLLRGLWPLHIVLWTRIASTIPPHVQKSVNNDMIVTDNNGAVKFPQLCKFCDVRFSTCDNQ
KSCMSNCSITSICEKPQEVCVAVWRKNDENITLETVCHDPKLPYHDFILEDAASPKCIMKEKKK
PGETFFMCSCSSDECNDNIIFSEEYNTSNPDLLLVIFQVTGISLLPPLGVAISVIIIFYCYRVN
RQQKLSSTWETGKTRKLMEFSEHCAIILEDDRSDISSTCANNINHNTELLPIELDTLVGKRFA
EVYKAKLKQNTSEQFETVAVKIFPYEEYASWKTEKDIFSDINLKHENILQFLTAEERKTELGKQ
YWLITAFHAKGNLQEYLTRHVISWEDLRKLGSSLARGIAHLHSDHTPCGRPKMPIVHRDLKSSN
ILVKNDLTCCLCDFGLSLRLDPTLSVDDLANSGQVGTARYMAPEVLESRMNLENVESFKQTDVY
SMALVLWEMTSRCNAVGEVKDYEPPFGSKVREHPCVESMKDNVLRDRGRPEIPSFWLNHQGIQM
VCETLTECWDHDPEARLTAQCVAERFSELEHLDRLSGRSCSEEKIPEDGSLNTTK SEQ ID NO: 10
A Human TGFβRII Isoform B Extracellular Domain Polypeptide
IPPHVQKSVNNDMIVTDNNGAVKFPQLCKFCDVRFSTCDNQKSCMSNCSITSICEKPQEVCVAV
WRKNDENITLETVCHDPKLPYHDFILEDAASPKCIMKEKKKPGETFFMCSCSSDECNDNIIFSE
EYNTSNPD SEQ ID NO: 11
(Gly4Ser)4Gly linker
GGGGSGGGGSGGGGSGGGGSG SEQ ID NO: 12
Polypeptide sequence of the secreted heavy chain variable region of
anti-PD-L1 antibody MPDL3280A
EVQLVESGGGLVQPGGSLRLSCAASGFTFSDSWIHWVRQAPGKGLEWVAWISPYGGSTYY
ADSVKGRFTISADTSKNTAYLQMNSLRAEDTAVYYCARRHWPGGFDYWGQGTLVTVSS SEQ ID NO: 13
Polypeptide sequence of the secreted light chain variable region of
anti-PD-L1 antibody MPDL3280A and the anti-PD-L1 antibody YW243.55S70
DIQMTQSPSSLSASVGDRVTITCRASQDVSTAVAWYQQKPGKAPKLLIYSASFLYSGVPSRFSG
SGSGTDFTLTISSLQPEDFATYYCQQYLYHPATFGQGTKVEIKR SEQ ID NO: 14
Polypeptide sequence of the secreted heavy chain variable region of
anti-PD-L1 antibody YW243.55S70
EVQLVESGGGLVQPGGSLRLSCAASGFTFSDSWIHWVRQAPGKGLEWVAWISPYGGSTYYADSV
KGRFTISADTSKNTAYLQMNSLRAEDTAVYYCARRHWPGGFDYWGQGTLVTVSA
```

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Various structural elements of the different embodiments and various disclosed method steps may be utilized in various combinations and permutations, and all such variants are to be considered forms of the invention. Scope of the invention is thus indicated by the appended claims rather than by the foregoing description, and all changes that come within the meaning and range of equivalency of the claims are intended to be embraced therein.

What is claimed is:

1. A protein comprising:
   a) human Transforming Growth Factor β Receptor II (TGFβRII), or a fragment thereof capable of binding Transforming Growth Factor β (TGFβ); and
   b) an antibody, or an antigen-binding fragment thereof, that binds human protein Programmed Death Ligand 1 (PD-L1), wherein the antibody, or antigen-binding fragment thereof comprises a heavy chain variable region polypeptide comprising an HVR-H1, HVR-H2, and HVR-H3 sequence and a light chain variable region polypeptide comprising an HVR-L1, HVR-L2, and HVR-L3 sequence, wherein
   the HVR-H1 sequence is $X_1YX_2MX_3$ (SEQ ID NO:21);
   the HVR-H2 sequence is SIYPSGG$X_4$ TFY AD$X_5$ VKG (SEQ ID NO:22);
   the HVR-H3 sequence is IKLGTVTTV$X_6$Y (SEQ ID NO:23); and further wherein
   $X_1$ is K, R, T, Q, G, A, W, M, I, or S; $X_2$ is V, R, K, L, M, or I; $X_3$ is H, T, N, Q, A, V, Y, W, F, or M; $X_4$ is F or I; $X_5$ is S or T; and $X_6$ is E or D; and wherein the HVR-L1 sequence is TGT$X_7X_8$DVG$X_9$YNYVS (SEQ ID NO:28);

the HVR-L2 sequence is $X_{10}$V$X_{11}X_{12}$RPS (SEQ ID NO:29);

the HVR-L3 sequence is SS$X_{13}$T$X_{14}X_{15}X_{16}X_{17}$RV (SEQ ID NO:30); and further wherein $X_7$ is N or S; $X_8$ is T, R, or S; $X_9$ is A or G; $X_{10}$ is E or D; $X_{11}$ is I, N or S;

$X_{12}$ is D, H or N; $X_{13}$ is F or Y; $X_{14}$ is N or S; $X_{15}$ is R, T or S; $X_{16}$ is G or S; and $X_{17}$ is I or T.

2. A protein comprising:

a first polypeptide comprising:

a) at least a variable region of a heavy chain of an antibody that binds human protein Programmed Death Ligand 1 (PD-L1); and b) human Transforming Growth Factor β Receptor II (TGFβRII), or a fragment thereof capable of binding TGFβ, wherein said variable region of the heavy chain comprises an HVR-H1, HVR-H2, and HVR-H3 sequence, wherein the HVR-H1 sequence is $X_1YX_2MX_3$ (SEQ ID NO: 21);

the HVR-H2 sequence is SIYPSGG$X_4$ TFY AD$X_5$ VKG (SEQ ID NO: 22);

the HVR-H3 sequence is IKLGTVTTV$X_6$Y (SEQ ID NO: 23); and further wherein $X_1$ is K, R, T, Q, G, A, W, M, I, or S; $X_2$ is V, R, K, L, M, or I; $X_3$ is H, T, N, Q, A, V, Y, W, F, or M; $X_4$ is F or I; $X_5$ is S or T; and $X_6$ is E or D; and a second polypeptide comprising at least a variable region of a light chain of an antibody that binds PD-L1, said variable region of the light chain comprising an HVR-L1, HVR-L2, and HVR-L3 sequence, wherein the HVR-L1 sequence is TGT$X_7X_8$DVG$X_9$YNYVS (SEQ ID NO:28);

the HVR-L2 sequence is $X_{10}$V$X_{11}X_{12}$RPS (SEQ ID NO:29);

the HVR-L3 sequence is SS$X_{13}$T$X_{14}X_{15}X_{16}X_{17}$RV (SEQ ID NO:30); and further wherein $X_7$ is N or S; $X_8$ is T, R, or S; $X_9$ is A or G; $X_{10}$ is E or D; $X_{11}$ is I, N or S;

$X_{12}$ is D, H or N; $X_{13}$ is F or Y; $X_{14}$ is N or S; $X_{15}$ is R, T or S; $X_{16}$ is G or S; and $X_{17}$ is I or T.

3. The protein of claim 2, wherein the first polypeptide further comprises an amino acid linker connecting the C-terminus of the variable region of the heavy chain to the N-terminus of the human TGFβRII or fragment thereof.

4. The protein of claim 1, wherein $X_1$ is M, I, or S; $X_2$ is R, K, L, M, or I; $X_3$ is F or M; $X_4$ is F or I; $X_5$ is S or T; and $X_6$ is E or D.

5. The protein of claim 1, wherein $X_1$ is M, I, or S; $X_2$ is L, M, or I; $X_3$ is F or M; $X_4$ is I; $X_5$ is S or T; and $X_6$ is D.

6. The protein of claim 1, wherein $X_1$ is S; $X_2$ is I; $X_3$ is M; $X_4$ is I; $X_5$ is T; and $X_6$ is D.

7. The protein of claim 1, wherein $X_7$ is N or S; $X_8$ is T, R, or S; $X_9$ is A or G; $X_{10}$ is E or D; $X_{11}$ is N or S; $X_{12}$ is N; $X_{13}$ is F or Y; $X_{14}$ is S; $X_{15}$ is S; $X_{16}$ is G or S; $X_{17}$ is T.

8. The protein of claim 1, wherein the HVR-H1 sequence comprises SYIMM (SEQ ID NO:35), the HVR-H2 sequence comprises SIYPSGGITFYADTVKG (SEQ ID NO:36), and the HVR-H3 sequence comprises IKLGTVTTVDY (SEQ ID NO:37).

9. The protein of claim 1, wherein the HVR-L1 sequence comprises TGTSSDVGGYNYVS (SEQ ID NO:38), the HVR-L2 sequence comprises DVSNRPS (SEQ ID NO:39), and the HVR-L3 sequence comprises SSYTSSSTRV (SEQ ID NO:40).

10. The protein of claim 1, wherein the human TGFβRII, or a fragment thereof capable of binding TGFβ, comprises the amino acid residues of SEQ ID NO:10.

11. The protein of claim 1, wherein the heavy chain variable region polypeptide comprises the amino acid sequence of SEQ ID NO:46 and the light chain variable region polypeptide comprises the amino acid sequence of SEQ ID NO:47.

12. The protein of claim 2, wherein $X_1$ is M, I, or S; $X_2$ is R, K, L, M, or I; $X_3$ is F or M; $X_4$ is F or I; $X_5$ is S or T; and $X_6$ is E or D.

13. The protein of claim 2, wherein $X_1$ is M, I, or S; $X_2$ is L, M, or I; $X_3$ is F or M; $X_4$ is I; $X_5$ is S or T; and $X_6$ is D.

14. The protein of claim 2, wherein $X_1$ is S; $X_2$ is I; $X_3$ is M; $X_4$ is I; $X_5$ is T; and $X_6$ is D.

15. The protein of claim 2, wherein $X_7$ is N or S; $X_8$ is T, R, or S; $X_9$ is A or G; $X_{10}$ is E or D; $X_{11}$ is N or S; $X_{12}$ is N; $X_{13}$ is F or Y; $X_{14}$ is S; $X_{15}$ is S; $X_{16}$ is G or S; $X_{17}$ is T.

16. The protein of claim 2, wherein the HVR-H1 sequence comprises SYIMM (SEQ ID NO:35), the HVR-H2 sequence comprises SIYPSGGITFYADTVKG (SEQ ID NO:36), and the HVR-H3 sequence comprises IKLGTVTTVDY (SEQ ID NO:37).

17. The protein of claim 2, wherein the HVR-L1 sequence comprises TGTSSDVGGYNYVS (SEQ ID NO:38), the HVR-L2 sequence comprises DVSNRPS (SEQ ID NO:39), and the HVR-L3 sequence comprises SSYTSSSTRV (SEQ ID NO:40).

18. The protein of claim 2, comprising a second first polypeptide and a second second polypeptide, wherein the first polypeptide and second polypeptide form an antigen-binding site that binds PD-L1 and the second first polypeptide and second second polypeptide form an antigen-binding site that binds PD-L1.

19. The protein of claim 2, wherein the human TGFβRII, or a fragment thereof capable of binding TGFβ, comprises the amino acid residues of SEQ ID NO:10.

20. The protein of claim 2, wherein the variable region of the heavy chain comprises the amino acid sequence of SEQ ID NO:46 and the variable region of the light chain comprises the amino acid sequence of SEQ ID NO:47.

* * * * *

UNITED STATES PATENT AND TRADEMARK OFFICE
CERTIFICATE OF CORRECTION

| | |
|---|---|
| PATENT NO. | : 11,370,819 B2 |
| APPLICATION NO. | : 16/522304 |
| DATED | : June 28, 2022 |
| INVENTOR(S) | : Kin-Ming Lo |

It is certified that error appears in the above-identified patent and that said Letters Patent is hereby corrected as shown below:

In the Claims

In Claim 7, at Column 90, Line 30, replace "$X_{16}$ is G or S; $X_{17}$ is T." with "$X_{16}$ is G or S; and $X_{17}$ is T."

In Claim 15, at Column 90, Line 60, replace "$X_{16}$ is G or S; $X_{17}$ is T." with "$X_{16}$ is G or S; and $X_{17}$ is T."

Signed and Sealed this
Twenty-seventh Day of December, 2022

Katherine Kelly Vidal
*Director of the United States Patent and Trademark Office*